(12) United States Patent  (10) Patent No.: US 8,547,248 B2
Zdeblick et al.  (45) Date of Patent: Oct. 1, 2013

(54) IMPLANTABLE ZERO-WIRE COMMUNICATIONS SYSTEM

(75) Inventors: Mark J. Zdeblick, Portola Valley, CA (US); Timothy Robertson, Belmont, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 1077 days.

(21) Appl. No.: 12/063,095

(22) PCT Filed: Sep. 1, 2006

(86) PCT No.: PCT/US2006/034258
§ 371 (c)(1),
(2), (4) Date: Jun. 5, 2008

(87) PCT Pub. No.: WO2007/028035
PCT Pub. Date: Mar. 8, 2007

(65) Prior Publication Data
US 2008/0306359 A1  Dec. 11, 2008

Related U.S. Application Data

(60) Provisional application No. 60/713,881, filed on Sep. 1, 2005, provisional application No. 60/713,680, filed on Sep. 1, 2005, provisional application No. 60/739,174, filed on Nov. 23, 2005.

(51) Int. Cl.
*G08C 17/00*  (2006.01)

(52) U.S. Cl.
USPC ........ 340/870.28; 607/60; 600/561; 600/549; 600/109; 600/302

(58) Field of Classification Search
USPC .............. 340/870.28; 607/60; 600/561, 549, 600/587, 109, 302
See application file for complete search history.

(56) References Cited

U.S. PATENT DOCUMENTS

| | | | |
|---|---|---|---|
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |

(Continued)

FOREIGN PATENT DOCUMENTS

| | | |
|---|---|---|
| CN | 1991868 | 7/2007 |
| CN | 101005470 | 7/2007 |

(Continued)

OTHER PUBLICATIONS

Hotz "The Really Smart Phone" The Wall Street Journal, What They Know (2011); 6 pp.

(Continued)

*Primary Examiner* — Albert Wong
(74) *Attorney, Agent, or Firm* — Bozicevic, Field & Francis LLP; Bret E. Field

(57) ABSTRACT

The present invention provides implantable systems that communicate wirelessly with each other using a unique format that enables devices configurations and applications heretofore not possible. Embodiments of the present invention provide communication apparatuses and methods for exchanging information with implantable medical devices. In some embodiments, two implantable devices communicate with each other using quasi-electrostatic signal transmission in a long wavelength/low frequency electromagnetic band, with the patient's body acting as a conductive medium.

54 Claims, 18 Drawing Sheets

(56) References Cited

U.S. PATENT DOCUMENTS

| | | |
|---|---|---|
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,949,388 A | 4/1976 | Fuller |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,494,950 A | 1/1985 | Fischell |
| 4,559,950 A | 12/1985 | Vaughan |
| 4,635,296 A | 1/1987 | Dinsmore |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,725,997 A | 2/1988 | Urquhart et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,844,076 A | 7/1989 | Lesho |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urguhart |
| 5,099,227 A | 3/1992 | Geiszler et al. |
| 5,167,626 A | 12/1992 | Casper |
| 5,176,626 A | 1/1993 | Soehendra |
| 5,261,402 A | 11/1993 | DiSabito |
| 5,263,481 A | 11/1993 | Axelgaard et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,331,966 A | 7/1994 | Bennett et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,485,841 A | 1/1996 | Watkin et al. |
| 5,511,548 A | 4/1996 | Riazzi et al. |
| 5,513,637 A | 5/1996 | Twiss et al. |
| 5,567,210 A | 10/1996 | Bates et al. |
| 5,596,302 A | 1/1997 | Mastrocola et al. |
| 5,600,548 A | 2/1997 | Nguyen et al. |
| 5,630,835 A | 5/1997 | Brownlee |
| 5,634,468 A | 6/1997 | Platt |
| 5,645,063 A | 7/1997 | Straka et al. |
| 5,697,958 A | 12/1997 | Paul et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,796,827 A | 8/1998 | Coppersmith et al. |
| 5,802,467 A | 9/1998 | Salazar |
| 5,829,444 A | 11/1998 | Ferre et al. |
| 5,833,716 A | 11/1998 | Bar-Or |
| 5,842,977 A | 12/1998 | Lesho et al. |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,905,261 A | 5/1999 | Schotland et al. |
| 5,921,925 A | 7/1999 | Cartmell et al. |
| 5,925,030 A | 7/1999 | Gross et al. |
| 5,957,854 A | 9/1999 | Besson |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,200,265 B1 | 3/2001 | Walsh et al. |
| 6,201,387 B1 | 3/2001 | Govari |
| 6,204,764 B1 | 3/2001 | Maloney |
| 6,206,702 B1 | 3/2001 | Hayden et al. |
| 6,208,894 B1 | 3/2001 | Schulman et al. |
| 6,211,799 B1 | 4/2001 | Post et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson |
| 6,315,719 B1 | 11/2001 | Rode et al. |
| 6,336,031 B1 | 1/2002 | Schyndel |
| 6,342,774 B1 | 1/2002 | Kreisinger et al. |
| 6,358,202 B1 | 3/2002 | Arent |
| 6,359,597 B2 | 3/2002 | Haj-Yousef |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,494,829 B1 | 12/2002 | New et al. |
| 6,496,705 B1 | 12/2002 | Ng et al. |
| 6,505,072 B1 | 1/2003 | Linder et al. |
| 6,526,315 B1 | 2/2003 | Inagawa |
| 6,531,026 B1 | 3/2003 | Takeichi et al. |
| 6,544,174 B2 | 4/2003 | West |
| 6,564,079 B1 | 5/2003 | Cory |
| 6,572,636 B1 | 6/2003 | Hagen et al. |
| 6,574,510 B2 | 6/2003 | Von Arx et al. |
| 6,577,893 B1 | 6/2003 | Besson |
| 6,579,231 B1 | 6/2003 | Phipps |
| 6,595,929 B2 | 7/2003 | Stivoric |
| 6,605,038 B1 | 8/2003 | Teller |
| 6,609,018 B2 | 8/2003 | Cory |
| 6,612,984 B1 | 9/2003 | Kerr |
| 6,630,833 B2 | 10/2003 | Scott |
| 6,632,175 B1 | 10/2003 | Marshall |

| Patent No. | Kind | Date | Inventor |
|---|---|---|---|
| 6,632,216 | B2 | 10/2003 | Houzego et al. |
| 6,635,279 | B2 | 10/2003 | Kolter et al. |
| 6,643,541 | B2 | 11/2003 | Mok et al. |
| 6,654,638 | B1 | 11/2003 | Sweeney |
| 6,663,846 | B1 | 12/2003 | McCombs |
| 6,673,474 | B2 | 1/2004 | Yamamoto |
| 6,680,923 | B1 | 1/2004 | Leon |
| 6,689,117 | B2 | 2/2004 | Sweeney et al. |
| 6,694,161 | B2 | 2/2004 | Mehrotra |
| 6,704,602 | B2 | 3/2004 | Berg et al. |
| 6,706,040 | B2 | 3/2004 | Mahon et al. |
| 6,720,923 | B1 | 4/2004 | Hayward et al. |
| 6,738,671 | B2 | 5/2004 | Christophersom et al. |
| 6,740,033 | B1 | 5/2004 | Olejniczak et al. |
| 6,745,082 | B2 | 6/2004 | Axelgaard et al. |
| 6,754,472 | B1 | 6/2004 | Williams et al. |
| 6,755,783 | B2 | 6/2004 | Cosentino |
| 6,757,523 | B2 | 6/2004 | Fry |
| 6,759,968 | B2 | 7/2004 | Zierolf |
| 6,766,201 | B2 | 7/2004 | Von Arx et al. |
| 6,800,060 | B2 | 10/2004 | Marshall |
| 6,801,137 | B2 | 10/2004 | Eggers et al. |
| 6,809,701 | B2 | 10/2004 | Amundson et al. |
| 6,814,706 | B2 | 11/2004 | Barton et al. |
| 6,822,554 | B2 | 11/2004 | Vrijens et al. |
| 6,836,862 | B1 | 12/2004 | Erekson et al. |
| 6,839,659 | B2 | 1/2005 | Tarassenko et al. |
| 6,840,904 | B2 | 1/2005 | Goldberg |
| 6,842,636 | B2 | 1/2005 | Perrault |
| 6,845,272 | B1 | 1/2005 | Thomsen |
| 6,864,780 | B2 | 3/2005 | Doi |
| 6,879,810 | B2 | 4/2005 | Bouet |
| 6,882,881 | B1 | 4/2005 | Lesser et al. |
| 6,897,788 | B2 | 5/2005 | Khair et al. |
| 6,909,878 | B2 | 6/2005 | Haller |
| 6,922,592 | B2 | 7/2005 | Thompson et al. |
| 6,928,370 | B2 | 8/2005 | Anuzis et al. |
| 6,929,636 | B1 | 8/2005 | Von Alten |
| 6,937,150 | B2 | 8/2005 | Medema |
| 6,942,616 | B2 | 9/2005 | Kerr |
| 6,951,536 | B2 | 10/2005 | Yokoi |
| 6,957,107 | B2 | 10/2005 | Rogers et al. |
| 6,959,929 | B2 | 11/2005 | Pugnet et al. |
| 6,968,153 | B1 | 11/2005 | Heinonen |
| 6,987,965 | B2 | 1/2006 | Ng et al. |
| 6,990,082 | B1 | 1/2006 | Zehavi et al. |
| 7,002,476 | B2 | 2/2006 | Rapchak |
| 7,004,395 | B2 | 2/2006 | Koenck |
| 7,009,634 | B2 | 3/2006 | Iddan et al. |
| 7,009,946 | B1 | 3/2006 | Kardach |
| 7,013,162 | B2 | 3/2006 | Gorsuch |
| 7,016,648 | B2 | 3/2006 | Haller |
| 7,020,508 | B2 | 3/2006 | Stivoric |
| 7,024,248 | B2 | 4/2006 | Penner et al. |
| 7,031,745 | B2 | 4/2006 | Shen |
| 7,031,857 | B2 | 4/2006 | Tarassenko et al. |
| 7,039,453 | B2 | 5/2006 | Mullick |
| 7,044,911 | B2 | 5/2006 | Drinan et al. |
| 7,046,649 | B2 | 5/2006 | Awater et al. |
| 7,118,531 | B2 | 10/2006 | Krill |
| 7,127,300 | B2 | 10/2006 | Mazar et al. |
| 7,146,228 | B2 | 12/2006 | Nielsen |
| 7,146,449 | B2 | 12/2006 | Do et al. |
| 7,149,581 | B2 | 12/2006 | Goedeke et al. |
| 7,154,071 | B2 | 12/2006 | Sattler et al. |
| 7,155,232 | B2 | 12/2006 | Godfrey et al. |
| 7,160,258 | B2 | 1/2007 | Imran |
| 7,161,484 | B2 | 1/2007 | Tsoukalis |
| 7,164,942 | B2 | 1/2007 | Avrahami |
| 7,171,166 | B2 | 1/2007 | Ng et al. |
| 7,171,177 | B2 | 1/2007 | Park et al. |
| 7,171,259 | B2 | 1/2007 | Rytky |
| 7,176,784 | B2 | 2/2007 | Gilbert et al. |
| 7,187,960 | B2 | 3/2007 | Abreu |
| 7,188,767 | B2 | 3/2007 | Penuela |
| 7,194,038 | B1 | 3/2007 | Inkinen |
| 7,206,630 | B1 | 4/2007 | Tarler |
| 7,209,790 | B2 | 4/2007 | Thompson et al. |
| 7,215,660 | B2 | 5/2007 | Perlman |
| 7,215,991 | B2 | 5/2007 | Besson |
| 7,218,967 | B2 | 5/2007 | Bergelson |
| 7,231,451 | B2 | 6/2007 | Law |
| 7,243,118 | B2 | 7/2007 | Lou |
| 7,246,521 | B2 | 7/2007 | Kim |
| 7,249,212 | B2 | 7/2007 | Do |
| 7,252,792 | B2 | 8/2007 | Perrault |
| 7,253,716 | B2 | 8/2007 | Lovoi et al. |
| 7,261,690 | B2 | 8/2007 | Teller |
| 7,270,633 | B1 | 9/2007 | Goscha |
| 7,273,454 | B2 | 9/2007 | Raymond et al. |
| 7,285,090 | B2 | 10/2007 | Stivoric et al. |
| 7,289,855 | B2 | 10/2007 | Nghiem |
| 7,291,497 | B2 | 11/2007 | Holmes |
| 7,292,139 | B2 | 11/2007 | Mazar et al. |
| 7,294,105 | B1 | 11/2007 | Islam |
| 7,313,163 | B2 | 12/2007 | Liu |
| 7,317,378 | B2 | 1/2008 | Jarvis et al. |
| 7,318,808 | B2 | 1/2008 | Tarassenko et al. |
| 7,336,929 | B2 | 2/2008 | Yasuda |
| 7,342,895 | B2 | 3/2008 | Serpa |
| 7,346,380 | B2 | 3/2008 | Axelgaard et al. |
| 7,349,722 | B2 | 3/2008 | Witkowski et al. |
| 7,352,998 | B2 | 4/2008 | Palin |
| 7,353,258 | B2 | 4/2008 | Washburn |
| 7,357,891 | B2 | 4/2008 | Yang et al. |
| 7,359,674 | B2 | 4/2008 | Markki |
| 7,366,558 | B2 | 4/2008 | Virtanen et al. |
| 7,368,190 | B2 | 5/2008 | Heller et al. |
| 7,368,191 | B2 | 5/2008 | Andelman et al. |
| 7,373,196 | B2 | 5/2008 | Ryu et al. |
| 7,375,739 | B2 | 5/2008 | Robbins |
| 7,376,435 | B2 | 5/2008 | McGowan |
| 7,382,263 | B2 | 6/2008 | Danowski et al. |
| 7,387,607 | B2 | 6/2008 | Holt |
| 7,388,903 | B2 | 6/2008 | Godfrey et al. |
| 7,389,088 | B2 | 6/2008 | Kim |
| 7,392,015 | B1 | 6/2008 | Farlow |
| 7,395,106 | B2 | 7/2008 | Ryu et al. |
| 7,396,330 | B2 | 7/2008 | Banet |
| 7,404,968 | B2 | 7/2008 | Abrams et al. |
| 7,413,544 | B2 | 8/2008 | Kerr |
| 7,414,534 | B1 | 8/2008 | Kroll et al. |
| 7,414,543 | B2 | 8/2008 | Rye et al. |
| 7,415,242 | B1 | 8/2008 | Ngan |
| 7,424,268 | B2 | 9/2008 | Diener |
| 7,424,319 | B2 | 9/2008 | Muehlsteff |
| 7,427,266 | B2 | 9/2008 | Ayer et al. |
| 7,471,665 | B2 | 12/2008 | Perlman |
| 7,499,674 | B2 | 3/2009 | Salokannel |
| 7,502,643 | B2 | 3/2009 | Farringdon et al. |
| 7,505,795 | B1 | 3/2009 | Lim et al. |
| 7,510,121 | B2 | 3/2009 | Koenck |
| 7,512,448 | B2 | 3/2009 | Malick |
| 7,515,043 | B2 | 4/2009 | Welch |
| 7,519,416 | B2 | 4/2009 | Sula et al. |
| 7,523,756 | B2 | 4/2009 | Minai |
| 7,525,426 | B2 | 4/2009 | Edelstein |
| 7,539,533 | B2 | 5/2009 | Tran |
| 7,542,878 | B2 | 6/2009 | Nanikashvili |
| 7,551,590 | B2 | 6/2009 | Haller |
| 7,554,452 | B2 | 6/2009 | Cole |
| 7,575,005 | B2 | 8/2009 | Mumford |
| 7,616,111 | B2 | 11/2009 | Covannon |
| 7,617,001 | B2 | 11/2009 | Penner et al. |
| 7,640,802 | B2 | 1/2010 | King et al. |
| 7,647,112 | B2 | 1/2010 | Tracey |
| 7,647,185 | B2 | 1/2010 | Tarassenko et al. |
| 7,653,031 | B2 | 1/2010 | Godfrey et al. |
| 7,672,714 | B2 | 3/2010 | Kuo |
| 7,673,679 | B2 | 3/2010 | Harrison et al. |
| 7,678,043 | B2 | 3/2010 | Gilad |
| 7,689,437 | B1 | 3/2010 | Teller et al. |
| 7,697,994 | B2 | 4/2010 | VanDanacker et al. |
| 7,720,036 | B2 | 5/2010 | Sadri |
| 7,729,776 | B2 | 6/2010 | Von Arx et al. |
| 7,733,224 | B2 | 6/2010 | Tran |
| 7,736,318 | B2 | 6/2010 | Cosentino |
| 7,756,587 | B2 | 7/2010 | Penner et al. |

| Patent/Pub No. | Date | Inventor |
|---|---|---|
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,904,133 B2 | 3/2011 | Gehman et al. |
| 8,073,707 B2 | 12/2011 | Teller et al. |
| 8,083,128 B2 | 12/2011 | Dembo et al. |
| 8,123,576 B2 | 2/2012 | Kim |
| 8,170,515 B2 | 5/2012 | Le Reverend et al. |
| 8,180,425 B2 | 5/2012 | Selvitelli et al. |
| 8,200,320 B2 | 6/2012 | Kovacs |
| 8,214,007 B2 | 7/2012 | Baker et al. |
| 8,227,667 B2 | 7/2012 | Miller et al. |
| 8,238,998 B2 | 8/2012 | Park |
| 8,249,686 B2 | 8/2012 | Libbus et al. |
| 8,258,962 B2 | 9/2012 | Robertson et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0036674 A1 | 2/2003 | Bouton |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0169132 A1 | 9/2003 | Vaiser et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0004554 A1 | 1/2004 | Srinivasan et al. |
| 2004/0008123 A1 | 1/2004 | Carrender et al. |
| 2004/0018476 A1 | 1/2004 | LaDue |
| 2004/0024309 A1 | 2/2004 | Ferre et al. |
| 2004/0030260 A1 | 2/2004 | Arx |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0102219 A1 | 5/2004 | Bunton et al. |
| 2004/0106859 A1 | 6/2004 | Say et al. |
| 2004/0111011 A1 | 6/2004 | Uchiyama et al. |
| 2004/0115517 A1 | 6/2004 | Fukuda et al. |
| 2004/0121015 A1 | 6/2004 | Chidlaw et al. |
| 2004/0123871 A1 | 7/2004 | Wright et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0187875 A1 | 9/2004 | He et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075559 A1 | 4/2005 | Houzego et al. |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0110700 A1 | 5/2005 | Terry |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0134520 A1 | 6/2005 | Rawat et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0151625 A1 | 7/2005 | Lai |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0061472 A1 | 3/2006 | Lovoi et al. |

| | | |
|---|---|---|
| 2006/0065713 A1 | 3/2006 | Kingery |
| 2006/0068006 A1 | 3/2006 | Begleiter |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0268546 A1 | 11/2006 | Hoag |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0015421 A1 | 1/2008 | Penner |
| 2008/0020037 A1 | 1/2008 | Robertson et al. |
| 2008/0021519 A1 | 1/2008 | De Geest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |

| | | | | | |
|---|---|---|---|---|---|
| 2009/0069656 A1 | 3/2009 | Say et al. | 2009/0231125 A1 | 9/2009 | Baldus |
| 2009/0069657 A1 | 3/2009 | Say et al. | 2009/0234200 A1 | 9/2009 | Husheer |
| 2009/0069658 A1 | 3/2009 | Say et al. | 2009/0243833 A1 | 10/2009 | Huang |
| 2009/0076340 A1 | 3/2009 | Libbus et al. | 2009/0253960 A1 | 10/2009 | Takenaka et al. |
| 2009/0076343 A1 | 3/2009 | James | 2009/0256702 A1 | 10/2009 | Robertson |
| 2009/0076397 A1 | 3/2009 | Libbus et al. | 2009/0264714 A1 | 10/2009 | Chou |
| 2009/0082645 A1 | 3/2009 | Hafezi et al. | 2009/0264964 A1 | 10/2009 | Abrahamson |
| 2009/0087483 A1 | 4/2009 | Sison | 2009/0265186 A1 | 10/2009 | Tarassenko et al. |
| 2009/0088618 A1 | 4/2009 | Ameson | 2009/0273467 A1 | 11/2009 | Elixmann |
| 2009/0099435 A1 | 4/2009 | Say et al. | 2009/0281539 A1 | 11/2009 | Selig |
| 2009/0105561 A1 | 4/2009 | Boydon et al. | 2009/0292194 A1 | 11/2009 | Libbus et al. |
| 2009/0110148 A1 | 4/2009 | Zhang | 2009/0295548 A1 | 12/2009 | Ronkka |
| 2009/0112626 A1 | 4/2009 | Talbot | 2009/0296677 A1 | 12/2009 | Mahany |
| 2009/0124871 A1 | 5/2009 | Arshak | 2009/0303920 A1 | 12/2009 | Mahany |
| 2009/0131774 A1 | 5/2009 | Sweitzer | 2009/0306633 A1 | 12/2009 | Trovato et al. |
| 2009/0135886 A1 | 5/2009 | Robertson et al. | 2009/0312619 A1 | 12/2009 | Say et al. |
| 2009/0157113 A1 | 6/2009 | Marcotte | 2009/0318761 A1 | 12/2009 | Rabinovitz |
| 2009/0157358 A1 | 6/2009 | Kim | 2009/0318779 A1 | 12/2009 | Tran |
| 2009/0161602 A1 | 6/2009 | Matsumoto | 2009/0318783 A1 | 12/2009 | Rohde |
| 2009/0163789 A1 | 6/2009 | Say et al. | 2009/0318793 A1 | 12/2009 | Datta |
| 2009/0171180 A1 | 7/2009 | Pering | 2010/0001841 A1 | 1/2010 | Cardullo |
| 2009/0173628 A1 | 7/2009 | Say et al. | 2010/0006585 A1 | 1/2010 | Flowers et al. |
| 2009/0177055 A1 | 7/2009 | Say et al. | 2010/0010330 A1 | 1/2010 | Rankers |
| 2009/0177056 A1 | 7/2009 | Say et al. | 2010/0049004 A1 | 2/2010 | Edman et al. |
| 2009/0177057 A1 | 7/2009 | Say et al. | 2010/0049006 A1 | 2/2010 | Magar |
| 2009/0177058 A1 | 7/2009 | Say et al. | 2010/0049012 A1 | 2/2010 | Dijksman et al. |
| 2009/0177059 A1 | 7/2009 | Say et al. | 2010/0049069 A1 | 2/2010 | Tarassenko et al. |
| 2009/0177060 A1 | 7/2009 | Say et al. | 2010/0056878 A1 | 3/2010 | Partin |
| 2009/0177061 A1 | 7/2009 | Say et al. | 2010/0056891 A1 | 3/2010 | Say et al. |
| 2009/0177062 A1 | 7/2009 | Say et al. | 2010/0056939 A1 | 3/2010 | Tarassenko et al. |
| 2009/0177063 A1 | 7/2009 | Say et al. | 2010/0057041 A1 | 3/2010 | Hayter |
| 2009/0177064 A1 | 7/2009 | Say et al. | 2010/0062709 A1 | 3/2010 | Kato |
| 2009/0177065 A1 | 7/2009 | Say et al. | 2010/0063438 A1 | 3/2010 | Bengtsson |
| 2009/0177066 A1 | 7/2009 | Say et al. | 2010/0063841 A1 | 3/2010 | D'Ambrosia et al. |
| 2009/0182206 A1 | 7/2009 | Najafi | 2010/0069002 A1 | 3/2010 | Rong |
| 2009/0182212 A1 | 7/2009 | Say et al. | 2010/0081894 A1 | 4/2010 | Zdeblick et al. |
| 2009/0182213 A1 | 7/2009 | Say et al. | 2010/0099967 A1 | 4/2010 | Say et al. |
| 2009/0182214 A1 | 7/2009 | Say et al. | 2010/0099968 A1 | 4/2010 | Say et al. |
| 2009/0182215 A1 | 7/2009 | Say et al. | 2010/0099969 A1 | 4/2010 | Say et al. |
| 2009/0182388 A1 | 7/2009 | Von Arx | 2010/0100077 A1 | 4/2010 | Rush |
| 2009/0187088 A1 | 7/2009 | Say et al. | 2010/0100078 A1 | 4/2010 | Say et al. |
| 2009/0187089 A1 | 7/2009 | Say et al. | 2010/0106001 A1 | 4/2010 | Say et al. |
| 2009/0187090 A1 | 7/2009 | Say et al. | 2010/0118853 A1 | 5/2010 | Godfrey |
| 2009/0187091 A1 | 7/2009 | Say et al. | 2010/0139672 A1 | 6/2010 | Kroll et al. |
| 2009/0187092 A1 | 7/2009 | Say et al. | 2010/0160742 A1 | 6/2010 | Seidl et al. |
| 2009/0187093 A1 | 7/2009 | Say et al. | 2010/0168659 A1 | 7/2010 | Say et al. |
| 2009/0187094 A1 | 7/2009 | Say et al. | 2010/0179398 A1 | 7/2010 | Say et al. |
| 2009/0187095 A1 | 7/2009 | Say et al. | 2010/0185055 A1 | 7/2010 | Robertson |
| 2009/0187381 A1 | 7/2009 | King et al. | 2010/0191073 A1 | 7/2010 | Tarassenko et al. |
| 2009/0192351 A1 | 7/2009 | Nishino | 2010/0210299 A1 | 8/2010 | Gorbachov |
| 2009/0192368 A1 | 7/2009 | Say et al. | 2010/0222652 A1 | 9/2010 | Cho |
| 2009/0192369 A1 | 7/2009 | Say et al. | 2010/0228113 A1 | 9/2010 | Solosko |
| 2009/0192370 A1 | 7/2009 | Say et al. | 2010/0234706 A1 | 9/2010 | Gilland |
| 2009/0192371 A1 | 7/2009 | Say et al. | 2010/0234715 A1 | 9/2010 | Shin |
| 2009/0192372 A1 | 7/2009 | Say et al. | 2010/0234914 A1 | 9/2010 | Shen |
| 2009/0192373 A1 | 7/2009 | Say et al. | 2010/0245091 A1 | 9/2010 | Singh |
| 2009/0192374 A1 | 7/2009 | Say et al. | 2010/0249881 A1 | 9/2010 | Corndorf |
| 2009/0192375 A1 | 7/2009 | Say et al. | 2010/0256461 A1 | 10/2010 | Mohamedali |
| 2009/0192376 A1 | 7/2009 | Say et al. | 2010/0259543 A1 | 10/2010 | Tarassenko et al. |
| 2009/0192377 A1 | 7/2009 | Say et al. | 2010/0268048 A1 | 10/2010 | Say et al. |
| 2009/0192378 A1 | 7/2009 | Say et al. | 2010/0268049 A1 | 10/2010 | Say et al. |
| 2009/0192379 A1 | 7/2009 | Say et al. | 2010/0268050 A1 | 10/2010 | Say et al. |
| 2009/0198115 A1 | 8/2009 | Say et al. | 2010/0274111 A1 | 10/2010 | Say et al. |
| 2009/0198116 A1 | 8/2009 | Say et al. | 2010/0280345 A1 | 11/2010 | Say et al. |
| 2009/0198175 A1 | 8/2009 | Say et al. | 2010/0280346 A1 | 11/2010 | Say et al. |
| 2009/0203964 A1 | 8/2009 | Shimizu et al. | 2010/0295694 A1 | 11/2010 | Kauffman et al. |
| 2009/0203971 A1 | 8/2009 | Sciarappa | 2010/0298668 A1 | 11/2010 | Hafezi et al. |
| 2009/0203972 A1 | 8/2009 | Heneghan | 2010/0298730 A1 | 11/2010 | Tarassenko et al. |
| 2009/0203978 A1 | 8/2009 | Say et al. | 2010/0299155 A1 | 11/2010 | Findlay et al. |
| 2009/0204265 A1 | 8/2009 | Hackett | 2010/0312188 A1 | 12/2010 | Robertson et al. |
| 2009/0210164 A1 | 8/2009 | Say et al. | 2010/0312580 A1 | 12/2010 | Tarassenko et al. |
| 2009/0216101 A1 | 8/2009 | Say et al. | 2010/0332443 A1 | 12/2010 | Gartenberg |
| 2009/0216102 A1 | 8/2009 | Say et al. | 2011/0009715 A1 | 1/2011 | O'Reilly et al. |
| 2009/0227204 A1 | 9/2009 | Robertson et al. | 2011/0040203 A1 | 2/2011 | Savage et al. |
| 2009/0227876 A1 | 9/2009 | Tran | 2011/0050431 A1 | 3/2011 | Hood et al. |
| 2009/0227940 A1 | 9/2009 | Say et al. | 2011/0054265 A1 | 3/2011 | Hafezi et al. |
| 2009/0227941 A1 | 9/2009 | Say et al. | 2011/0065983 A1 | 3/2011 | Hafezi et al. |
| 2009/0227988 A1 | 9/2009 | Wood et al. | 2011/0077660 A1 | 3/2011 | Janik et al. |
| 2009/0228214 A1 | 9/2009 | Say et al. | 2011/0105864 A1 | 5/2011 | Robertson et al. |

| | | | | | | | |
|---|---|---|---|---|---|---|---|
| 2011/0124983 | A1 | 5/2011 | Kroll et al. | WO | WO2005011237 | 2/2005 | |
| 2011/0144470 | A1 | 6/2011 | Mazar et al. | WO | 2005024687 | 3/2005 | |
| 2011/0224912 | A1 | 9/2011 | Bhavaraju et al. | WO | WO 2005020023 | 3/2005 | |
| 2011/0230732 | A1 | 9/2011 | Edman et al. | WO | WO2005047837 | 5/2005 | |
| 2011/0279963 | A1 | 11/2011 | Kumar et al. | WO | WO2005051166 | 6/2005 | |
| 2012/0029309 | A1 | 2/2012 | Paquet et al. | WO | WO2005082436 | 9/2005 | |
| 2012/0062371 | A1 | 3/2012 | Radivojevic et al. | WO | WO2005110238 | 11/2005 | |
| 2012/0101396 | A1 | 4/2012 | Solosko et al. | WO | WO2006021932 | 3/2006 | |
| 2012/0197144 | A1 | 8/2012 | Christ et al. | WO | WO2006027586 | 3/2006 | |
| 2012/0265544 | A1 | 10/2012 | Hwang et al. | WO | WO2006035351 | 4/2006 | |
| 2012/0310070 | A1 | 12/2012 | Kumar et al. | WO | WO 2006055892 | 5/2006 | |
| 2012/0316413 | A1 | 12/2012 | Liu et al. | WO | WO 2006055956 | 5/2006 | |
| 2013/0030259 | A1 | 1/2013 | Thomsen et al. | WO | WO2006075016 | 7/2006 | |
| 2013/0060115 | A1 | 3/2013 | Gehman et al. | WO | 2006087696 | 8/2006 | |
| | | | | WO | WO2006100620 | 9/2006 | |

FOREIGN PATENT DOCUMENTS

| | | | | | |
|---|---|---|---|---|---|
| WO | WO 2006104843 | 10/2006 | | | |
| CN | 201076456 | 6/2008 | WO | WO2006109072 | 10/2006 |
| EP | 0344939 | 12/1989 | WO | WO 2006116718 | 11/2006 |
| EP | 1246356 | 10/2002 | WO | WO2006119345 | 11/2006 |
| EP | 1702553 | 9/2006 | WO | WO 2006127355 | 11/2006 |
| EP | 1789128 | 5/2007 | WO | WO 2007001724 | 1/2007 |
| EP | 2143369 | 1/2010 | WO | WO 2007001742 | 1/2007 |
| IL | 172917 | 6/2010 | WO | WO 2007013952 | 2/2007 |
| JP | 61017949 | 1/1986 | WO | WO 2007014084 | 2/2007 |
| JP | 61072712 | 4/1986 | WO | WO2007014527 | 2/2007 |
| JP | 05-228128 | 9/1993 | WO | WO 2007021496 | 2/2007 |
| JP | 10-14898 | 1/1998 | WO | WO 2007027660 | 3/2007 |
| JP | 2000-506410 | 5/2000 | WO | WO2007028035 | 3/2007 |
| JP | 2002-224053 | 8/2002 | WO | WO 2007028035 | 3/2007 |
| JP | 2002263185 | 9/2002 | WO | 2007036741 | 4/2007 |
| JP | 2002291684 | 10/2002 | WO | 2007036746 | 4/2007 |
| JP | 2004-7187 | 1/2004 | WO | WO2007036687 | 4/2007 |
| JP | 2004134384 | 4/2004 | WO | WO2007036741 | 4/2007 |
| JP | 2005-073886 | 3/2005 | WO | WO2007036746 | 4/2007 |
| JP | 2005-087552 | 4/2005 | WO | WO2007040878 | 4/2007 |
| JP | 2005-304880 | 4/2005 | WO | WO2007067054 | 6/2007 |
| JP | 2005-532841 | 11/2005 | WO | WO2007071180 | 6/2007 |
| JP | 2005-532849 | 11/2005 | WO | WO2007096810 | 8/2007 |
| JP | 2006006377 | 1/2006 | WO | WO2007101141 | 9/2007 |
| JP | 2006509574 | 3/2006 | WO | WO2007120946 | 10/2007 |
| JP | 2006-177699 | 7/2006 | WO | WO2011133799 | 10/2007 |
| JP | 2006-187611 | 7/2006 | WO | WO 2007127316 | 11/2007 |
| JP | 2006278091 | 10/2006 | WO | WO2007127879 | 11/2007 |
| JP | 2009-061236 | 3/2009 | WO | WO2007127945 | 11/2007 |
| KR | 20020015907 | 3/2002 | WO | WO2007128165 | 11/2007 |
| KR | 20020061744 | 7/2002 | WO | WO 2007130491 | 11/2007 |
| KR | 2006077523 | 7/2006 | WO | WO2007133526 | 11/2007 |
| KR | 927471 | 11/2009 | WO | WO2007143535 | 12/2007 |
| TW | 553735 | 9/2003 | WO | WO 2007149546 | 12/2007 |
| TW | 200724094 | 7/2007 | WO | WO 2008008281 | 1/2008 |
| WO | 8802237 | 4/1988 | WO | WO 2008030482 | 3/2008 |
| WO | WO8802237 | 4/1988 | WO | WO2008052136 | 5/2008 |
| WO | WO 8802237 | 4/1988 | WO | WO 2008063626 | 5/2008 |
| WO | WO9221307 | 12/1992 | WO | WO2008066617 | 6/2008 |
| WO | WO9308734 | 5/1993 | WO | WO2008076464 | 6/2008 |
| WO | WO9319667 | 10/1993 | WO | WO 2008089232 | 7/2008 |
| WO | WO9739963 | 10/1997 | WO | WO2008091683 | 7/2008 |
| WO | WO9843537 | 10/1998 | WO | WO 2008095183 | 8/2008 |
| WO | WO9959465 | 11/1999 | WO | WO2008097652 | 8/2008 |
| WO | WO0033246 | 6/2000 | WO | WO 2008101107 | 8/2008 |
| WO | WO0100085 | 1/2001 | WO | WO 2008112577 | 9/2008 |
| WO | WO 0147466 | 7/2001 | WO | WO 2008112578 | 9/2008 |
| WO | WO0174011 | 10/2001 | WO | 20080120156 | 10/2008 |
| WO | WO0180731 | 11/2001 | WO | WO2008133394 | 11/2008 |
| WO | WO 0245489 | 6/2002 | WO | WO2008134185 | 11/2008 |
| WO | WO02058330 | 7/2002 | WO | 2009001108 | 12/2008 |
| WO | WO02062276 | 8/2002 | WO | WO2008150633 | 12/2008 |
| WO | WO02087681 | 11/2002 | WO | WO2009001108 | 12/2008 |
| WO | WO03050643 | 6/2003 | WO | WO 2009006615 | 1/2009 |
| WO | WO03068061 | 8/2003 | WO | WO2009029453 | 3/2009 |
| WO | WO 2004014225 | 2/2004 | WO | WO2009036334 | 3/2009 |
| WO | WO2004019172 | 3/2004 | WO | WO2009051829 | 4/2009 |
| WO | WO2004039256 | 5/2004 | WO | WO2009051830 | 4/2009 |
| WO | WO2004066833 | 8/2004 | WO | WO2009063377 | 5/2009 |
| WO | WO2004066834 | 8/2004 | WO | WO2009081348 | 7/2009 |
| WO | WO2004068748 | 8/2004 | WO | WO2009111664 | 9/2009 |
| WO | WO2004068881 | 8/2004 | WO | WO 2009146082 | 12/2009 |
| WO | WO2004075751 | 9/2004 | WO | WO 2010000085 | 1/2010 |
| WO | WO2004109316 | 12/2004 | WO | WO2010009100 | 1/2010 |

| | | |
|---|---|---|
| WO | WO 2010011833 | 1/2010 |
| WO | 2010019778 | 2/2010 |
| WO | 2010057049 | 5/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |

OTHER PUBLICATIONS

ISFET—Ion Sensitive Field-Effect Transistor; Microsens S.A. pdf document. pp. 1-4.
Walkey, "MOSFET Struture and Processing"; 97.398* Physical Electronics Lecture 20; pp. 1-24.
Coury, L. "Conductance Measurement Part 1: Theory"; Current Separations, 18:3 (1999) p. 91-96.
Watson, et al., "Determination of the relationship between the pH and conductivity of gastric juice" Physiol Meas. 17 (1996) pp. 21-27.
Bohidar et al., "Dielectric Behavior of Gelatin Solutions and Gels" Colloid Polym Sci (1998) 276:81-86.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Fawaz et al., "Enhanced Telemetry System using CP-QPSK Band—Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Given Imaging, "Agile Patency Brochure" (2006) http://www.inclino.no/documents/AgilePatencyBrochure_Global_GMB-0118-01.pdf; 4pp.
ISFET—Ion Sensitive Field-Effect Transistor; Microsens S.A. pdf document. Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Kamada K., "Electrophoretic deposition assisted by soluble anode" Materials Letters 57 (2003) 2348-2351.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Roulstone, et al., "Studies on Polymer Latex Films: I. A study of latex film morphology" Polymer International 24 (1991) pp. 87-94.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First third party client search conducted by Patent Eagle Search May 18, 2010 (2010).
"The SmartPill Wireless Motility Capsule" Smartpill, The Measure of GI Health; (2010) http://www.smartpillcorp.com/index.cfm?pagepath=Products/The_SmartPill_Capsule&id=17814.
Soper, S.A. et al. "Bio-Mems Technologies and Applications", Chapter 12, "MEMS for Drug Delivery", p. 325-346 (2007).
U.S. Appl. No. 12/238,345, filed Sep. 25, 2008, Hooman et al., Non-Final Office Action mailed Jun. 13, 2011 22pp.

Walkey, "MOSFET Struture and Processing"; 97.398* Physical Electronics Lecture 20; First Office Action dated Jun. 13, 2011 for U.S. Appl. No. 12/238,345; 24 pp.
Wongmanerod et al., "Determination of pore size distribution and surface area of thin porous silicon layers by spectroscopic ellipsometry" Applied Surface Science 172 (2001) 117-125.
"Smartlife awarded patent for knitted transducer" Innovation in Textiles News: http://www.innovationintextiles.com/articles/208.php; 2pp. (2009).
Description of ePatch Technology Platform for ECG and EMG, located it http://www.madebydelta.com/imported/images/DELTA_Web/documents/ME/ePatch_ECG_EMG.pdf, Dated Sep. 2, 2010.
Gaglani S. "Put Your Phone, or Skin, on Vibrate" MedGadget (2012) http://medgadget.com/2012/03/put-your-phone-or-skin-on-vibrate.html 8pp.
Rolison et al., "Electrically conductive oxide aerogels: new materials in electrochemistry" J. Mater. Chem. (2001) 1, 963-980.
AADE, "AADE 37th Annual Meeting San Antonio Aug. 4-7, 2010" American Association of Diabetes Educators (2010); http://www.diabeteseducator.org/annualmeeting/2010/index.html; 2 pp.
Juvenile Diabetes Research Foundation International (JDRF), "Artificial Pancreas Project" (2010); http://www.artificialpancreasproject.com/; 3 pp.
Lifescan, "OneTouch UltraLink™" http://www.lifescan.com/products/meters/ultralink (N.D.) 2 pp.
Medtronic, "CareLink Therapy Management Software for Diabetes" (2010); https://carelink.minimed.com/patient/entry.jsp?bhcp=1; 1 pp.
Medtronic, "Carelink™ USB" (n.d.) http://www.medtronicdiabetes.com/pdf/carelink_usb_factsheet.pdf 2pp.
Medtronic, "The New MiniMed Paradigm® Real-Time Revel™ System" http://www.medtronicdiabetes.com/products/index.html; 2 pp.
Medtronic, "Mini Med Paradigm® Revel™ Insulin Pump" (n. d.) http://www.medtronicdiabetes.com/products/insulinpumps/indexhtml; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Park, "Medtronic to Buy MiniMed for $3.7 Billion" (2001) HomeCare; http://homecaremag.com/mag/medical_medtronic_buy_minimed/; 2 pp.
Gilson, D.R. "Molecular dynamics simulation of dipole interactions", Department of Physics, Hull University, Dec. 2002, p. 1-43.
Li, P-Y, et al. "An electrochemical intraocular drug delivery device", Sensors and Actuators A 143 (2008) p. 41-48.
NPL_AntennaBasics.pdf, p. 1-3.
Santini, J.T. et al, "Microchips as controlled drug delivery-devices", Agnew. Chem. Int. Ed. 2000, vol. 39, p. 2396-2407.
Shawgo, R.S. et al. "BioMEMS from drug delivery", Current Opinion in Solid State and Material Science 6 (2002), p. 329-334.
Soper, S.A. et al. "Bio-Mems Technologies and Applications", Chapter 12, "MEMS for Drug Delivery", p. 325-346.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Arshak et al., A Review and Adaptation of Methods of Object Tracking to Telemetry Capsules IC-Med (2007) vol. 1, No. 1, Issue 1, pp. 35 of 46.
"ASGE Technology Status Evaluation Report: wireless capsule endoscopy" American Soc. For Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.

Delvaux et al., "Capsule endoscopy: Technique and indications" Clinical Gastroenterology (2008) vol. 22, Issue 5, pp. 813-837.

Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.) 4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Heydari et al., "Analysis of the PLL jitter due to power/ground and substrate noise"; IEEE Transactions on Circuits and Systems (2004) 51(12): 2404-16.

Intromedic, MicroCam Innovative Capsule Endoscope Pamphlet. 8 pp (http://www.intromedic.com/en/product/productinfo.asp).

MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

MacKay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Melanson, "Walkers swallow RFID pills for science" Engadget (2008); http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. Mini Mitter.com Mar. 31, 2009.

Mini Mitter Co, Inc. 510(k) Premarket Notification Mini-Logger for Diagnostic.Spirometer. Sep. 21, 1999.

Mini Mitter Co, Inc. 510(k) Premarket Notification for VitalSense. Apr. 22, 2004.

Minimitter Co. Inc. VitalSense Integrated Physiological Monitoring System. Product Description.

Minimitter Co. Inc. VitalSense Wireless Vital Signs Monitoring. Temperatures.com Mar. 31, 2009.

Mohaverian et al., "Estimation of gastric residence time of the Heidelberg capsule in humans: effect of varying food composition" Gastroenterology (1985) 89:(2): 392-7.

"New 'smart pill' to track adherence" E-Health-Insider (2010) http://www.e-health-insider.com/news/5910/new_'smart_pill'_monitors_medicines.

Philips Respironics (http/minimitter.com/products.cfm) Products, Noninvasive Technology to Help Your Studies Succeed. 510(k) Permanent Notification for Vital Sense. Apr. 22, 2004.

"RFID "pill" monitors marchers" RFID News (2008) http://www.rfidnews.org/2008/07/23/rfid-pill-monitors-marchers/.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

"SensiVida minimally invasive clinical systems" Investor Presentation Oct. 2009 28pp; http://www.sensividamedtech.com/SensiVidaGeneralOctober09.pdf.

Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.

"The SmartPill Wireless Motility Capsule" Smartpill, The Measure of GI Health; http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal Apr. 27, 2010; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

University of Florida News "Rx for health: Engineers design pill that signals it has been swallowed" (2010) 2pp.; http://news.ufl.edu/2010/03/31/antenna-pill-2/.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Zworkin, "A Radio Pill" Nature, (1957) 898, 179 Nature Publishing Group.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Owano, N., "Study proposes smart sutures with sensors for wounds" Phys.Org. Aug. 2012. http://phys.org/news/2012-08-smart-sutures-sensors-wounds.html.

Platt, D., "Modulation and Deviation" AE6EO, Foothills Amateur Radio Society; Oct. 26, 2007; 61 pp.

Halthion Medical Technologies "Providing Ambulatory Medical Devices Which Monitor, Measure and Record" webpage. Online website: http://www.halthion.com/; downloaded May 30, 2012.

Jimbo et al., "Gastric-fluid-utilized micro battery for micro medical devices" The Sixth International Workshop on Micro and Nanotechnology for Power Geneartion and Energy Conservation Applications, (2006) pp. 97-100.

"PALO Bluetooth Baseband" PALO Bluetooth Resource Center (2002) Retrieved from internet Dec. 12, 2012 at URL: http://palowireless.com/bluearticles/baseband.asp: first cited in Office Action dated Jan. 17, 2013 for EP08853901.0.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm The Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

B
⊗

B
⊗

IMPLANTABLE ZERO-WIRE COMMUNICATIONS SYSTEM

CROSS-REFERENCE TO RELATED APPLICATIONS

Pursuant to 35 U.S.C. §119 (e), this application claims priority to the filing date of: U.S. Provisional Patent Application Ser. No. 60/713,881 filed Sep. 1, 2005; U.S. Provisional Patent Application Ser. No. 60/713,680 filed Sep. 1, 2005 and U.S. Provisional Patent Application Ser. No. 60/739,174 filed Nov. 23, 2005; the disclosures of which applications are herein incorporated by reference.

INTRODUCTION

1. Field of the Invention

The present invention relates to medical apparatuses and methods, and in particular to methods and apparatuses for communicating information wirelessly within an organism, such as a patient.

2. Background of the Invention

Pacemakers and other implantable medical devices find wide-spread use in today's health care system. A typical pacemaker includes stimulating electrodes that are placed in contact with heart muscle, detection electrodes placed to detect movement of the heart muscle, and control circuitry for operating the stimulating electrodes based on signals received from the detection electrodes. Thus, the pacemaker can detect abnormal (e.g., irregular) movement and deliver electrical pulses to the heart to restore normal movement.

In most pacemakers in use today, the control circuitry is contained within a "can," a small device that is implanted in the chest near the heart. The can typically also includes radio frequency (RF) transmitting and/or receiving circuits that enable communication between the can and an external device such as a conventional pacemaker control "wand." A physician can obtain data from the pacemaker and/or reprogram its control settings by operating the external device. Pacemakers generally transmit and receive data in a frequency band of the electromagnetic spectrum at around 405 MHz, a band designated by federal regulations for medical device use.

A variety of other implantable or ingestible medical devices are also known in the art. Such devices include sensors that collect information about the structure and/or functioning of a patient's organs. For instance, ingestible capsules capable of imaging the patient's gastrointestinal tract are known. Other devices, such as neural stimulators used to treat back pain and related ailments, can affect physiological activity, e.g., by delivering electrical pulses. Some ingestible or implantable devices can communicate in real time with external devices. For instance, some such devices include magnetic induction coils that allow physicians to detect the position of the device within the patient's body at a given time using appropriate external sensors; the operating principle is similar to that of RFID tags. Other devices include RF transmitters and/or receivers similar to those used in pacemakers.

In order to generate a signal strong enough to be detected externally, RF-capable medical devices require milliwatts of power and relatively long antennas (usually at least several centimeters). These requirements place a lower bound on the size of the devices, making them impractical for many applications.

Thus, it would be desirable to provide alternative techniques for communicating with an implantable medical device.

SUMMARY

The present invention allows, for the first time, an implantable system that can be made up of conveniently small communications devices which nonetheless effectively communicate with each other in the body. Accordingly, an implantable communications platform is provided which is amenable to a multitude of different applications, including both diagnostic and therapeutic applications. The small size of the individual components of the system in accordance with embodiments of the invention and the ability of the components to effectively communicate wirelessly with each other through the body enables a number of different applications not heretofore possible.

According to one aspect of the present invention, a platform for communicating information within the body of a patient includes a first device and a second device. The first device includes a transmitter configured to transmit power and/or information via a quasi electrostatic coupling to the body of the patient. The second device includes a receiver configured to receive the transmitted power and/or information via a quasi electrostatic coupling to the body of the patient. The transmission frequency is selected such that the corresponding wavelength is significantly larger than the patient's body. For instance, a frequency of 100 kHz corresponds to a wavelength of 300 meters, over 100 times longer than the height of a typical human patient. In certain embodiments, the frequency is chosen to provide a wavelength that is more than 10 times longer, such as more than 50 time longer, including more than 100 times longer, than a largest dimension, e.g., height, of the body of the patient of interest, Where the first device transmits information, the second device may also be configured to retransmit the information to a location external to the body of the patient, e.g., via RF signaling to an external wand, or internal to the patient, e.g., an internal receiver.

According to another aspect of the present invention, a communications device for use within a body of a patient includes a power supply, a signal generating circuit, and an antenna. The signal generating circuit is coupled to the power supply and is configured to generate a signal. The antenna is coupled to the signal generating circuit and is configured to transmit the signal via quasi electrostatic coupling to the body of the patient.

According to still another aspect of the present invention, a method for communicating information within a body of a patient is provided. A transmitter unit is disposed within a body of the patient such that an antenna of the transmitter unit is in contact with the body. The transmitter is operated to generate a quasi electrostatic signal, and the quasi electrostatic signal is detected using a receiver. The receiver is advantageously at least partially internal to the patient's body.

Additional aspects of the invention include fluid flow sensors which may be present on one or more of the devices of the above described systems, or present on other platforms, such as lead platforms, e.g., multiplex leads.

The following detailed description together with the accompanying drawings will provide a better understanding of the nature and advantages of the present invention.

DETAILED DESCRIPTION

As summarized above, the present invention provides implantable systems that communicate wirelessly with each other (e.g., one-way or two-way) using a unique format that enables devices configurations and applications heretofore not possible. Embodiments of the present invention provide communication apparatuses and methods for exchanging information with implantable medical devices. In some embodiments, two implantable devices communicate with each other using quasi-electrostatic signal transmission in a long wavelength/low frequency electromagnetic band, with the patient's body acting as a conductive medium. In one embodiment, the signals have a frequency of about 100 kHz, wavelength on the order of 300 meters. One of the devices can be equipped with additional RF circuitry for communicating with an external device such as a conventional wand. Alternatively, one of the devices can be an external device that includes electrodes capable of detecting and/or generating quasi-electrostatic signals through the patient's skin.

I. Platform Overview

Figure 1:
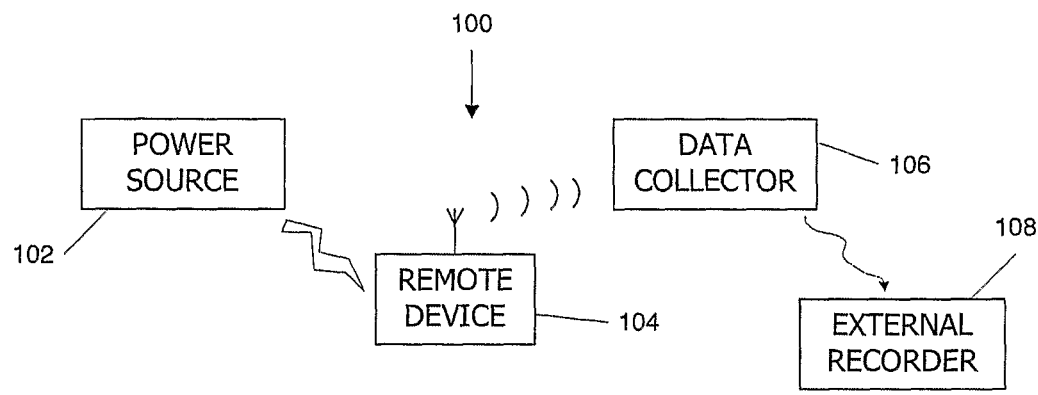
FIG. 1 is a block diagram of a medical diagnostic and/or treatment platform according to an embodiment of the present invention.

FIG. 1 is a block diagram of a medical diagnostic and/or treatment platform 100 according to an embodiment of the present invention. Platform 100 includes a power source 102, a remote device 104, a data collector 106, and an external recorder 108. In operation, remote device 104 is placed inside a patient's body (e.g., ingested or implanted) and receives power from power source 102, which may be located inside or outside the patient's body.

Remote device 104, described further in Section II below, is an electronic, mechanical, or electromechanical device that may include any combination of sensor, effector and/or transmitter units. A sensor unit (Section II.A) detects and measures various parameters related to the physiological state of a patient in whom remote device 104 is implanted. An effector unit (Section II.B) performs an action affecting some aspect of the patient's body or physiological processes under control of a sensor unit in the remote device or an external controller. A transmitter unit (Section II.C) transmits signals, including, e.g., measurement data from a sensor unit or other signals indicating effector activity or merely presence of the remote device, to data collector 106. In certain embodiments, transmission is performed wirelessly.

Power source 102, described further in Section III below, can include any source of electrical power that can be delivered to remote device 104. In some embodiments, power source 102 may be a battery or similar self-contained power source incorporated into remote device 104. In other embodiments, power source 102 is external to the patient's body and delivers power wirelessly (see, e.g., Section III.A).

Data collector 106, described further in Section IV below, may be implanted in the patient or external and connected to the patient's skin. Data collector 106 includes a receiver antenna that detects signals from a transmitter unit in remote device 104 and control logic configured to store, process, and/or retransmit the received information. In embodiments where remote device 104 does not include a transmitter, data collector 106 may be omitted.

External recorder 108 may be implemented using any device that makes the collected data and related information (e.g., results of processing activity in data collector 106) accessible to a practitioner. In some embodiments, data collector 106 includes an external component that can be read directly by a patient or health care practitioner or communicably connected to a computer that reads the stored data, and that external component serves as external recorder 108. In other embodiments, external recorder 108 may be a device such as a conventional pacemaker wand that communicates with an internal pacemaker can or other data collector, e.g., using RF coupling in the 405-MHz band. Communication between data collector 106 and an external device is described in Section IV below.

Figure 2:
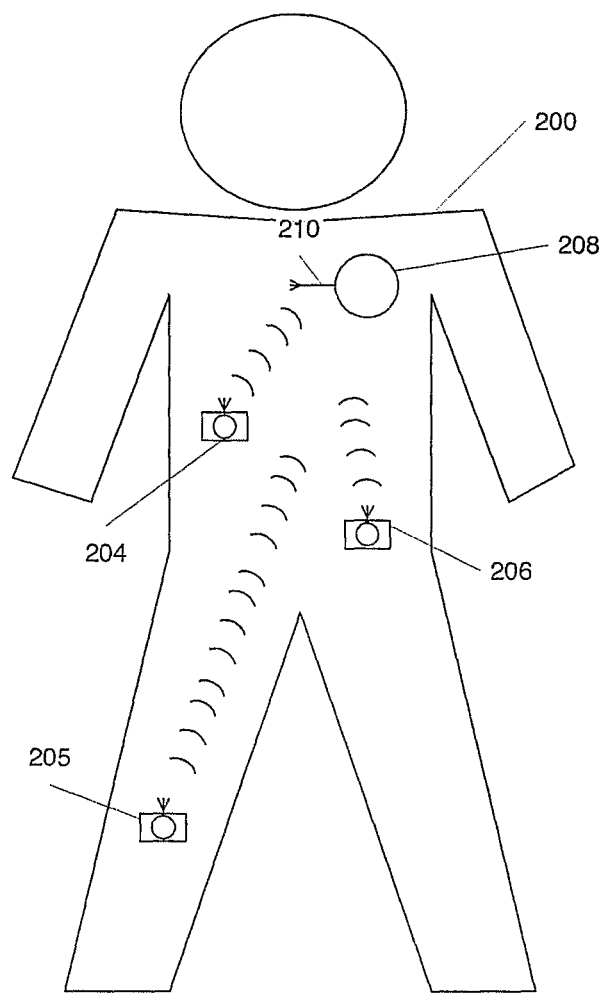
FIG. 2 shows a patient with multiple remote devices implanted at various locations in his or her body according to an embodiment of the present invention.

Platform 100 can include any number of power sources 102 and remote devices 104, which may be viewed as implantable medical devices. In some embodiments, a sensor/effector network (system) can be produced within the patient's body to perform various diagnostic and/or treatment activities for the patient. For instance, FIG. 2 shows a patient 200 with multiple remote devices 204, 205, 206 implanted at various locations in his (or her) body. Remote devices 204, 205, 206 might be multiple instances of the same device, allowing local variations in a parameter to be measured and/or various actions to be performed locally. Alternatively, remote devices 204, 205, 206 might be different devices including any combination of sensors, effectors, and transmitters. In certain embodiments, each device is configured to at least one of: (i) transmit a signal via a quasi electrostatic coupling to the body of the patient; and (ii) receive the transmitted signal via a quasi electrostatic coupling to the body of the patient. The number of remote devices in a given system may vary, and may be 2 or more, 3 or more, 5 or more, about 10 or more, about 25 or more, about 50 or more, etc. A data collector 208 is equipped with an antenna 210 and detects the signals transmitted by remote devices 204, 205, 206. Since the remote devices advantageously transmit signals wirelessly, applications of the platform are not limited by the difficulty of running wires through a patient's body. Instead, as will become apparent, the number and placement of remote devices in a patient's body is limited only by the ability to produce devices on a scale that can be implanted in a desired location. Specific examples of sensor networks are described in Sections V and VI below.

The following discussion is provided with reference to a patient. As used herein, the term "patient" refers to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

II. Remote Device

As used herein, a "remote device" includes any electronic, electromechanical, or mechanical device that can enter a patient's body, e.g., via implantation or ingestion, and perform some activity with diagnostic and/or therapeutic significance while inside the body. In certain embodiments, a remote device does not require a wired connection to any other device located elsewhere inside or outside of the body.

A remote device can be located anywhere in the body, provided it is suitably sized, shaped and configured to operate without disrupting a desirable physiological function. Examples of areas in which remote devices may be located include but are not limited to inside or outside the gastrointestinal tract, inside or outside the urinary tract, inside or outside a reproductive tract, inside or outside blood vessels, inside or outside various organs (e.g., heart, brain, stomach, etc.), at or near surgical sites or wound locations, at or near a tumor site, within the abdominal cavity, in or near joints, and so on.

Within the scope of the present invention, different embodiments of a remote device may perform different actions. For purposes of the present description, these actions are characterized as different "units" within a remote device: sensors, which measure some aspect of physiological function; effectors, which perform an action affecting some aspect of physiological function; and transmitters, which transmit information from the remote device to a data collector. The following sections describe examples of each type of unit. It is to be understood that a given embodiment of a remote device may include any combination of these units and any number of instances of one type of unit.

For instance, a first class of remote devices includes a sensor unit coupled with a transmitter unit. The sensor measures some physiologically relevant parameter, and the transmitter transmits the measurement to a data collector for further use. A second class of remote devices includes an effector unit which is actuated in response to a received signal, e.g., either from a sensor present on the device and/or from a remote unit. In certain of these classes of devices, the device includes a sensor unit coupled to an effector unit. The sensor measures some physiologically relevant parameter, and the effector unit is actuated (or not) based on the sensor measurement. In some embodiments in this class, a transmitter unit is also included and may transmit sensor data and/or signals indicating activity of the effector unit. A third class of remote devices includes an effector unit that is actuated whenever power is provided by the power source (see FIG. 1). In this class of embodiments, the power source might be under the control of a physician or the patient, or it might be controlled by a data collector that receives signals from a sensor in a different remote unit elsewhere in the patient's body and determines, based on the received sensor signals, whether to actuate the effector. Some embodiments in this class may also include a transmitter that generates signals indicating, e.g., the presence of the effector or whether the effector is in operation at a given time. A fourth class of remote devices includes only a transmitter that generates a signal (e.g., an identification signal) whenever power is provided by the power source (see FIG. 1). An example embodiment in this class is described in Section V.A below.

A. Sensors

As used herein, a "sensor" (or "sensor unit") includes any component of a remote device that is capable of measuring a property relevant to physiological function of the body. (The measurement is referred to herein as "data.") A sensor may transmit the data to a suitable data collector, or it may control operation of an associated effector unit in the same remote device based on the data, or it may do both of these. Examples of sensor units include but are not limited to the following:

(1) A fluid flow sensor. One embodiment of sensors that may be employed in the present invention is a fluid flow sensor, where such sensors measure a parameter of fluid flow of a physiological fluid. While in general sensors may be configured to determine a parameter of fluid flow of any of a variety of different physiological fluids, of interest in certain embodiments are sensors configured to determine a parameter of blood flow. Accordingly, for ease of description the fluid flow sensor embodiments of the invention are further described primarily in terms of blood flow sensors.

As such, one embodiment of the present invention relates to a blood flow sensor that can measure flow velocity and/or hematocrit (the percentage, by volume, of the patient's blood that is made up of red blood cells). These measurements can be used to detect various physiological conditions. For instance, "stroke volume"—i.e., the volume of blood flowing into or out of the heart per cardiac cycle—can be determined by measuring blood flow velocity in an artery (e.g., the aorta) or vein (e.g., the vena cava) and using the cross-sectional area of the blood vessel and duration of the cardiac cycle to compute stroke volume. As another example, circulatory problems (e.g., blockages) can also be detected through blood flow measurements. Localized changes in physiological activity (e.g., digestion, brain activity, tumor growth or shrinkage, and so on) can be detected by changes in blood flow in the relevant region of the body, since body systems require more oxygen (and hence greater blood flow) when they are more active. Any of these or other uses can be made of blood flow data, and the particular application for which a sensor is employed is not relevant to the present invention.

In one embodiment, a blood-flow sensor is a resistive blood flow sensor. In another embodiment, a blood-flow sensor is an electromagnetic blood flow sensor.

(2) Pressure sensor. One embodiment of the present invention relates to a pressure sensor that can detect pressure or changes in pressure at some location inside the body. Pressure sensors can be implemented using, e.g., piezoelectric crystals, which generate an electrical charge when deformed as is known in the art. The electrical charge can be collected and measured. In some embodiments, a pressure sensor includes a compliant member (e.g., a planar structure) mounted on a substrate. The compliant member has two exposed surfaces, and a strain transducer (which may be, e.g., a piezoelectric transducer) is mounted on or indirectly attached to one of the exposed surfaces. The transducer generates an electrical signal in response to deformation of the compliant member resulting from pressure changes. In these embodiments, the pressure sensor can be implemented with low drift, so as to provide stable readings over an extended period. Examples of pressure sensors that may be used in embodiments of the present invention include, but are not limited to, those described in U.S. Pat. Nos. 7,073,387; 7,066,031; 7,028,550; 7,013,734 and 7,007,551; the disclosures of which are herein incorporated by reference. Other types of pressure sensors may also be used.

In some embodiments, the sensor simply registers the presence or absence of a pressure change; in other embodiments, the sensor quantifies the pressure change, e.g., by determining the amount of charge collected, the amount of current or potential difference, or the like. Pressure sensors have numerous uses. For example, the heart regularly expands and contracts, and the changing-pressure on a pressure-sensor can be used to measure the movement of the heart. Blood pressure can also be measured. In addition, any other muscle movements can be detected using suitably placed pressure sensors, including but not limited to stomach and intestinal contractions, uterine contractions (e.g., during pregnancy), muscle spasms, and so on. Pressure sensors placed at a tumor site can also be used to measure the growth or shrinkage of a tumor: as the tumor grows, its pressure on surrounding tissues increases, and as it shrinks, the pressure decreases.

(3) Chemical properties and composition. Additional embodiments of the present invention relate to sensors designed to detect chemical properties and/or composition of substances in the body (e.g., blood, gastric fluids, and so on). One category of chemical sensors relates to general chemical properties such as pH. Other categories of chemical sensors relate to detecting the presence, absence or concentration of specific substances. For instance, oxygen, carbon dioxide, glucose, enzymes, clotting factors in blood, antibodies, bacteria, cancer markers, and so on can all be detected using suitably configured sensors. In one embodiment, antibodies can be detected by designing a nanoscale sensor with a nanotube to which a receptor molecule for the antibody is attached. The sensor is arranged such that when the antibody binds to the receptor molecule, current flows in the nanotube and is detected. Examples of such sensors are known in the art and may be employed in embodiments of the invention.

Chemical sensors have a wide array of applications. For instance, in a diabetic patient, if a sensor detects an unacceptably high glucose level, it can actuate an effector that releases insulin into the patient's body, or it can transmit a signal via a data collector to an external device that advises the patient to inject insulin. Sensors configured to detect antibodies and/or bacteria might be used at surgical or wound sites to detect infection before the signs become apparent to an external observer. Sensors configured to detect cancer markers could be implanted in cancer survivors or high-risk patients to facilitate early detection of recurrence or initial onset. Many other applications will be apparent to those of ordinary skill in the art with access to the present disclosure.

(4) Electrical properties. Another embodiment of the present invention relates to electrical properties, such as conductivity, resistivity, electrical potential, etc. In some instances, these properties are used as indirect measurements of physiological parameters; for instance, the resistivity of blood can be used to determine flow rate as described above. In other embodiments, electrical properties can be used for "electrical tomography," measuring positions and/or displacements of the heart or other structures in the body. In one such system, three (or more) electrodes are used, with at least one being intracardiac (i.e., implanted within the heart) and the others ("field electrodes") being positioned in areas that are relatively stationary (i.e., that do not move with the heart). An electrical field is generated between the field electrodes, and the intracardiac electrode senses the amplitude of the electrical field. As the intracardiac electrode is moved relative to the field electrodes by the contractions of the heart, the sensing electrode moves within the electric field, and the sensed potential varies. From these variations, information about cardiac function, including contractile magnitude and timing can be derived and used for diagnostic and/or therapeutic purposes. Examples of continuous field, including electrical, tomography systems and methods are described in pending application no. PCT/US2005/036035 published as WO 2006/042039, the disclosure of which including priority applications thereof is incorporated by reference.

In other embodiments, e.g., with application in neurology, electrical properties may be directly of interest. For instance, nerve function in repetitive stress injury (RSI) patients can be monitored to determine whether various therapies are improving or aggravating the condition.

(5) Thermal properties. Still another embodiment of the present invention relates to thermal properties such as temperature, thermal conductivity and so on. Microscale or smaller thermoelectric devices can be made using techniques known the art and implanted in the body at various sites. Temperature changes or absolute temperature measurements can be used to identify increased physiological activity in some tissue, organ or system (e.g., blood flow and therefore temperature in the GI tract generally increase during digestion). At a wound site or surgical site, a localized temperature increase could also be detected and recognized as a sign of possible infection.

(6) Radiation exposure. Another embodiment relates to sensing radiation exposure in some tissue. Radiation sensors may be implanted into tumor sites and/or surrounding tissues during radiation therapy; readout from the sensors can provide real-time information as to whether the radiation is being delivered to the intended target or to healthy tissue, allowing the delivery system to be adjusted.

Sensors of interest further include, but are not limited to, those sensors described in the following applications by at least some of the inventors of the present application: U.S. patent application Ser. Nos. 10/734,490 and 11/219,305; International Application No. PCT/US2005/046815; U.S. patent application Ser. No. 11/324,196; U.S. patent application Ser. No. 10/764,429; U.S. patent application Ser. No.

10/764,127; U.S. patent application Ser. No. 10/764,125; International Application No. PCT/US2005/046815; U.S. application Ser. No. 11/368,259; International Application No. PCT/US2004/041430; U.S. patent application Ser. No. 11/249,152; and International Application Serial No. PCT/USUS05/39535. These applications are incorporated in their entirety by reference herein.

It will be appreciated that the foregoing list is illustrative and that sensors within the scope of the present invention may be configured to monitor any property of interest, including but not limited to optical properties (e.g., remote cameras, wireless laparoscopes, etc.), mechanical properties (e.g., strain on a muscle or tendon), dimensions or volume properties, electrical conductivity data, electrical potential data, thermal conductivity data, viscosity data, and the like.

B. Effectors

Figure 3:
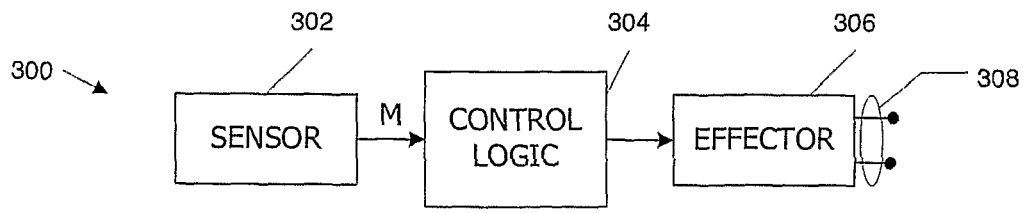
FIG. 3 shows a remote device that includes an effector unit configured to deliver electrical stimulation to a patient's tissue according to an embodiment of the present invention.

As used herein, an "effector" (or "effector unit") includes any component of a remote device that is capable of performing, in response to a control signal, an action affecting some aspect of the patient's physiological function. In some embodiments, the control signal is generated by a sensor unit on the same remote device. For instance, FIG. 3 shows a remote device 300 that includes a sensor 302, control logic 304 (e.g., in the firm of circuitry/hardware and/or software implementation), and an effector 306 that includes in this instance electrodes 308 placed in contact with the patient's tissue (not shown) so as to be able to deliver an electrical stimulation (e.g., current or voltage pulse) to the tissue. It is to be understood that an effector might perform functions other than electrical stimulation (some examples are described below), and accordingly not all effectors would include stimulating electrodes as shown in FIG. 3.

In operation, when power is applied to remote device 300, sensor 302 performs a measurement of a physiological parameter (or a quantity such as resistivity that relates to a physical parameter) and provides the measurement result (M) to control logic 304. Control logic 304 processes the result M to determine whether effector 306 should be actuated. If so, control logic 304 sends an activation signal on line 310 to effector 306, which operates electrodes 308 to apply a stimulus to the patient's tissue. The activation signal can be a binary (on/off) signal, or it may have multiple levels, e.g., the intensity of the stimulation. The duration of stimulation can also be varied in response to the control signal.

In other embodiments, the effector receives a control signal wirelessly from some other implanted or external device. For example, a sensor located in one place in the body may transmit a signal wirelessly (e.g., as described below) to an effector located elsewhere. This configuration may be useful in situations where the optimal location for detecting occurrence a physiological condition is different from the optimal location for applying a treatment.

Figure 4:
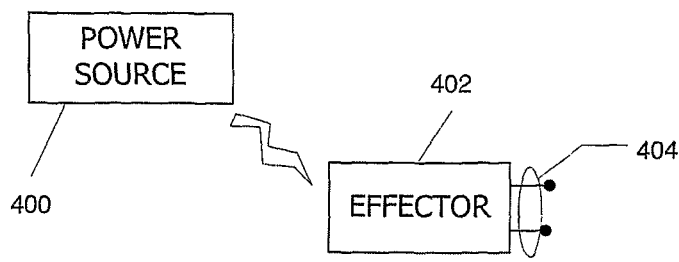
FIG. 4 shows a power source adapted for wireless power delivery according to an embodiment of the present invention.

In still other embodiments, the effector operates whenever it receives sufficient power, and application of power to the effector serves as a control signal. For instance, FIG. 4 shows a power source 400 that delivers power wirelessly (e.g., as described in Section III.A below) to an effector 402. Whenever effector 402 has sufficient power to operate electrodes 404, it does so. (Again, it is to be understood that stimulating electrodes are used for purposes of illustration and are not limiting of the scope of the invention.)

In some embodiments, an effector can also be paired with a transmitter unit that transmits an identification signal and/or a signal carrying information about operation of the effector (e.g., when the effector is actuated, at what level the effector is actuated, etc.). Examples of effector units include but are not limited to:

(1) Drug delivery. One embodiment of an effector includes a chamber that is filled with a drug (i.e., any pharmacologically active substance) and a mechanism for releasing or ejecting the drug from the chamber into the patient's body in response to a control signal. The drug can be released in controlled dose sizes, and the effector may be loaded with multiple doses. For instance, the effector might be filled with insulin and coupled to a sensor that measures a glucose level in the blood. When the glucose level rises above some threshold, the effector is actuated and delivers a dose of insulin. Other materials (e.g., chemical and/or neurological elating materials) can be similarly delivered through an implanted remote effector.

(2) Electrical stimulation. Another embodiment of an effector includes electrodes that can be controllably charged to deliver an electrical stimulation (current and/or voltage) to a desired point in the body in response to a control signal. Such electrical stimulation may be used, e.g., to initiate or counteract contractions of a muscle, to stimulate nerves for therapeutic or diagnostic purposes (e.g., to prevent or detect nerve damage in a particular area or nerve), for cardiac defibrillation, and so on.

(3) Mechanical stimulation or manipulation. Another embodiment of an effector includes deformable or moveable parts that can apply mechanical stimulation or pressure to a desired area. For example, piezoelectric crystals that deform when a current is applied can be used to apply pressure to a blood vessel or muscle, to manipulate various organs, etc. In addition, the emerging technology of microscale or nanoscale robotic systems could be employed as effectors within the scope of the present invention.

(4) Temperature control. Another embodiment of an effector includes a heat source (e.g., a resistive element) that can generate heat when a current or voltage is applied. Such effectors can be used, e.g., in applying heat directly to an injured muscle to facilitate healing and so on.

(5) Capture of material. Another embodiment of an effector includes a chamber that is initially empty but that can be filled with material by activity of the effector. For instance, the effector might be ingested into the patient's digestive tract and actuated under some suitable conditions to open its chamber, allowing the chamber to be filled with a sample of the contents of the patient's stomach or intestine. The effector may be paired with a sensor that analyzes the contents in situ, or the effector may be in a capsule that passes through the digestive tract and is recovered for analysis after it exits the body.

(6) Radiation emission. Another embodiment of an effector includes a shielded radiation source and a mechanism for removing and replacing at least a portion of the shield in response to a control signal. Such an effector can be used to provide radiation for diagnostic or therapeutic purposes.

It will be appreciated that the foregoing list is illustrative and that effectors within the scope of the present invention may be configured to perform any type of operation for any diagnostic or therapeutic purpose. For instance, effectors may also perform actions such as setting an electrical potential, emitting light, emitting sonic or ultrasound energy, emitting radiation and the like.

C. Transmitter

As used herein, a "transmitter" (or "transmitter unit") in a remote device is a component that transmits signals through the body wirelessly using direct or near-field electrical coupling to the conductive tissues of the body. The signals carry some amount of information. Examples of information include, but are not limited to: a presence indicator (e.g., identification code) that indicates that the device is operational; a measurement value generated from a sensor unit in the remote device; a signal indicating occurrence of activity and/or level of activity of an effector unit in the remote device; a control signal that controls an effector located in a remote device elsewhere in the body; and so on. Any information related to the state or operation of the remote device can be formed into a signal and transmitted by the transmitter unit.

Figure 5:
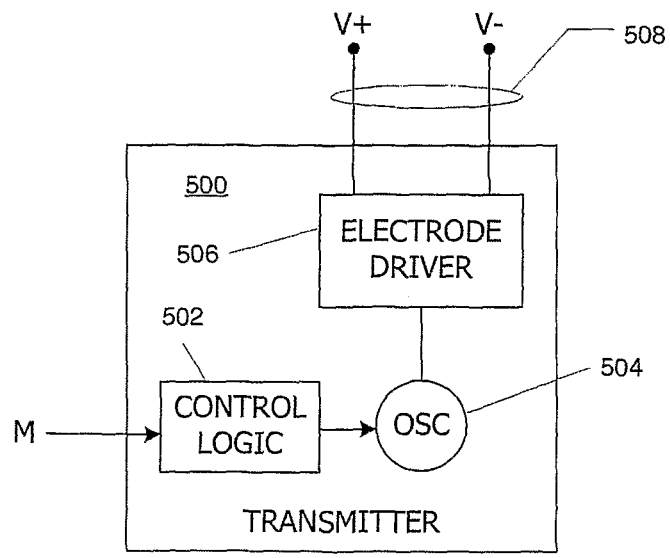
FIG. 5 is a block diagram of a transmitter unit for a remote device according to an embodiment of the present invention.

FIG. 5 is a block diagram of a transmitter 500 for a remote device according to an embodiment of the present invention. In this embodiment, transmitter 500 receives a signal M representing a measurement made by a sensor unit (not shown) of the remote device. Transmitter 500 includes control logic 502, an oscillator 504, an electrode driver 506, and an antenna 508 (in this instance, a pair of electrodes operated as an electric dipole antenna). In operation, oscillator 504 generates an oscillating signal (waveform) in response to signals from control logic 502. The signals from control logic 502 can start or stop the oscillator and in some embodiments can also shape one or more aspects of the oscillatory signal such as amplitude, frequency, and/or phase. Oscillator 504 provides the waveform to electrode driver 506, which drives current or voltage on antenna 508 to transmit a signal into the conductive medium of body tissues or fluids.

In certain embodiments, a "quasi-electrostatic" or "near-field" coupling protocol is used to transmit information, as described in Section 1. Section 2 describes examples of small antennas designed for near-field coupling, and Section 3 describes modulation techniques that can be used to encode information content in the transmitted signal.

1. Near-Field Transmission

As is known in the art (see, e.g., J. D. Jackson, *Classical Electrodynamics*, 2nd Edition, pp. 394-396 (1975)), the electric (E) and magnetic (B) fields for radiation of an oscillating electric dipole antenna with an angular frequency ω and corresponding wave number k (where k=ω/c, with c being the speed of light in the relevant medium) are given by the equations:

$$B = k^2 (n \times p) \frac{e^{ikr}}{r} \left(1 - \frac{1}{ikr}\right); \quad (1)$$

and $$E = k^2 (n \times p) \times n \frac{e^{ikr}}{r} + [3n(n \cdot p) - p]\left(\frac{1}{r^3} - \frac{ik}{r^2}\right)e^{ikr}, \quad (2)$$

where n is a unit vector in the direction from the center of the dipole source to a location x at a distance r from the source, and p is a space-integrated density of electric charge given by p=∫x'ρ(x')d³x'.

As can be seen from Eqs. (1) and (2), in the "far field" region, where r>>λ (where the wavelength λ=2π/k), the electric and magnetic fields are dominated by terms that decrease with distance as 1/r. In this region, mutually perpendicular electric and magnetic fields feed off one another to propagate the signal through space. Where λ~r, the 1/r² ("induction") terms in Eqs. (1) and (2) become significant, and where λ>>r, an additional quasi-electrostatic term that varies as 1/r³ also becomes significant.

Conventional RF communication takes place at distances r~λ to r>λ. For instance, implantable medical devices such as pacemakers typically communicate in the 405-MHz frequency band, corresponding to wavelengths of 0.75 meters, somewhat smaller than the scale of a human body. As is known in the art, higher frequencies are advantageously not used because structures within the body begin to absorb radiation, leading to undesirable signal loss; substantially lower frequencies (longer wavelengths) are generally regarded as undesirable because much of the energy is redirected into the induction and/or quasi-static field components rather than the far-field component that can be sensed using conventional antennas. It should also be noted that RFID applications with a transponder and a base unit typically use wavelengths such that r~λ and generally rely on magnetic induction to transmit power from the transponder to the base unit.

In contrast to these approaches, transmitter embodiments of the present invention advantageously operate at wavelengths much larger than the human body (λ>>1 meter) to communicate information within the patient's body. For instance, in some embodiments, frequencies on the order of 100 kHz, corresponding to wavelengths of around 3 km (in air), are advantageously used. At distances r that are short as compared to the wavelength λ, the quasi-static electric field term in Eqs. (1) and (2) dominates, and thus the propagating signal is predominantly electrical rather than electromagnetic. Such signals readily propagate in a conductive medium such as the human body. For instance, at a frequency of 100 kHz and distances on the order of 1-2 meters, the quasi-static (1/r³) component of Eq. (2) is estimated to be on the order of $10^6$ times stronger than the far-field (1/r) component. Thus, long-wavelength signaling using near-field coupling is efficient. Further, because the signals are required to travel relatively short distances (typically 2 meters or less), detectable signals can be transmitted using very small antennas.

A wide range of frequencies may be used for transmission of signals. In some embodiments, the transmission frequency is within the "LF" band (low frequency, defined as 30-300 kHz) of the RF spectrum, below the frequency range of AM radio (around 500 to 1700 kHz). Within the LF band, the range from 160-190 kHz has been designated by the FCC for experimental use, with specified upper limits on external signal strength. In embodiments of the present invention where the signals are largely confined within the patient's body as described below, this experimental band can be used.

However, the invention is not limited to the 160-190 kHz band or to the LF (30-300 kHz band). Lower bands may also be used; for instance, in the VLF band (3-30 kHz, wavelengths of 10-100 km in air), signals can penetrate water to a distance of 10-40 meters. Since the electrical properties of the human body are similar to those of salt water, signals in this band also readily propagate through the body and may be employed. Thus, any frequency band corresponding to a wavelength that is at least an order of magnitude larger than the human body—e.g., λ~10 m or longer, or frequencies on the order of 30 MHz or below—can be used.

While there is no necessary lower limit on the frequency of signals used, several practical considerations may affect into the choice of frequency. For instance, it is well known that the human body carries low-level oscillating signals induced by nearby AC-powered devices, which operate at 60 Hz (US) or similar frequencies in other parts of the world. To avoid interference caused by AC electrical power systems, frequencies near 60 Hz, such as from about 55 to about 65 Hz, are not used employed in certain embodiments. In addition, as is known in the art, longer wavelengths correlate with lower information transfer rates, and the information-transfer capacity at long wavelengths (e.g., below the 3 kHz-30 kHz VLF band) may be too small for the amount of information that is to be transferred in a particular system. Further, longer wavelengths generally require longer dipole antennas to produce a detectable signal, and at some point the antenna size may become a limiting factor in frequency selection.

According to some aspects of the invention, given a suitable choice of frequency, a signal strong enough to travel to a receiver within the body can be generated using a very small antenna. For instance, 100 kHz signals generated by a dipole antenna just a few millimeters long can be propagated to a receiver antenna placed 1-2 meters away. This quasi-electrostatic transmission is believed to be aided by the fact that the implanted antenna is directly in contact with a conductive medium, specifically, the patient's tissues. For purposes of analyzing electrical properties, human tissue can be approximated as an electrolyte solution with electrical properties comparable to those of salt water. Thus, as in an electrolyte bath, the quasi-electrostatic field created by an oscillating dipole antenna induces an oscillating current in the body. As a result of the inherent electrical resistivity of the body (comparable to salt water), the oscillating current creates oscillating potential variations within the body that can be sensed using a suitable receiver. (See, e.g., L. D. Landau et al., *Electrodynamics of Continuous Media*, Ch. 3 (1960)). Examples of suitable receivers include the leads of a pacemaker, which create a dipole with an axis of about 20 cm or any other implanted wires with length from about 10 to about 100 cm.

It should be noted that these currents are undesirable in the context of conventional RF communication, in which current flow in the near field leads to power loss in the far-field. In fact, many RF transmitters include devices designed to minimize near-field current leakage. In near-field transmitters of the present invention, maximizing such currents is desirable.

Further, for quasi-electrostatic signals, the patient's skin advantageously acts as a conductive barrier, confining the signals within the patient's body. This confines the signals within the body and also makes it difficult for stray external signals to penetrate the body and create noise or interference in the transmitted signals. Confinement of the signals can mitigate, to some extent, the $1/r^3$ falloff of the near-field signal, further reducing power requirements. Such effects have been observed in the laboratory, e.g., in a salt water bath, in which the water/air interface acting as a conductive barrier. Similar effects have been observed in communicating with submarines via RF transmission in the ELF (3-30 Hz) and SLF (30-300 Hz) bands. These effects have also been observed in sonar communications; although sonar uses acoustic, rather than electrical or electromagnetic, fields to transmit information, the surface of the water acts as a conductive barrier for acoustic energy and mitigates the fall-off of signal intensity with distance.

As a result of these phenomena, a transmitter with a very small antenna and a small power source are sufficient to create a near-field signal that is detectable within the patient's body. For instance, the antenna can be formed by a pair of electrodes a few millimeters or less in length, spaced apart by a few millimeters, with oscillating voltages of opposite phase applied to create an oscillating electric dipole. Such antennas can be disposed almost anywhere within the body.

Further, in some embodiments, the frequency, transmitter antenna length, and receiver antenna length are selected such that only microwatts of power are required to produce a detectable signal, where conventional RF communication (e.g., at around 405 MHz) would require at least milliwatts. Accordingly, very compact power supplies that produce only small amounts of power can be used; examples are described in Section IV below.

A quasi-electrostatic transmitter can be incorporated into various implantable or ingestible remote devices, either in combination with a sensor and/or an effector. A transmitter can also be configured as a remote device without a sensor or an effector; in this case, the transmitter transmits whenever power is supplied or when a control signal is received.

The transmitter may transmit any type of information desired. In some embodiments, the transmitter may simply act as a presence indicator, e.g., by transmitting a predefined identification signal. In other embodiments, the transmitter is incorporated into a sensor device and transmits sensor data in addition to or instead of an identification signal.

In addition, in some embodiments, the transmitter may also be operated as a receiver, e.g., to receive instructions for activating or deactivating an effector unit or sensor unit in the remote device of which the transmitter is a part. Such instructions may be transmitted using quasi-electrostatic near-field coupling as described above.

2. Antennas

Figure 6:
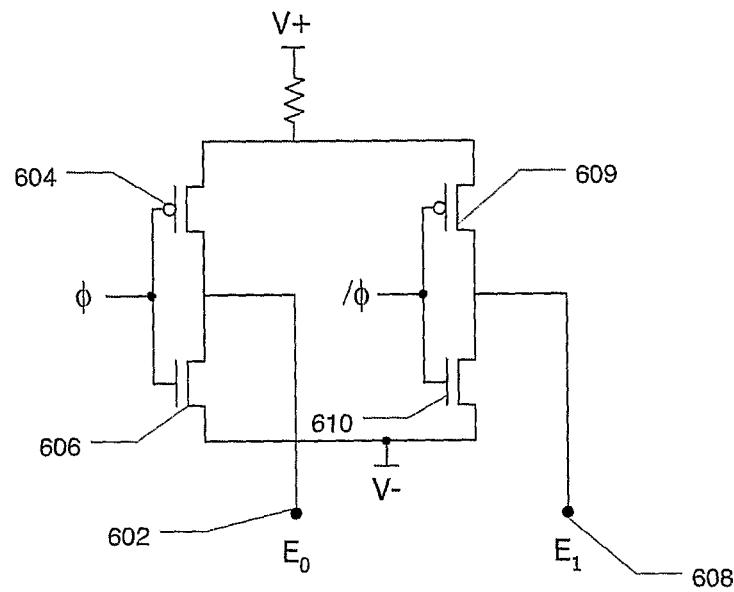
FIG. 6 is a circuit diagram showing details of a dipole electrode driver implemented using conventional CMOS driver circuits for use in a transmitter according to an embodiment of the present invention.

In some embodiments, the transmitter unit uses an electric dipole or electric monopole antenna to transmit signals. FIG. 5 (described above) illustrates a dipole antenna. Oscillator 504 provides driving signals ($\phi$ and an inverted signal denoted herein as /$\phi$) to an electrode driver 506. FIG. 6 is a circuit diagram showing details of a dipole electrode driver 600 implemented using conventional CMOS driver circuits. Electrode 602 is driven to a potential $E_0$ by transistors 604, 606 in response to driving signal $\phi$ while electrode 608 is driven to a potential $E_1$ by transistors 610, 612 in response to inverted driving signal /$\phi$. Since driving signals $\phi$ and /$\phi$ oscillate with opposite phase, potentials $E_0$ and $E_1$ also oscillate with opposite phase. It will be appreciated that driver 600 and all other electronic circuits described herein can be implemented using sub-micron CMOS processing technologies known in the art; thus, the size of the circuitry is not a limiting factor on the size of a remote device.

Figure 7:
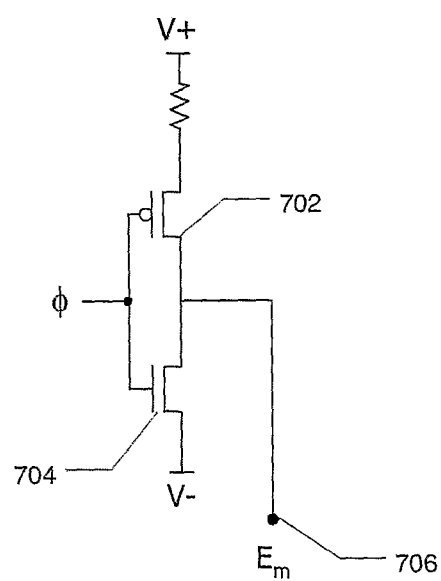
FIG. 7 illustrates a driver circuit for a monopole antenna that can be implemented in conventional CMOS integrated circuits for use in a transmitter according to an embodiment of the present invention.

In some embodiments, a monopole antenna can be substituted for the dipole antenna of FIG. 5. FIG. 7 illustrates a driver circuit for a monopole antenna that can be implemented in conventional CMOS integrated circuits. This antenna driver is generally similar to one half of the driver circuit of FIG. 6, with driver transistors 702, 704 driving a single electrode 706 to a potential $E_m$ in response to driving signal $\phi$.

In either the dipole or monopole case, the driver circuit is powered by a potential difference ($\Delta V$) between terminals V+ and V−. This potential difference, which can be constant or variable, as desired, is advantageously provided by a power source as described in Section III below.

3. Modulation Techniques

Referring again to FIG. 5, in some embodiments, oscillator 504 operates at a constant frequency. The receipt of a constant-frequency signal in and of itself can provide useful information, e.g., that a remote device is present and operational. In some embodiments, oscillator 504 modulates its signal to encode additional information.

Information can be encoded in various ways, generally by modulating (varying) some property of the transmitted signal, such as frequency, amplitude, phase, or any combination thereof. Modulation techniques known in the art may be employed.

In general, information can be transmitted using analog or digital techniques. "Analog techniques" refers generally to instances in which the modulated property is varied in different degrees, with the degree of variation being correlated to a value representing the information to be transmitted. For instance, suppose that transmitter 500 is transmitting a quantity M measured by an associated sensor in the remote device. Oscillator 504 can be designed to operate over some range of frequencies, with a minimum frequency corresponding to a minimum value of the quantity M and a maximum frequency corresponding to a maximum value of the quantity M; frequencies between the maximum and minimum values map to intermediate values of M (e.g., using linear interpolation, exponential interpolation, or the like).

"Digital techniques" refers generally to instances in which the information to be transmitted is represented as a sequence of binary digits (bits), and the signal is modulated based on the bit stream. For instance, suppose again that transmitter 500 is transmitting a quantity M measured by an associated sensor in the remote device, but using digital techniques. Oscillator 504 can be designed to operate at least two different frequencies with one frequency corresponding to bit value 0 and another frequency corresponding to bit value 1.

In embodiments of the present invention, either analog techniques, digital techniques, or a combination thereof can be used to transmit information. In addition, various types of modulation may be implemented.

For instance, in one embodiment, frequency modulation is used. Oscillator 504 can be a voltage-controlled oscillator (VCO), a well-known oscillator circuit in which the oscillation frequency depends on an applied voltage. Control logic 502 supplies an appropriate voltage (e.g., reflecting the value of the measurement data, M), and the frequency of the signal indicates the value of the data.

In another embodiment, amplitude modulation is used; for instance, the amplitude of the driving signals $\phi$ and $/\phi$ can be varied, or the positive and negative rails of the driver circuit (V+ and V− in FIGS. 6 and 7) can be varied to control the amplitude.

In another embodiment, phase modulation is used. For instance, in digital signal transmission, one phase corresponds to bit value 0, an opposite phase corresponds to bit value 1, and the phase shifts represent transitions. Oscillator 504 can include a switch circuit that either directly connects or cross-connects the driving signals $\phi$ and $/\phi$ to the inputs of a driver circuit such as that shown in FIG. 6. Control logic 502 controls the switch circuit to establish and switch the connections to correspond to the bit stream.

Combinations of frequency modulation, amplitude modulation, and/or phase modulation may also be used as desired.

In some embodiments, the transmitter may transmit a "packet" that includes a unique identifier for the remote device and that also provides information from the remote device (e.g., a measured or operating parameter M). Transmitting a unique identifier can be particularly useful when multiple remote devices with transmitters are present in the same patient. Other techniques for distinguishing different transmitters may also be used, including: operating different transmitters in different frequency bands, allowing each transmitter to be identified by its frequency and/or configuring different transmitters to transmit at different (and known) times, allowing the transmitter to be identified by when it transmits.

D. Further Aspects of Remote Devices

More generally, any number of remote devices may be provided, and each remote device may include one or more units (sensors and/or effectors and/or transmitters in any combination). Transmitters may transmit signals to, and in some embodiments also receive signals from, a central data collector and/or one or more other remote devices. In some instances, different units on a remote device will be identifiable in some way by the central collector. For example, different sensor or effector units of a single remote device may be addressable, may transmit signals using different frequencies, at different times, and/or the like, and the transmissions from different transmitters may include identification codes identifying a sensor, effector or transmitter to which the transmission pertains. In some instances at least, addressable units, particularly addressable effectors, are preferred where a digital or other switching circuit is provided at or on the unit to allow external digital or other controllers or circuitry to selectively power, actuate, or otherwise initiate operation of the unit.

A remote device can be fabricated on a carrier such as a semiconductor substrate, and the various units (sensors and/or transmitters and/or effectors) may be mounted to a surface of the carrier and/or disposed within the body of the carrier as appropriate. Remote devices of appropriate size and shape can be placed virtually anywhere in the body, including in one or more chambers of the heart, in arterial or venous vasculature, in or on brain tissue, in the urinary, gastrointestinal or reproductive tracts, in the abdominal cavity, in a joint space and so on. The devices can be operated to diagnose, monitor, and/or treat a wide array of medical conditions.

III. Power Source

Remote devices of the kind described in Section II in certain embodiments require power to operate any sensor unit, effector unit, or transmitter unit that may be included therein. The invention is not restricted to using particular power sources, and any power source suited for a particular application may be employed.

A. Near-Field Broadcast Power

In one embodiment, power is delivered wirelessly using quasi-electrostatic coupling. The operation is generally similar to the signal transmission described in Section II.C.1. The receiver in this instance includes circuits that are powered by the received current. In some embodiments, the receiver also includes a storage device (e.g., capacitor, chemical battery or the like) that is charged up by the received current and later discharged to extract useful work (e.g., sensing, effecting, and/or transmitting).

Figure 8:
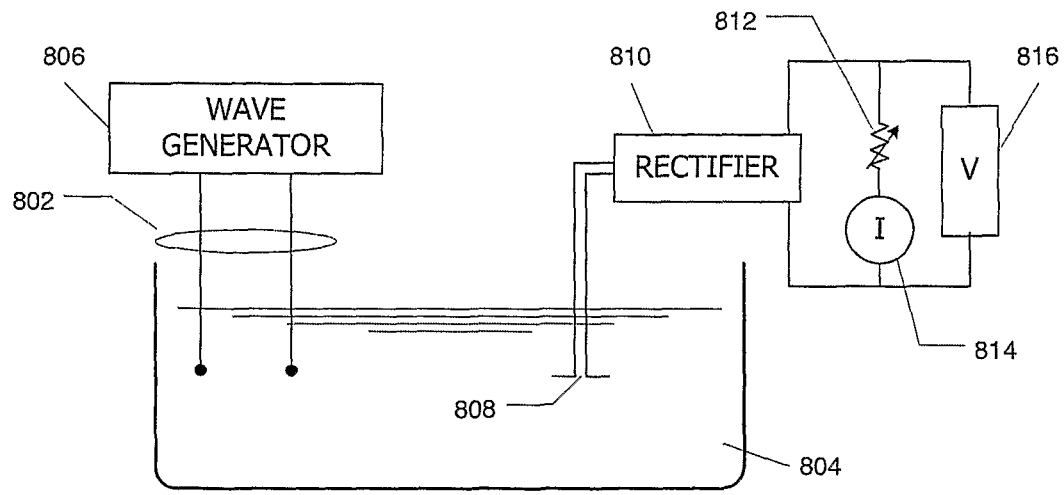
FIG. 8 is an experimental apparatus for testing a principle related to broadcasting power wirelessly through the body according to an embodiment of the present invention.

The possibility of broadcasting power wirelessly through the body has been demonstrated in an experimental apparatus shown in FIG. 8. Large copper electrodes 802, separated by about 20 cm, are immersed in a saline bath 804 and connected to a conventional wave generator 806. A small dipole antenna 808 was constructed of fine twisted-pair wire split into a "T" about 5 mm wide with about 1 mm of insulation stripped off each end and immersed in saline bath 804 at a location remote from electrodes 802. Antenna 808 was connected across a full-bridge rectifier 810 built with Schottky diodes (each of which has a threshold voltage of about 0.5 V, so that the rectifier is operational when the potential difference across antenna 808 exceeds about 1 V). Across the other arms of the bridge was connected a variable load including a 2-MΩ variable resistor 812 in series with an ammeter 814. A differential amplifier 816 was connected across the load to measure any potential difference.

Figure 9:
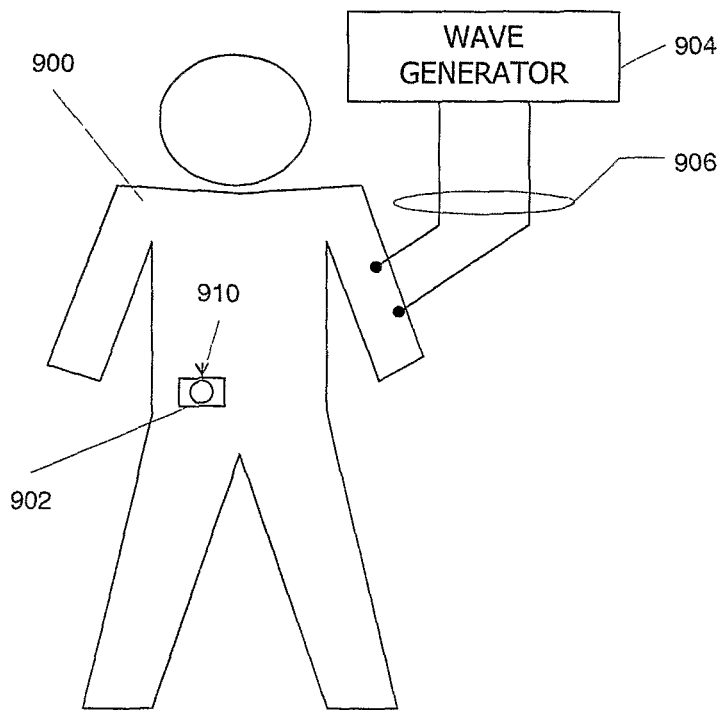
FIG. 9 illustrates a clinical use of an apparatus similar to that of FIG. 8 according to an embodiment of the present invention.

This arrangement is similar to the clinical use embodiment illustrated in FIG. 9. A patient 900 has a remote device 902 implanted somewhere in his (or her) body. Wave generator 904, which is external to the patient 900, has electrodes 906 that attach to the patient's skin at a convenient point. Remote device 902 includes an antenna component 910 that may be of comparable dimensions to antenna 808 of FIG. 8 and a load consisting of sensing, effecting, and/or transmitting circuitry that consumes power. If remote device 902 includes a transmitter unit, antenna component 910 may or may not also be used as the transmitter antenna, as desired. In another embodiment, wave generator 904 is implanted in the patient's body; for instance, the leads of a pacemaker can might be used as the electrodes, and the can may be configured to generate a waveform of suitable frequency across the leads.

Referring again to FIG. 8, in operation of the experimental apparatus, a sinusoidal voltage of 5 V or 10 V (peak-to-peak) with frequency of 100 kHz was applied to electrodes 802, and ammeter 814 and amplifier 816 were operated to detect current and voltage respectively, from which power could be determined. For a 10-V input oscillation, a peak power of 4 μW was detected at a potential of about 1 V across amplifier 816. It is believed that higher power output could be attained by replacing the high-threshold rectifier 810 with a more sophisticated design optimized for lower power. It is also believed that the current-handling capacity of antenna 808 could be increased by replacing the fine wire with electrodes having a larger surface area, such as a metallized surface of an integrated circuit chip.

In any case, the power generated would likely remain relatively small, but would be sufficient for many applications. For instance, as noted above, transmitters with a few microwatts of signal strength are sufficient for quasi-electrostatic communication within the body. In addition, for some applications it may be desirable to power the remote unit intermittently. The remote unit can be equipped with a charge storage device (e.g., a capacitor, chemical battery, etc.) so that it charges up for some period of time, then discharges, drawing power to perform its sensing, effecting, and/or transmitting operations. Where the duty cycle of a device might be small, the peak power available can be further increased by discharging the storage device faster.

B. Reverse Electrolysis

Another class of power sources exploits reverse electrolysis in an ionic solution such as gastric fluid, blood, or other bodily fluids and some tissues. It is well known in the art that two electrodes made of different metals and placed some distance apart in an ionic solution develop a potential difference as the ionic materials in the solution recombine. (This is the operating principle behind, e.g., hydrogen fuel cells).

Figure 10:
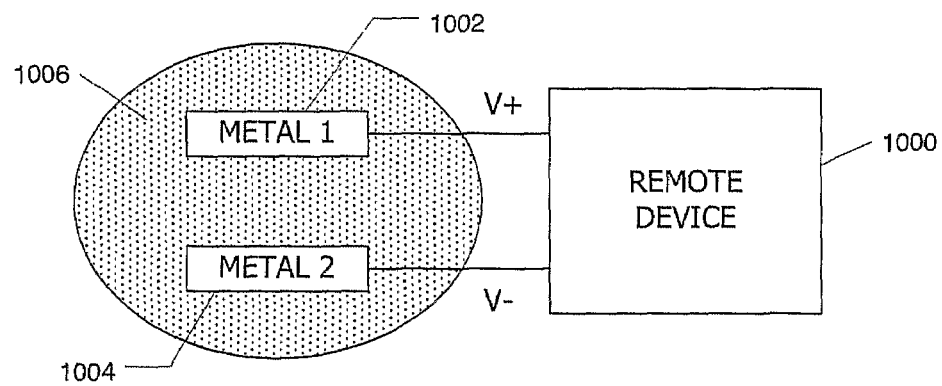
FIG. 10 illustrates a remote device powered by reverse electrolysis according to an embodiment of the present invention.

FIG. 10 illustrates a remote device 1000 powered by reverse electrolysis. Remote device 1000 is electrically connected to metal electrodes 1002 and 1004, which are made of two different metals and are electrically insulated from each other. As is known in the art, when metal electrodes 1002 and 1004 are immersed in an ionic solution 1006, a potential difference develops between them; for instance, electrode 1000 rises to a higher potential V+ while electrode 1004 falls to a lower potential V−. This potential difference can be used to power circuitry in remote device 1000.

Electrodes 1002 and 1004 can be implemented in various ways; for instance, areas on opposing surfaces of an integrated circuit chip can be coated with two different metals, and the entire chip can be placed in the ionic solution. Alternatively, electrodes 1002 and 1004 may extend away from remote device 1000 as shown. Other arrangements may also be used.

Electrodes 1002 and 1004 can be made of any two metals appropriate to the environment in which remote device 1000 will be operating. For instance, in some embodiments where ionic solution 1006 comprises stomach acids, electrodes 1002 and 1004 may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow remote device 1000 to perform its intended function.

Additional types of power sources such as those described above that are of interest include, but are not limited to, those described in pending PCT application serial no. PCT/US2006/016370, the disclosure of which and priority applications thereof are incorporated herein by reference.

C. Other Sources

Other sources, internal or external to the remote device, may also be employed in addition to or instead of those described above. For example, chemical or radioisotope batteries with a suitable form factor may be used to power some remote devices. Recently-developed fuel cells that use blood as an energy source can be miniaturized and used to provide electrical energy for a low-power microchip. Piezoelectric crystals that convert mechanical energy (e.g., compression) to electrical energy can be employed for remote devices disposed where suitable mechanical forces can be brought to bear, such as in or around the heart, stomach, joints, or other moving parts of the body. See e.g., pending U.S. application Ser. No. 11/385,986, the disclosure of which is herein incorporated by reference. IN addition, power sources modeled on the cellular energy factory, with power being extracted from ATP in the blood so that blood, in effect, "nourishes" the remote device, may be employed. In other embodiments, acoustic energy (e.g., ultrasound) can be coupled into a remote device through piezoelectric or similar converters.

IV. Data Collector

Referring again to FIG. 1, platform 100 also provides a data collector 106. As used herein, a "data collector" is any device equipped with receiving antenna to detect the potential differences created in the body by a transmitter as described above, thus receiving the information transmitted. A data collector may handle received data in various ways. In some embodiments, the collector simply retransmits the data to an external device (e.g., using conventional RF communication). In other embodiments, the data collector processes the received data to determine whether to take some action, such as operating an effector that is under its control, activating a visible or audible alarm, transmitting a control signal to an effector located elsewhere in the body, or the like. In still other embodiments, the data collector stores the received data for subsequent retransmission to an external device or for use in processing of subsequent data (e.g., detecting a change in some parameter over time). In yet other embodiments, the data collector may retransmit the data to another internal device, which then relays the information to yet another device, as desired, e.g., where a plurality of such devices are distributed throughout the body of a patient and the plurality of such devices serves to relay information from one location to another. It is to be understood that data collectors may perform any combination of these and/or other operations using received data.

While the receiving antenna is advantageously inside the patient or in contact with the patient's skin, it is not required that data collector 106 be entirely internal to the patient. For instance, a watch or belt worn externally and equipped with suitable receiving electrodes can be used as a data collector in accordance with one embodiment of the present invention.

The data collector may provide a further communication path via which collected data can be extracted by a patient or health care practitioner. For instance, an implanted collector may include conventional RF circuitry (operating, e.g., in the 405-MHz medical device band) with which a practitioner can communicate using a wand as is known in the art. Where the data collector includes an external component, that component may have output devices for providing, e.g., audio and/or visual feedback; examples include audible alarms, LEDs, display screens, or the like. The external component may also include an interface port via which the component can be connected to a computer for reading out data stored therein.

In some embodiments, the data collector is implanted. For instance, as noted above, pacemaker leads provide a suitably sized receiving antenna. Typical pacemakers include a control unit (referred to as a "can") that incorporates logic circuits configured to perform various data collection and processing operations. The can is also connected to RF transmitter/receiver circuitry that allows communication between the pacemaker and an external wand operated by a health care practitioner. Thus, where the patient has a pacemaker, leveraging the existing unit as a data collector for platform 100 of FIG. 1 may be an efficient choice.

Other devices may also be implanted, and within the meaning of platform 100 the same device might operate as both a remote unit (e.g., an effector) and a data collector that uses received signals to determine whether and how to operate the effector.

V. Example Systems

The preceding sections describe a general-purpose platform, e.g., for medical diagnosis and/or treatment of a patient, using one or more implantable devices that are capable of communicating with each other. Numerous examples of various components of and uses for such platforms have already been described, and it is contemplated that persons of ordinary skill in the art with access to the present teachings will readily develop other examples of components and uses.

To further illustrate the platform described herein, specific examples of diagnostic and/or therapeutic systems built on this platform will now be described. It is to be understood that these examples are illustrative and not limiting of the invention.

A. Smart Pill (Pharma-Informatics System)

In one embodiment, the remote device 104 of FIG. 1 comprises an ingestible pill that contains a transmitter unit. As the pill is digested, the transmitter is activated and transmits a signal, allowing ingestion of the pill to be detected and reported by a data collection unit 102. Examples of such pills are described in pending PCT application serial no. PCT/US2006/016370, the disclosure of which and priority applications thereof are incorporated herein by reference. In some embodiments, the pill includes an integrated circuit chip that implements a transmitter for an embodiment of platform 100. The chip is advantageously compact enough to fit completely inside a pill that a patient can swallow.

Figure 11:
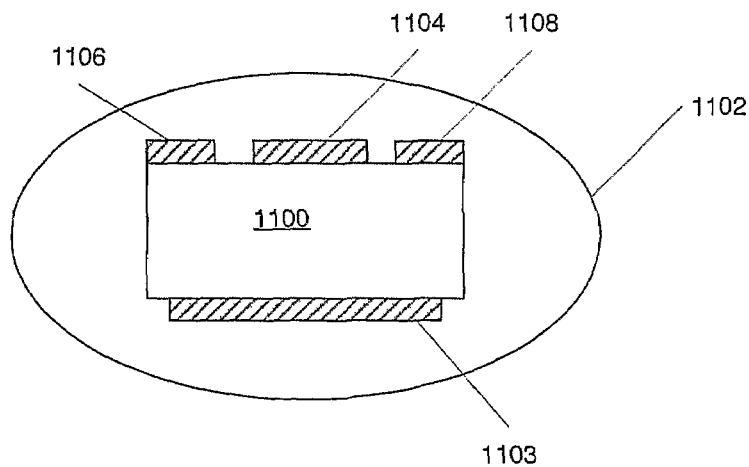
FIG. 11 illustrates a remote device disposed inside a pill according to an embodiment of the present invention.

FIG. 11 illustrates a remote device 1100 disposed inside a pill 1102. Device 1100 is an integrated circuit. The backside (bottom) of circuit 1100 is at least partially coated with a first metal 1103, and a portion of the front (top) of circuit 1100 is coated with a different metal 1104, allowing circuit 1100 to be powered by reverse electrolysis as described in Section III.B above. Also on the top surface are two transmitter electrodes 1106, 1108.

When pill 1102 is fabricated, integrated circuit 1100 is surrounded by at least one external layer that may include pharmacologically active and/or inert materials in any combination. The external layer dissolves in the stomach through a combination of the mechanical action of the stomach and the action of various chemical constituents (e.g., hydrochloric acid) in stomach fluids.

As pill 1102 is dissolved, areas of integrated circuit 1100 become exposed to the stomach contents, which for present purposes can be regarded as an electrolyte solution. As dissolution of the pill exposes metal layers 1103 and 1104, power is supplied to circuit 1100, which begins to operate and continues to operate until metal layers 1103 and 1104 or the circuit itself are sufficiently dissolved by digestive processes and acids to become non-functional. Eventually, the remains of the chip are excreted from the body.

In an alternative embodiment, integrated circuit 1100 is attached to, rather than encapsulated in, pill 1102. For instance, circuit 1100 might be placed at one end of the pill as the pill is being prepared, in a soluble coating on the surface of the pill, or the like. In embodiments where circuit 1100 is wholly or partially exposed, integrated circuit 1100 begins to operate sooner after the pill enters the stomach rather than after the pill dissolves.

In one embodiment, circuit 1100 transmits a signal identifying pill 1102. The identifier may indicate the type (active ingredient(s), brand, etc.) and/or dosage of pill 1102 and may also provide a lot number, serial number, or similar identifying information that would allow particular pills to be traced.

Figure 12:
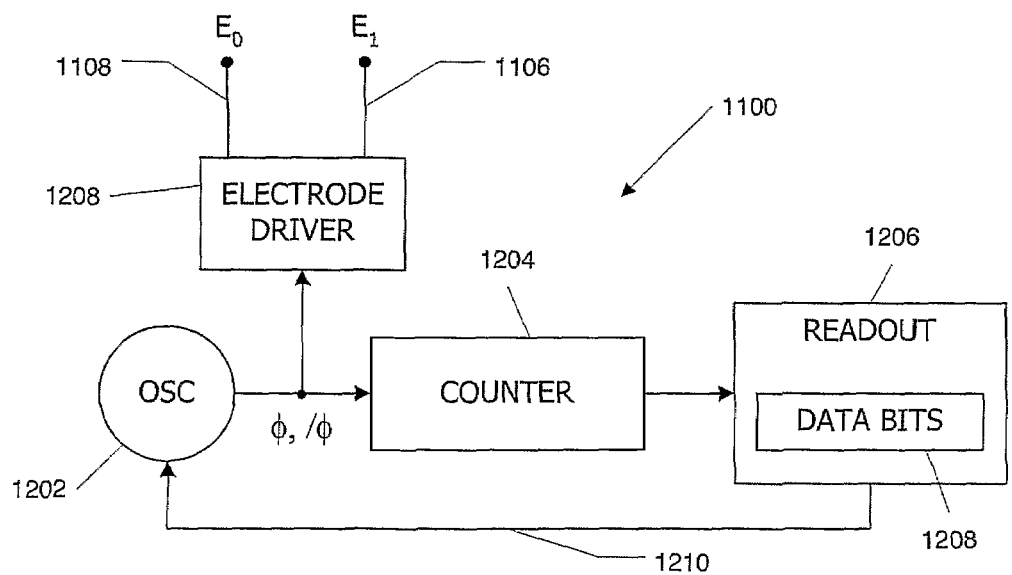
FIG. 12 is a block diagram of an electronic circuit that may be included in the remote device of FIG. 11 according to an embodiment of the present invention.

FIG. 12 is a block diagram of one embodiment of electronic circuit 1100. In this embodiment, circuit 1100 is a transmitter unit that sequentially transmits a predetermined series of address (identifier) bits using frequency shift keying, with a first oscillation frequency corresponding to bit value 0 and a second oscillation frequency corresponding to bit value 1.

As described above, metal layers 1103 and 1104 supply power to circuit 1100. The power (not explicitly shown in FIG. 12) is supplied to an oscillator 1202, a counter 1204, a readout circuit 1206, and an electrode driver 1208 that drives transmitter electrodes 1106, 1108 to transmit the signal.

Oscillator 1202 may be of generally conventional design (e.g., a ring oscillator) and is advantageously configured to operate in the quasi-electrostatic frequency region as described above. Oscillator 1202 generates a driving signal $\phi$ that oscillates between high and low voltage levels and an inverted driving signal $/\phi$ that is opposite in phase to driving signal $\phi$. In one embodiment, oscillator 1202 is a voltage-controlled oscillator (VCO) with an oscillation frequency that depends on a control voltage provided on a signal path 1210.

Counter 1204 counts the oscillations of driving signals $\phi$ and $/\phi$ and provides the current count to readout circuit 1206. In one embodiment, counter 1204 is an eight-bit counter of generally conventional design; other types of counters (including counters with different widths) may also be used. Readout circuit 1206 is configured with a set of address (identifier) bits 1212 that are advantageously fixed, e.g., at the time circuit 1100 is fabricated; as noted above, the bits can be unique to a particular instance of pill 1212 or common to a lot of pills fabricated under the same conditions or common to all pills containing a particular pharmacological agent. Address bits 1212 can be stored in nonvolatile storage circuits of generally conventional design, and any number of address bits (e.g., 8, 16, 32, 48, . . . ) may be provided.

Readout circuit 1206 generates an oscillator control signal (e.g., a voltage) on line 1210 that controls the frequency of VCO 1202. In one embodiment, readout circuit 1206 is configured to select a current address bit, e.g., based on the current count provided by counter 1204, and to generate a control signal on signal line 1210 that selects a frequency corresponding to the value of that bit. After some number of cycles (as determined by counter 1204), readout circuit 1206 selects the next address bit and generates the corresponding control voltage on signal line 1210.

Various frequencies may be used to represent the address bit values "1" and "0." In one embodiment, frequencies of 100 kHz and 200 kHz may be used to represent values "0" and "1," respectively. Other values (e.g., 1 MHz and 2 MHz or 1 kHz and 5 kHz) may also be used. The chosen frequencies advantageously are well below the absorption modes of human tissues, which are typically above 400 MHz. In certain embodiments, VCO 1202 is configured to operate at a frequency of about 10 MHz or less, such as about 1 MHz or less. In certain embodiments, the oscillator is configured to operate at frequency between about 300 Hz and about 1 MHz.

As described above, VCO 1202 generates complementary signals φ, /φ that oscillate at a frequency determined by the control signal on signal line 1210. The signals φ, /φ are used to control an electrode driver 1208, which may be implemented, e.g., as shown in FIG. 6.

It should be noted that since electrodes 1106 and 1108 are in contact with stomach fluids when circuit 1100 is operative, the near-field component is coupled directly into the conductive medium of the patient's body and can be detected by a suitably configured data collector as described above. In one embodiment, the collector is configured to log the received address (identifier) and the time of receipt. The data collector can also be configured to retransmit this information to an external device, either in real time or while the patient is in a medical facility.

It will be appreciated that the transmitter described herein is illustrative and that variations and modifications are possible. For instance, other encoding schemes could be used to transmit the data; in one such embodiment, phase shift keying rather than frequency keying is used. In some embodiments, multiple address bits can be encoded into a single symbol that is transmitted using various keying schemes known in the art.

Such transmitters encapsulated in or attached to a pill have a number of uses. For instance, by reference to data collected and reported externally, it can be determined whether a patient is following a prescribed drug regimen. In addition, the timing of pill ingestion can be correlated with changes in other physiological parameters (some or all of which might be monitored, e.g., by other remote devices implanted in the patient's body as described above), and the correlations can be used to assess the effectiveness of a particular drug or dosage. Further, in cases where the transmitter becomes active only as the pill dissolves (e.g., where the transmitter is initially completely encapsulated in the pill), the transmitted signal can indicate dissolution of the pill. As another example, if the data collector includes a component worn by the patient, an alarm can be activated if the pill's presence is not detected at the appropriate time, reminding the patient to take the medication. Further examples of uses for such transmitters are described in pending PCT application serial no. PCT/US2006/016370, the disclosure of which and priority applications thereof are incorporated herein by reference.

B. Fluid Flow Sensors

Embodiments of the present invention provide fluid, e.g., blood, flow sensors that can be used for measurement of various physiological parameters under a wide array of conditions. Although the assessment of blood flow is emphasized in the following description, it will be understood that the flow of many other physiological fluids can be determined by the internal electromagnetic flow sensor taught herein. For instance, the flow of cerebral spinal fluid, lymph fluids, fluids in the pleural cavity, lachrymal gland flow, intraocular fluid in the case of glaucoma, urine from the kidneys, among many can be assessed.

The present invention provides data completely independent of the nature of the fluid allowing this broad applicability. In some embodiments, the blood flow sensor can be implanted into a blood vessel and left in place indefinitely and will unobtrusively measure and record data as the patient engages in regular daily activities. The data can later be read out by a clinician using a suitable interface. In other embodiments, the data is collected and analyzed within a data collection device implanted in or attached to the patient's body, and the collection device can report to the patient on an ongoing basis or in the form of alerts issued when conditions requiring medical intervention are detected. The blood flow measurements can be used to detect, evaluate and treat numerous conditions, examples of which are described below.

In one embodiment, a remote device 104 of FIG. 1 includes a blood flow sensor that can measure flow velocity and/or hematocrit (the percentage, by volume, of the patient's blood that is made up of red blood cells). These measurements can be used to detect various physiological conditions. For instance, "stroke volume"—i.e., the volume of blood flowing into or out of the heart per cardiac cycle—can be determined by measuring blood flow velocity in an artery (e.g., the aorta) or vein (e.g., the vena cava) and using the cross-sectional area of the blood vessel and duration of the cardiac cycle to compute stroke volume. As another example, circulatory problems (e.g., blockages) can also be detected through blood flow measurements. Localized changes in physiological activity (e.g., digestion, brain activity, tumor growth or shrinkage, and so on) can be detected by changes in blood flow in the relevant region of the body, since body systems require more oxygen (and hence greater blood flow) when they are more active. Any of these or other uses can be made of blood flow data, and the particular application for which a sensor is employed is not relevant to the present invention.

In certain embodiments, a remote device including the blood flow sensor is implanted in a blood vessel and measures blood flow and/or hematocrit at the target fluid flow location. The remote device also includes a transmitter that periodically or continuously transmits the measured data to a data collector using quasi-electrostatic signaling techniques as described above.

Fluid flow sensors in accordance with the present invention may have a variety of different configurations. In certain embodiments, the sensors are present on remote, stand alone devices that are implantable and communication with each using a wireless communications protocol, such as the quasi-electrostatic protocol as described above. Such remote stand-alone devices are implantable and in certain embodiments small, e.g., having a longest dimension that does not exceed about 5 cm, such as does not exceed about 1 cm, such as does not exceed about 10 mm, such as does not exceed about 1 mm, where in certain embodiments the longest dimension of the implantable stand-alone device may be much shorter than 1 mm. These embodiments may viewed as devices that are not present on another implantable device, such as a lead.

In yet other embodiments, the sensors may be part of an implantable device, such as a lead, which is connected to other implantable devices, e.g., a can. Of interest in these embodiments is the use of multiplex lead configurations, such as multiplex lead configurations in which each sensor is part of an addressable satellite on the lead. Such multiplex leads include those described in U.S. application Ser. Nos. 10/734,490 published as 20040193021; 10/764,429 published as 20040220637, 10/764,127 published as 20040254483; and 10/764,125 published as 20040215049 (the disclosures of which applications are herein incorporated by reference); and PCT application serial nos. PCT/US2005/031559 published as WO/2006/029090, PCT/US2005/046811 published as WO/2006/069322 and PCT/US2005/046815 published as WO/2006/069323, the disclosures of which applications and priority applications thereof are incorporated herein by reference. Depending on the nature of the sensor and operation thereof, in certain embodiments the multiplex leads are those described in these pending applications, where the leads are configured to obtain fluid flow data.

In the broadest sense, the fluid flow sensor may be any convenient sensor. In certain embodiments, the blood flow sensor is a fluid flow resistance sensor. In certain embodiments, the blood flow sensor is a fluid flow electromagnetic sensor. Embodiments of each of the illustrative embodiments of fluid flow sensors are now described in greater detail.

1. Resistance Fluid Flow Sensor

In some embodiments, the sensor exploits the well-known property that the resistivity of blood varies directly with the flow velocity and inversely with hematocrit, i.e., the percentage, by volume, of whole blood that is made up of red blood cells. (See, e.g., Hoetnik et al., *IEEE Trans. Biomed. Engr.* 51:.7, 1251 (2004); Sigman et al., *Amer. J. Physiol.*, 118, 708 (1937)).

In one embodiment, a blood flow sensor includes a sensor module configured to apply a current between two terminals that contact the blood stream. Sensing electrodes and a differential amplifier are arranged near the terminals to detect a potential difference created by the resistivity of the blood. This potential difference is related to the resistivity, which in turn correlates with the blood flow velocity.

In another embodiment, the blood flow sensor includes a wireless transmitter configured to communicate the measured potential difference to a data collection device that may be implanted in or attached to the patient's body. The wireless transmitter advantageously uses quasi electrostatic near field coupling to send the data to the data collection device. At the data collection device, the data can be recorded for later reporting to a clinician, used to compute additional physiological parameters, and/or used to determine whether to take some automated action, such as alerting the patient, dispensing a dose of a medication, stimulating the heart muscle, or the like.

Figure 13:
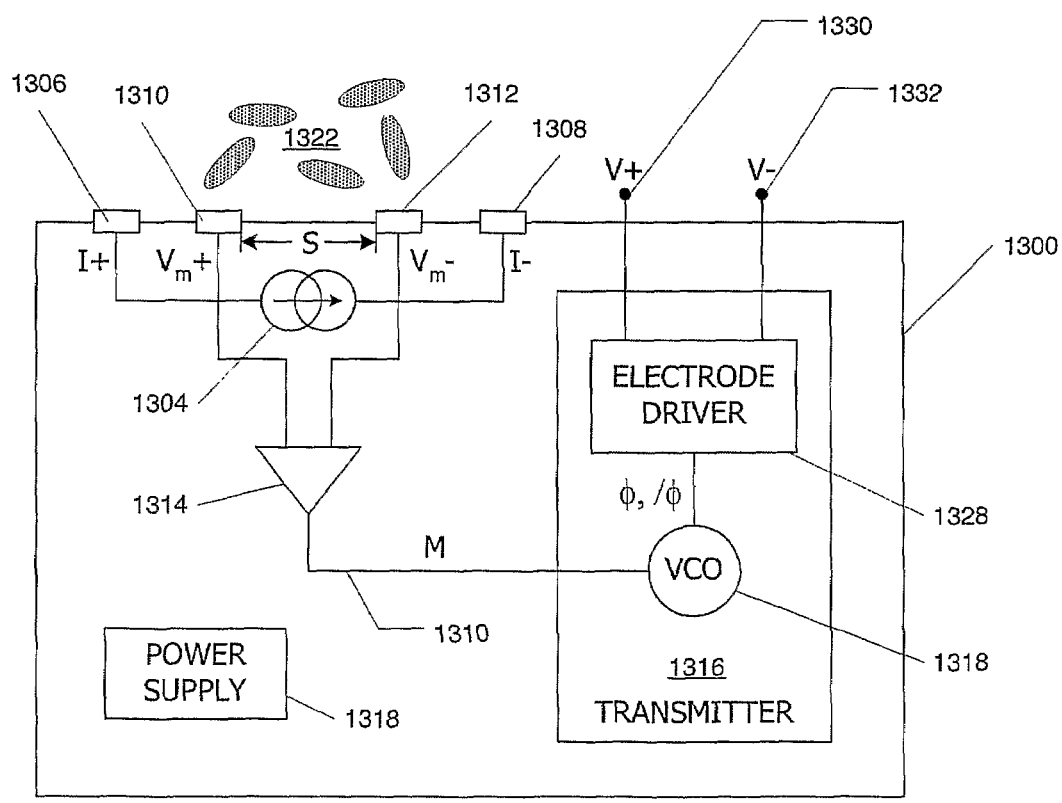
FIG. 13 is a block diagram of a blood flow sensor according to an embodiment of the present invention.

FIG. 13 is a block diagram of blood flow sensor 1300 according to an embodiment of the present invention. Sensor 1300 includes a current source 1304 connected between terminals 1306 and 1308, sensing electrodes 1310 and 1312, a differential amplifier 1314, a transmitter section 1316, and a power supply 1318. Sensor 1300 can be implemented, e.g., as an integrated circuit on a semiconductor substrate using conventional fabrication techniques. Power supply 1318 provides power to all of the other components (the connections are not shown but will be well understood by those of ordinary skill in the art) and may be implemented in various ways, including any of the techniques described in Section III above. For instance, in some embodiments, power supply 1318 includes a conventional battery. In other embodiments, power supply 1318 includes electrodes of two different metals exposed to the flowing blood, and power is generated through reverse electrolysis. In still other embodiments, power supply 1318 collects energy from a remote source, e.g., via near field quasi electrostatic coupling (e.g., as described above). In embodiments with a remote power source, blood flow sensor 1300 can be activated at desired times by transmitting power from the remote power source. It will be appreciated that a particular power source or power supply configuration is not critical to the present invention, and a detailed description is omitted.

In operation, sensor 1300 is placed inside a blood vessel, preferably at a fixed location, with terminals 1306, 1308 and sensing electrodes 1310, 1312 exposed to the flowing blood, represented in FIG. 13 by red blood cells 1322. Current source 1304, when powered by power supply 1318, applies a constant current/between terminals 1306 and 1308. The current passes through the blood, which has a resistivity $\rho$ that depends in part on the flow rate and in part on hematocrit. The flowing current creates a potential difference ($\Delta V$) across sensing electrodes 1310, 1312 that depends on the current I, the resistivity $\rho$ of the blood, and the distance S between sensing electrodes 1310 and 1312. In one embodiment, $\Delta V = \rho I/2\pi S$, as described in Barber & Brown, *J. Phys. E. Sci. Instrum.*, 17, 723 (1984).

The potential difference $\Delta V$ is detected and amplified by differential amplifier 1314. A measurement M, proportional to $\Delta V$, is generated on a signal line 1324 that connects to transmitter section 1316.

It should be noted that the distance S between sensing electrodes 1310 and 1312 may be varied as desired. Where S is comparable to the size of a red blood cell (e.g., 6-8 microns), it becomes possible to count individual red blood cells flowing past. In a "cell-sized" configuration, a discrete pulse in $\Delta V$ occurs as red blood cells pass close to the device, analogous to shot noise in electronic circuits in other contexts. In certain embodiments, the distance S is about 20 microns or less, such as about 10 microns or less, including about 8 microns or less. Amplifier 1314 can be connected to a counter that counts the pulses, thereby counting red blood cells and providing a measurement of hematocrit. In some embodiments, flow velocity and hematocrit can be measured separately.

The measurement value M can be reported to another device located within the patient's body. In some embodiments, as shown in FIG. 13, sensor 1300 includes a transmitter section 1316 that transmits the value M wirelessly, using quasi electrostatic transmission techniques, e.g., as described in above.

Transmitter section 1316 receives the measurement data (e.g., signal M on line 1324) and transmits the data using near-field coupling as described above. In one embodiment, transmitter section 1316 transmits at a frequency determined by M. In this embodiment, transmitter section 1316 includes a voltage-controlled oscillator (VCO) 1326 and an electrode driver 1328, which may be generally similar to the oscillator and electrode drivers described above. VCO 1326 oscillates at a frequency determined by the measurement signal M, generating signals $\phi$ and $/\phi$. These signals induce electrode driver 1328 to drive transmission electrodes 1330, 1332 at a corresponding frequency.

Transmitter section 1316 may also implement other techniques for encoding and transmitting data. For instance, amplitude modulation based on the measurement data M might be substituted for frequency modulation. In another embodiment, transmitter section 1316 might include an analog-to-digital converter that converts the measured signal M to a corresponding digital value. This digital value can be encoded and sent similarly to the address bits described above with reference to FIG. 12, using amplitude modulation, frequency modulation, phase modulation, or any combination thereof. In addition, in some embodiments, an identifier of the sensor may be encoded and transmitted along with the measurement value. Transmitting an identifier allows multiple sensors placed at different locations in the patient's body to report measurements, with each reported measurement being associated with its source.

The signal from sensor 1300 is detected by a data collector 106 (see FIG. 1) and the information therein is handled appropriately. For instance, the data collector may store the information for later reporting to the patient's health care practitioner, or it may use the information to control a pacemaker, release an anti-clotting agent into the blood, detect blockages developing in real time and generate appropriate alarms, and so on.

Figure 23:
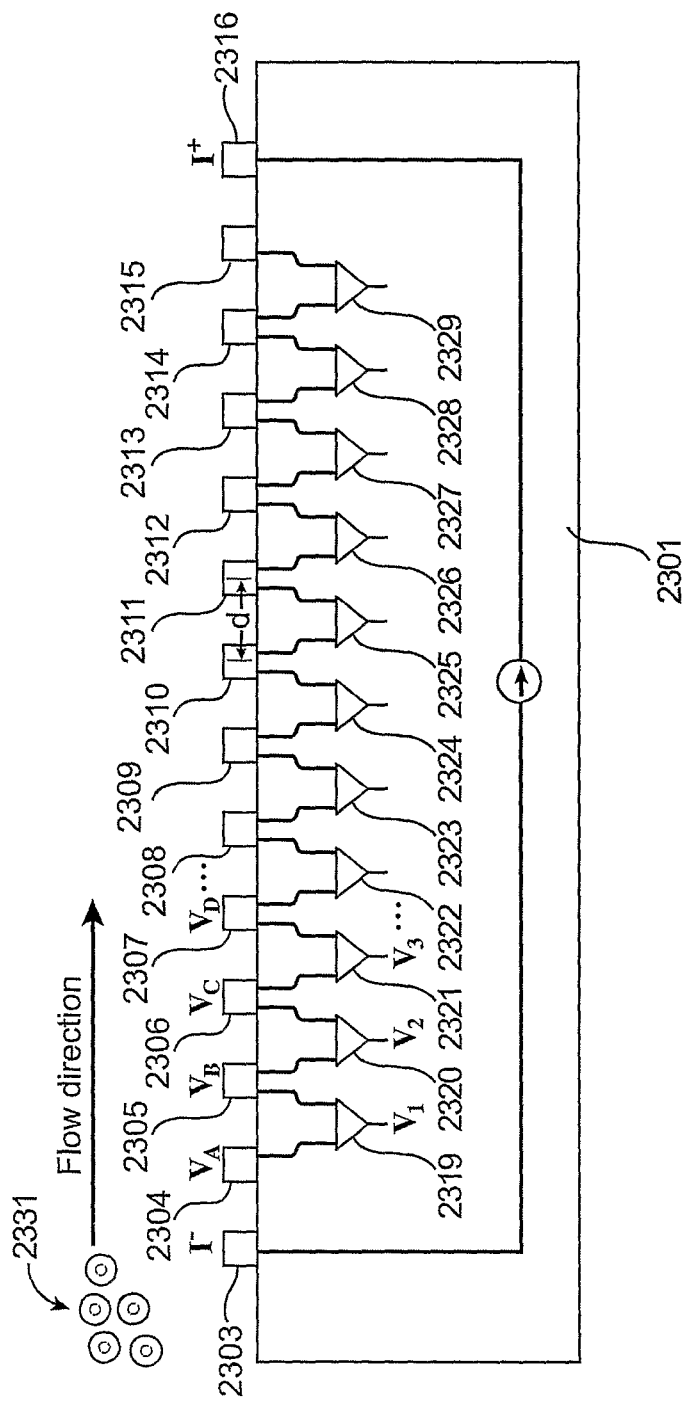
FIG. 23 shows an embodiment of a resistance blood flow sensor according to an embodiment of the present invention.

In certain embodiments of the present invention, the inventive blood flow sensor includes a plurality of electrodes located on a surface of a solid support, such as a silicon chip, e.g., as shown in FIG. 23.

FIG. 23 shows an embodiment of the inventive blood flow sensor, which consists of a silicon chip 2301 with fourteen electrodes 2303-2316 located on its surface. Each electrode 2303-2316 is separated by a uniform distance, d. The outermost electrodes 2303 and 2316 are configured as a current source to drive current through the fluid. The other electrodes 2304-2315 are configured as voltage sensing electrodes. The voltage signals at all neighboring electrodes are passed through differential amplifiers 2319-2329 to obtain the voltage difference between the two electrodes. The voltage at the output of each amplifier 2319-2329 is passed to processing circuitry, where it is analyzed. As red blood cells 2331 pass each pair of electrodes, the resistance between the pair of electrodes is increased. This creates a spike in the voltage difference measured between the electrodes.

Figure 24A:
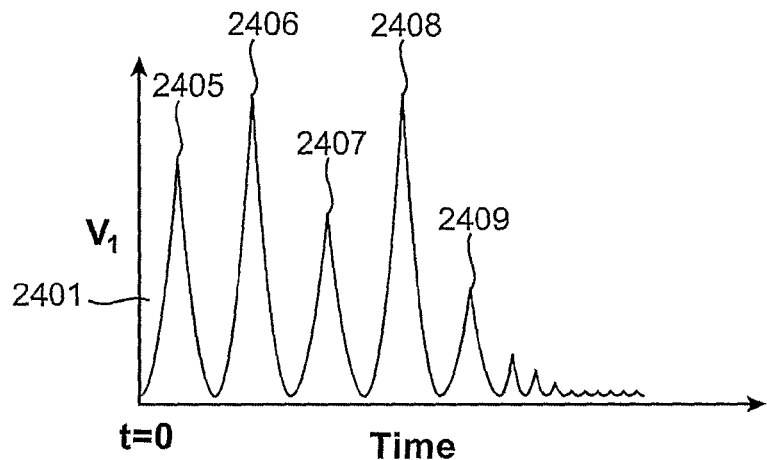
FIGS. 24A to 24C provide depictions of the type of data that may be obtained with a sensor as shown in FIG. 23.

FIG. 24A shows theoretical data for the voltage signal measured by the device shown in FIG. 23 at the output of amplifier 2319, which outputs the voltage difference between electrodes 2304 and 2305. This waveform 2401 would be expected when a group of red blood cells passes the space between electrodes 2304 and 2305. Each peak 2405-2409 is caused by one red blood cell passing electrodes 2304 and 2305. The control circuitry counts the peaks to give an estimation of hematocrit on a continuous, in vivo basis.

Figure 24B:
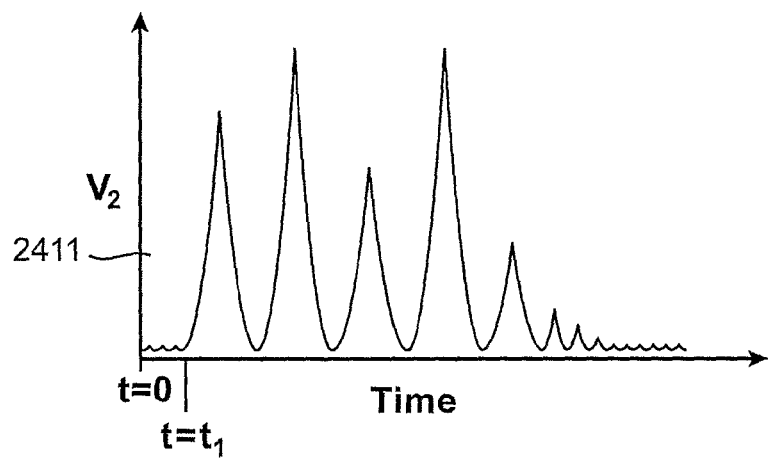

FIG. 24B shows theoretical data for the voltage signal measured by the device shown in FIG. 23 at the output of amplifier 2320, which outputs the voltage difference between electrodes 2305 and 2306. This waveform 2411 would be expected when the same group of cells that created waveform 2401 from FIG. 24A passes the space between electrodes 2305 and 2306. Waveform 2411 is very similar to waveform 2401 in FIG. 24A, except it is delayed by a time, $t_1$. The process circuitry receives waveforms 2401 and 2411 and correlates them using techniques well known in the art to recognize the analogous waveform, and find the time difference, $t_1$. The velocity, v, of the blood from the area between electrodes 2304 and 2305 and the area between electrodes 2305 and 2306 can then be calculated using the following formula:

$$v = d/t_1 \quad (3.1)$$

Figure 24C:
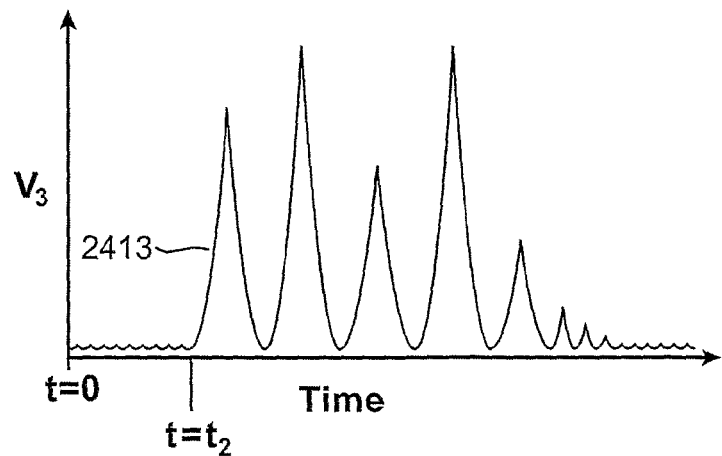

FIG. 24C shows theoretical data for the voltage signal measured by the device shown in FIG. 23 at the output of amplifier 2321, which outputs the voltage difference between electrodes 2306 and 2307. This waveform 2413 would be expected when the same group of cells that created waveform 2401 from FIG. 24A passes the space between electrodes 2306 and 2307. The waveform is very similar to waveform 2401, except that it is delayed by a time $t_2$. The correlation techniques are used to compare waveform 2413 with either waveform 2401 from FIG. 24A, waveform 2411 from FIG. 24B, or both. This will be used to calculate $t_2$. A roughly instantaneous velocity, v, of the blood from the area between electrodes 2305 and 2306, and the area between electrodes 2306 and 2307 can be calculated using the following formula:

$$v = d/(t_2 - t_1) \quad (3.2)$$

Alternatively, the average velocity, v, of the blood over a distance of 2d from the space between electrodes 2304 and 2305 from the device shown in FIG. 23 and the space between electrodes 2306 and 2307 can be calculated using the following formula:

$$v = 2d/t_2 \quad (3.3)$$

This inventive technique can be used to calculate hematocrit and blood velocity at and between every electrode pair along the length of the sensor. Using different electrode pairs, the spacing between the two data points can be varied depending on the desired information. Each successive neighboring pair can be used to track changes in blood flow over the length of the sensor. Alternatively, for a measure of the average blood flow over the length of the sensor, two electrode pairs that are spaced further apart may be used.

Other features of the cells may also be determined using the inventive sensor. For instance, the shape of the spikes can be used to determine the size of the cells. A larger cell would produce a broader spike, while a smaller cell would produce a sharper spike. By looking at the distribution of the spike width over a large number of cells, statistics such as the relative size of the minor axis of the cell to the major axis of the cell can be generated. This information can be used to evaluate the health of the cells. A further description of embodiments of blood flow sensors and medical applications of blood flow measurement can be found in above-referenced Provisional Application No. 60/824,308, the disclosure of which is herein incorporated by reference.

A further description of embodiments of blood flow sensors and medical applications of blood flow measurement can also be found in above-referenced Provisional Application No. 60/713,881, the disclosure of which is herein incorporated by reference.

2. Electromagnetic

As mentioned above, another type of fluid flow sensor provided by embodiments of the invention is an internal electromagnetic fluid flow sensor. The internal electromagnetic blood flow sensor of the present invention allows, for the first time, the accurate determination of internal fluid, e.g., blood, flow electromagnetically. This innovation enables the calculation of clinically useful physiological parameters, such as heart stroke volume.

The internal electromagnetic flow sensor of embodiments of the present invention has unique advantages over prior art methods. It is typically non-invasive or minimally invasive, and does not require changing blood temperature or physically impacting the blood. This aspect allows, for the first time, chronic monitoring of blood flow, even as patients go about their daily routines. This aspect is a very important feature for cardiac disease assessment.

The underling approach of the inventive internal electromagnetic flow sensor may be viewed as utilizing the Hall Effect. Many literature sources erroneously ascribe the Hall Effect to Faraday's law of induction. However, in the context of the present invention, the underlying physics basis for the internal electromagnetic flow sensor differs from Faraday's law. A key advantage of the internal electromagnetic blood flow sensor is that its signal is completely independent of the nature of the fluid being assessed, as long as it is of sufficient conductivity. The measure of flow is independent of factors such as hematocrit and blood makeup. As such, the sensors of these embodiments may be viewed as fluid composition independent fluid flow sensors.

Figure 15A:
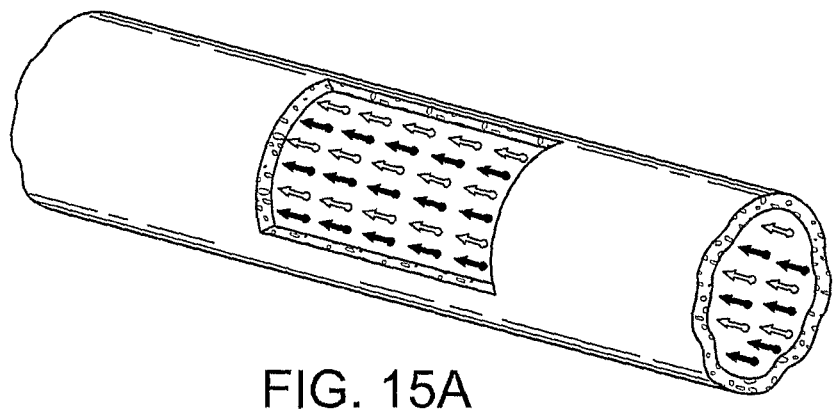
FIGS. 15A to 15E provide a diagram of the Hall principle effect on fluid and particles in the flowing blood.
Figure 15B:
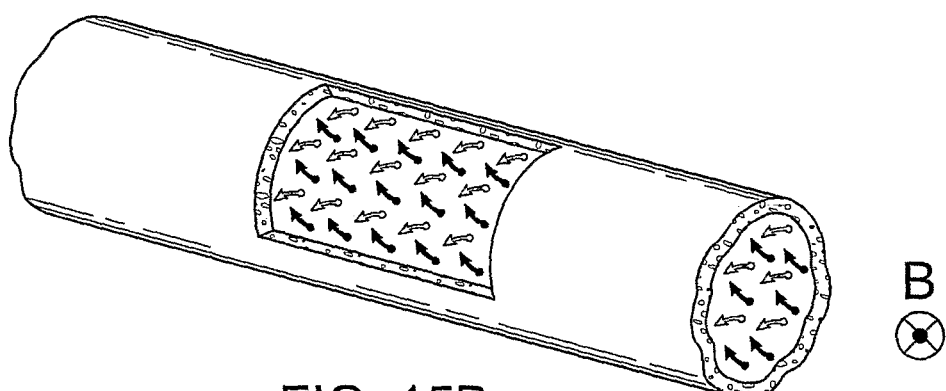
Figure 15C:
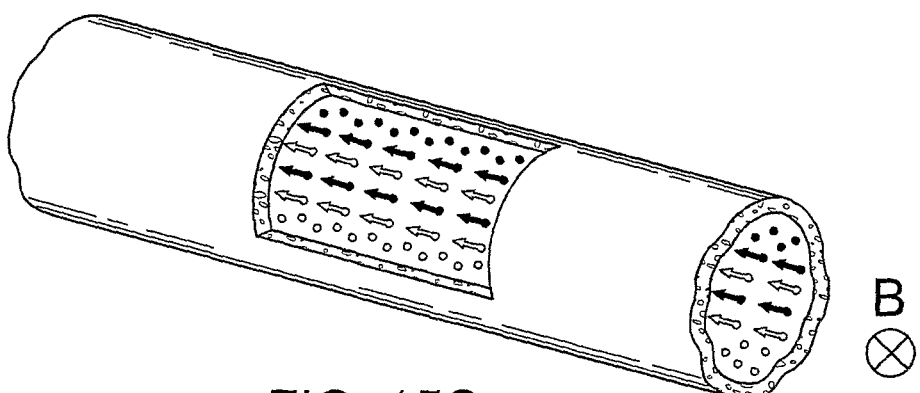
Figure 15D:
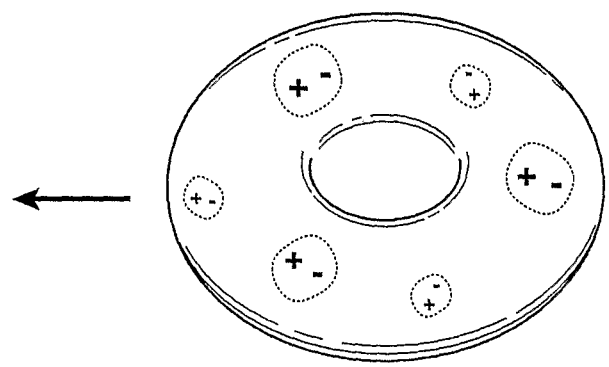
Figure 15E:
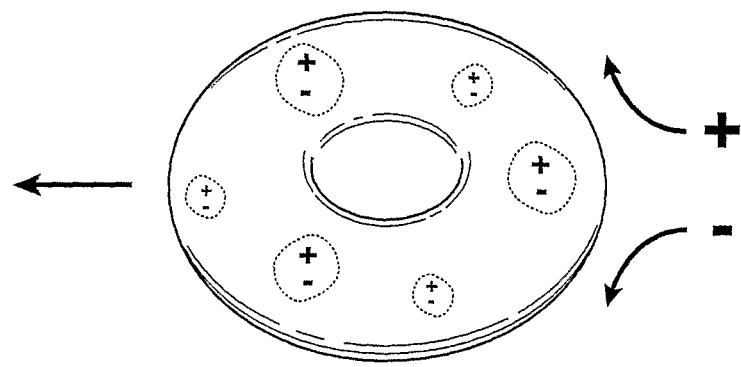

FIGS. 15A to 15E show the Hall Effect as it is used in the present invention. The Hall Effect is provided in the literature in the context of a current flowing through a solid conductor. Such articles demonstrate the broad Hall Effect principle. By example see Electricity and Magnetism Edward M Purcell, Berkeley Physics Course, Vol. 2, 2nd Ed. McGraw Hill, Boston 1985, The Magnetic Field, page 243, FIG. 6.28. This chapter of the Purcell reference is incorporated in its entirety herein by reference. However, in the present invention, the Hall effect is considered in the very different context of the mixed solids and liquids of body fluids, such as blood physically flowing though veins and arteries. In FIG. 15A, the electrons in the ions of the blood are shown as white circles, which are flowing through the conductive blood. When a magnetic field is applied transverse to the vein or artery in FIG. 15B, the negatively charged electrons in the ions, and the ions themselves deflect downward. The positively charged ions deflect upward. These electrons in the blood ions cannot travel very far downward because they hit the internal surface of the blood vessel. As a result, layers of charge are produced both on the bottom internal surface of the blood vessel and the top internal surface of the blood vessel. These two charge layers generate a transverse electromagnetic field in z direction in the figure. It is this electrical field which is detected by the present invention. While the Hall principle has previously been applied to conductive solids, the present inventors have discovered that it can also be applied to a conductive moving fluid. There are specific distinctions between these two cases. By example, in a conductive liquid, instead of only the electrons moving as in the case of the Hall principle in solids, both the electrons and the positive charge carriers move. Thus, in FIGS. 15A to 15C, the blood ions shown diagrammatically as black dots migrate upwards, which is not the case in electrons migrating in solid structures. The particles shown diagrammatically as white dots are deflected downwards. Ultimately, the end charge effect is somewhat analogues between the Hall Effect in the solid conductor and in a flowing conductive liquid. That is, a positive charge is generated on the up side, and the negative charge on the down side. Similar methods are used to detect the potential. FIGS. 15D and 15E provide diagrammatic views of how the molecules within larger blood inclusions have their molecules align when in the field of the internal electromagnetic blood flow sensor. As opposed to the case of blood ions migrating within the fluid, the molecules align in their set positions within solid blood inclusions. Red blood cells are provided as illustration in FIGS. 15D and 15E. However, platelets and other blood particles will be similarly affected. Despite the differences in the positioning of ions and solid inclusions when subjected to the fields of the internal electromagnetic blood flow sensor, the net effect on making flow determination does not vary with the fluid content. Bevier presented a particularly relevant theory for appreciating these charge phenomena, (Bevier, The Theory of Induced Voltage Electromagnetic Flow meter, Vol. 43, 1970, pp 577-590, incorporated in its entirety herein by reference). Bevier's theory of the virtual current has been useful to the inventors in practically understanding how the inventive device functions and providing its optimization.

The operation of the electromagnetic flow sensor of embodiments of the invention depends on the fact that when an electrical conductor moves through a magnetic field at right angles to the lines of magnetic force, a potential difference is produced within the conductor at right angles to both the direction of the magnetic lines of force and the direction of motion of the conductor. Thus, if the ends of the conductor are connected through an external circuit, a current will flow, i.e., an electromotive force will be induced.

The magnitude of the induced electromotive force depends on the strength of the magnetic field, the extent of the conductor in the direction of the potential gradient and the velocity of motion of the conductor in the direction at right angles to the lines of magnetic force. Importantly, the strength of the induced electromotive force is independent of the nature of the material composing the conductor.

Mathematically, the strength of the induced electromotive force may be expressed:

$$E = HLv10^{-8} \quad (4)$$

where:
E is the electromotive force set up in volts,
H is the magnetic field strength in oersted,
L is the length of the conductor in centimeters at right angles to the direction of motion and the direction of the magnetic lines of force, and
v is the velocity of motion of the conductor in cm/sec in a direction at right angles to the lines of magnetic force.

If the electrodes are immersed in the flowing liquid, the physical length L will be modified to become an effective length, not necessarily equal to the electrode spacing.

As soon as the conductor moves out of the magnetic field, the electromotive force vanishes. If, however, the conductor is an electrolyte streaming in a tube of constant diameter between the magnetic poles, a potential gradient will be maintained in the electrolyte as long as it is flowing. In this case equation (4) above also applies. However, if the strength of the magnetic field and the diameter of the flowing stream at the point where the recording electrodes are attached are both maintained constant, the resulting electromotive force will vary only with the velocity and in a linear fashion. In this instance, the induced electromotive force can be described by the formula:

$$E = (H/10^{-8})v = Kv \quad (5)$$

where
I is the internal diameter of the tube, and
E is the potential difference at the ends of a diameter which forms a right angle with the lines of force.

Thus, in order to record by this method an accurate velocity curve of the blood flow within a blood vessel, the vessel may be placed in a constant and uniform magnetic field with the axis of the vessel at right angles to the lines of magnetic force. In these embodiments, the cross-sectional area of the vessel may be held constant in the plane of the electrodes.

The electrodes are then connected to a suitable recording system and the resulting variations in potential that result (e.g., and are recorded) provide a true picture without lag of the velocity variations of the blood flow within the vessel. Use of a suitable amplifier allows one to employ suitable small and weak magnets, as desired.

Embodiments of the electromagnetic sensors may be characterized as sensors that operate under conditions in which the magnetic, fluid flow and a electrode vectors span three-dimensional space, such that all three of these vectors are not coplanar.

In certain embodiments, the implantable electromagnetic fluid flow sensor includes: a pair of sense electrodes and a detection circuit, where the detection circuit is configured to: (i) detect a potential difference between the sense electrodes, the potential difference resulting from an applied magnetic field to flowing fluid at the target site of interest, and (ii) produce an output signal at an output node, the output signal correlating to the detected potential difference. In certain embodiments, the applied magnetic field is an alternating current magnetic field having an alternating frequency and the detection circuit is configured to detect the potential difference at the alternating frequency, i.e., the same frequency as the alternating current magnetic field that is applied.

As reviewed below, the magnetic field that applied during operation may be applied from a source that is internal to the body or external to the body. As such, in certain embodiments, the sensor itself includes a magnetic field production element, e.g., one or more coils.

In certain embodiments, the sensors may be characterized in that the various elements of the device are present on a surface of a solid support. The solid support may have a variety of different configurations, such as planar, e.g., chip like, curvilinear, e.g., cylindrical (e.g., a cardiovascular lead) and tubular (e.g., a stent) etc., where the surface on which the various elements are present may be an internal surface or an external surface, depending on the particular embodiment.

Figure 16A:
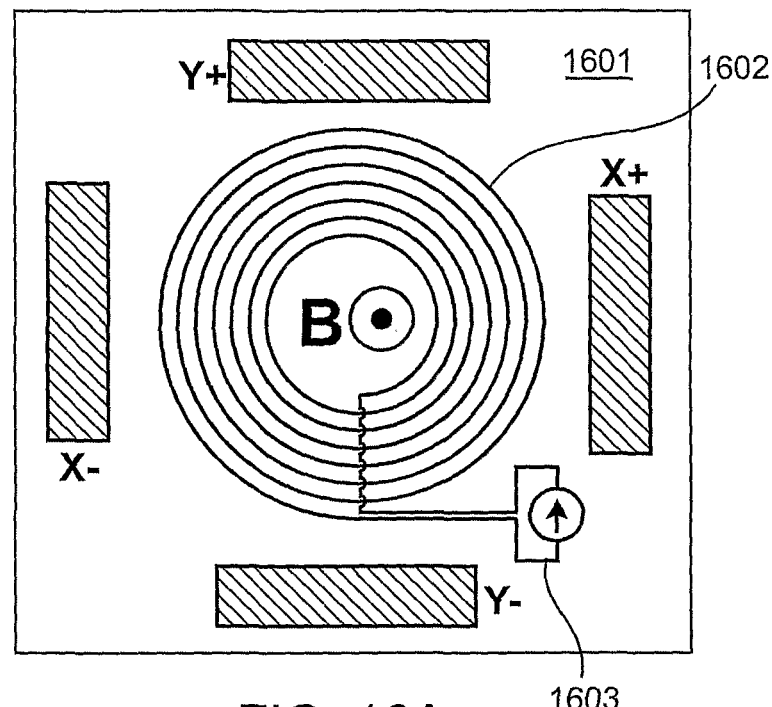
FIGS. 16A and 16B provide diagrams of planar implementations of an internal electromagnetic blood flow sensor in accordance with embodiments of the invention.
Figure 16B:
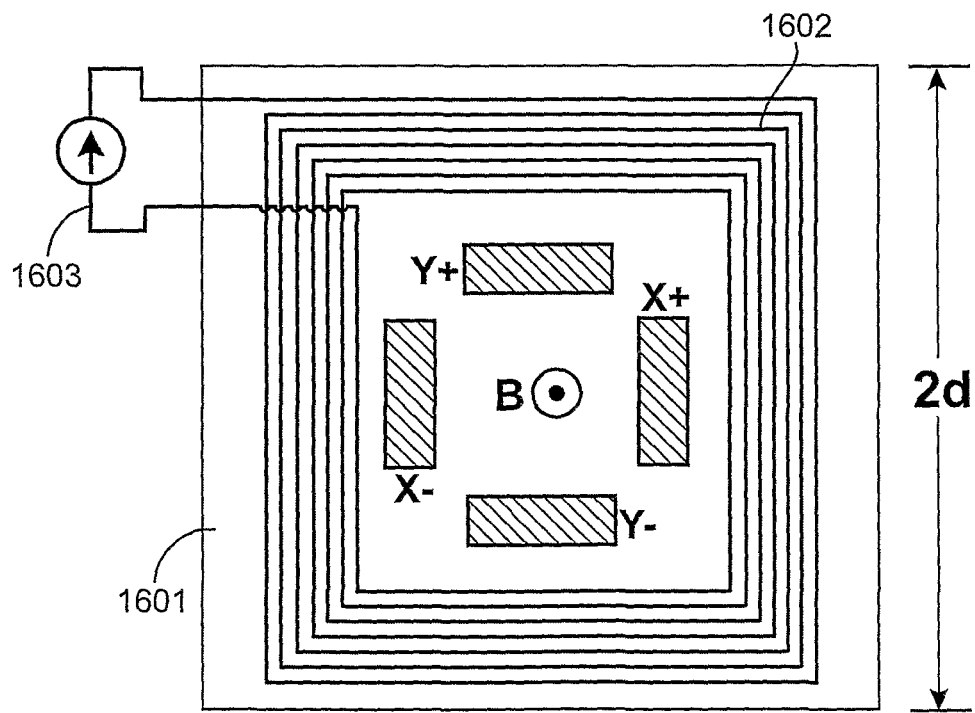

FIGS. 16A and 16B show two different embodiments of planar implementations of an internal electromagnetic blood flow sensor in accordance with the invention. The embodiments of these figures have a microchip configuration, as shown, wherein circuitry (e.g., in the form of coils and electrodes) for implementing the sensors is present on the same planar surface of a planar substrate 1601. The devices shown in these figures include a coil 1602 for applying a magnetic field. A current source 1603 drives current around the coil. A series of electrodes are situated around the coil, shown in an X+ and an X− and a Y+ and a Y− electrode. FIG. 16A shows a configuration where the electrodes are external to a circular coil 1602. FIG. 16B show a configuration where a square coil 1602 is situated around the four electrodes.

During use of the internal electromagnetic blood flow sensor, the magnetic field induces an electromagnetic potential in the blood fluid. The induced potential is detected on the electrodes. Because there are two pairs of sensing electrodes, the direction in the plane of the electrodes that the fluid is flowing may also be determined, as desired. The strengths of these fields can be described in SI Units using the following formulas:

$$E = v \times B$$
$$B = \frac{\mu_0 N I}{2d}$$

This implies $$\Delta V = 2dvB$$
$$= \mu_0 v N I$$

which is completely scale independent.

For v=1 m/s, N=$10^3$, I=$10^{-3}$ A, a sensitivity of $$1.26 \, \frac{\mu V}{m/s}$$

is achieved.

This analysis demonstrates that the internal electromagnetic blood flow sensor is completely scale independent. By example, large or small internal electromagnetic blood flow sensors will provide the same magnitude of signal. The magnitude of the signal is only determined by the number of turns in the coil and the amount of current that is pushed through the coil. Therefore, if the device were initially designed on a large scale, this design can be arbitrarily miniaturized, while providing the same signal, with the proviso that the number of turns and the amount of current going through the coil is maintained.

The calculation using a hundred turns in the coil and ten 4 amps current going through the coil and the signal comes out to be quite small, that is $10^{-11}$ volts. Microvolt sensitivities are possible with a thousand turns in the coil and the current of a milliamp. This provides one microvolt per meter per second of flow sensitivity, which is clinically very useful. As a point of reference, aortic blood flow rates are typically a few meters per second.

Such an embodiment of the internal electromagnetic blood flow sensor easily detects such physiological parameters as aortic blood flow rates. As by the above analysis, the device can be constructed to an arbitrarily small miniaturization, the device can be constructed as a chip one centimeter across. Such a chip can be pushed up against the aortic wall to provide an ongoing blood flow rate reading. The device can also be scaled to the size of a grain of dust attached into an area of interest with a catheter-based deployment mechanism.

Figure 17:
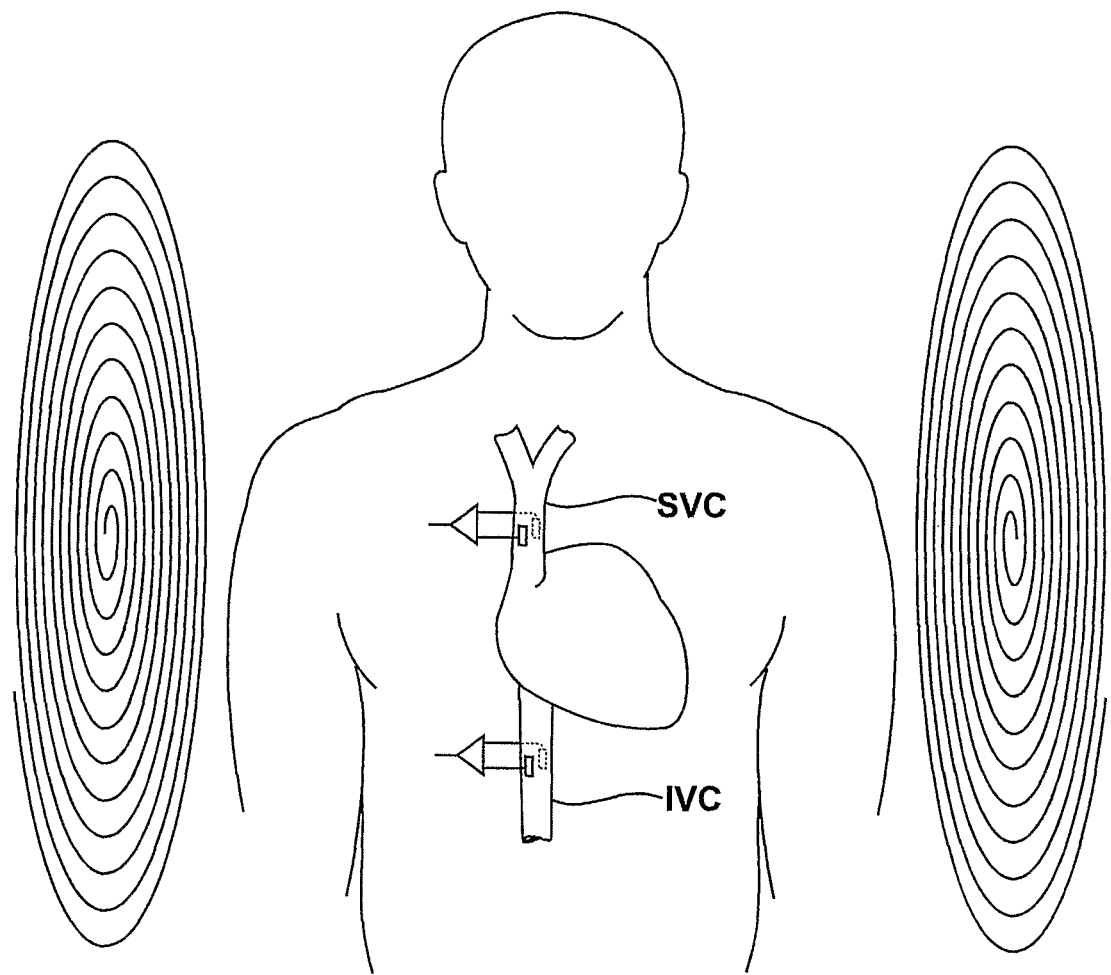
FIG. 17 provides a view of application of internal electromagnetic blood flow sensor where the magnetic field is produced using external coils, in accordance with an embodiment of the invention.

FIG. 17 is a view of an embodiment of the internal electromagnetic blood flow sensor where the magnetic field is applied using external coils. These large coils generate a larger magnetic field than could be produced by coils integrated on the same chip as the sense electrodes. This embodiment works under the same general principle described above, but the application is somewhat different. Typically, a tenth of a Tesla is employed. FIG. 17 shows two pairs of electrodes. One pair of electrodes is provided in the superior vena cava. A second pair of electrodes is provided in the inferior vena cava. With these two pairs of electrodes, the total venous blood flow into the heart is measured. The calculations are so provided to neglect the contribution from the inter-cardiac circulation, which is a small correction not difficult to make. Using the device as described, the total flow into the heart is provided. From this data, by integrating over a cardiac cycle, the stroke volume is calculated. This has the advantage that the hardware that needs to be implanted in the patient is minimal. All that is required is two pairs of electrodes and some amplifiers. Most of the work is done by the external coils, which may easily be provided in a doctor's office. Such devices can be designed and built into an operating table. Such devices allow monitoring blood flow during a surgical procedure. The layout can be very straight forward, similar to airport metal detectors. The patient can simply walk through such devices which then measure the blood flow. In acute implementation, external coils are required for the device to provide the desired data.

Figure 18:
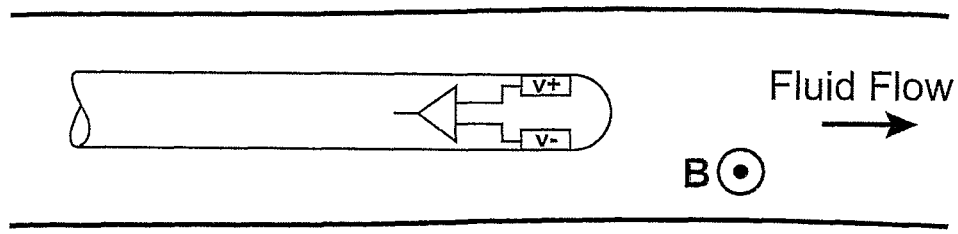
FIG. 18 provides a view of an internal electromagnetic blood flow sensor in a multi-electrode lead, in accordance with an embodiment of the invention.

FIG. 18 shows an example of lead embodiment of the sensors, where multiple electrodes on a multiplex lead, such as those described above, are used to provide the electrode pairs, analogous to those shown in FIG. 17. This embodiment is one illustration of a sensor in which the components are present on a surface of a curvilinear solid support (e.g., a lead), where the components are present on the outer curvilinear surface of the solid support. It is advantageous to situate the electrodes on the edges of the blood vessel, spread far apart. This configuration provides most of the current flowing through the blood vessel, providing higher sensitivity. Where multiplex leads with quadrant electrodes are employed, opposing quadrants of satellite electrodes are employed to give a detectable signal. In certain embodiments, some signal may be lost because the current comes up out of the electrodes, and then comes around and loops back to the negative electrode. However, a significant signal is still generated. By simply adding an external magnetic field and a difference amplifier, multi-electrode lead quadrant electrodes function as blood-flow sensors. Wherever quadrant electrodes have been deployed in the body, with a minimal extra hardware, they can be configured as blood flow sensors in accordance with the invention.

Figure 19:
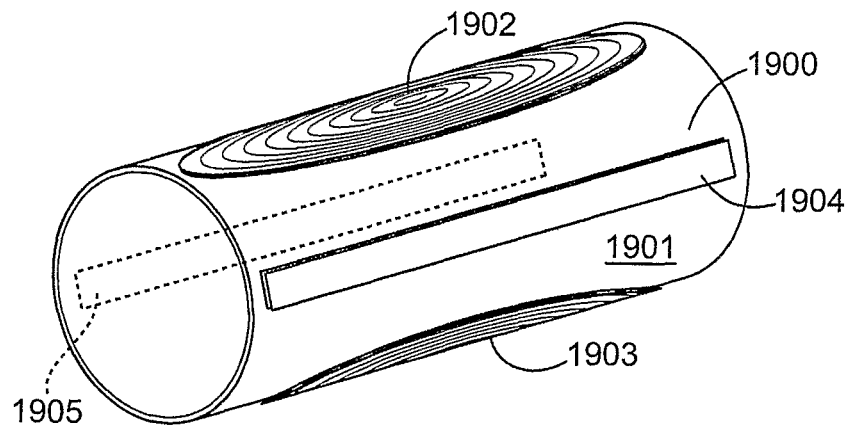
FIG. 19 provides a view of a stent-style blood flow sensor, in accordance with an embodiment of the invention.

FIG. 19 provides a stent-style blood flow sensor 1900 embodiment of the present invention. This embodiment represents another embodiment of a curvilinear solid support, where the components are present in a inner curvilinear surface of the support. This tubular structure is inserted into a blood vessel. Once inserted, the sensor pushes up against the walls. On two opposing sides of the stent substrate 1901, coils 1902 and 1903 are provided which generate the magnetic field. On the other two opposing sides of substrate 1901, electrodes 1904 and 1905 sense the induced voltage. The stent 1900 may be coated with a non-conductive material, as sing a standard metal stent may short out the effect. The stent-style blood flow sensor embodiment of the present invention has special features which gives it many advantages. The mechanical stability of the stent holds the geometry in place, making the sensor very stable over time. Any change in distance between the sense electrodes results in a change in signal, which would appear as a drift. The stent implementation of the present invention can be mechanically fixed so that there is very little motion. The coils 1902 and 1903 in the stent-style blood flow sensor embodiment of the present invention can provide geometry advantages. The coils can be provided as multi-turn coils. This geometry allows the opportunity to put significant current through the coils, generating a large signal. Such a stent-style sensor can be placed in the aorta. An advantageous use of such a device would be as part of an aneurism repair operation. In this case, the device would be built into the stent that is used to patch the aneurism. Alternately, a stent embodiment of the internal electromagnetic blood flow sensor is placed into a carotid artery or vena cava. The ease of placement at virtually any relevant cardiac position where a stent is installed as part of the stent device provides added functionality of blood flow measurement.

A monitoring device would be provided in a stent positioned embodiment of the internal electromagnetic blood flow sensor. A number of transmission mechanisms are useful in this system. The simplest is a wired mechanism where wires are going back to central controller, such as a pacing can. Transmission technology disclosed previously by the present inventor in various patent applications can also be employed, such as the method for transmitting information through the body wirelessly, e.g., as described above.

Figure 20:
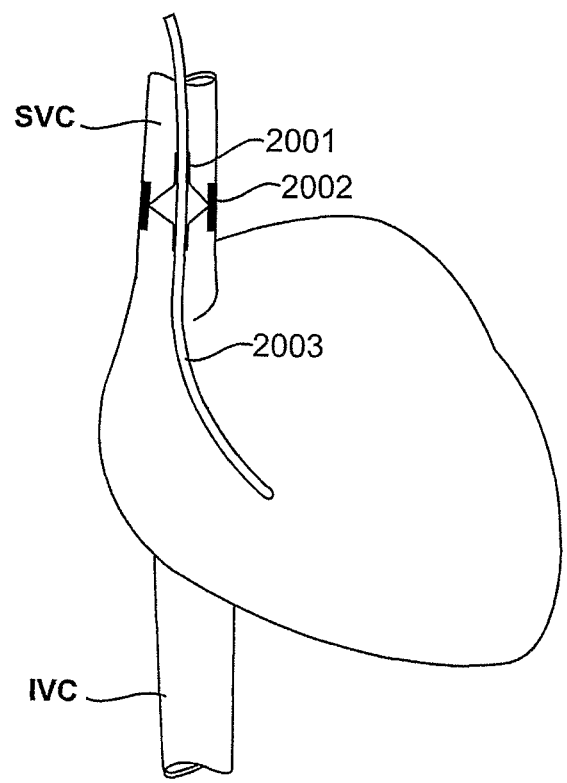
FIG. 20 shows the stent-style blood flow sensor of FIG. 19 placed in the aorta of a patient.
Figure 21:
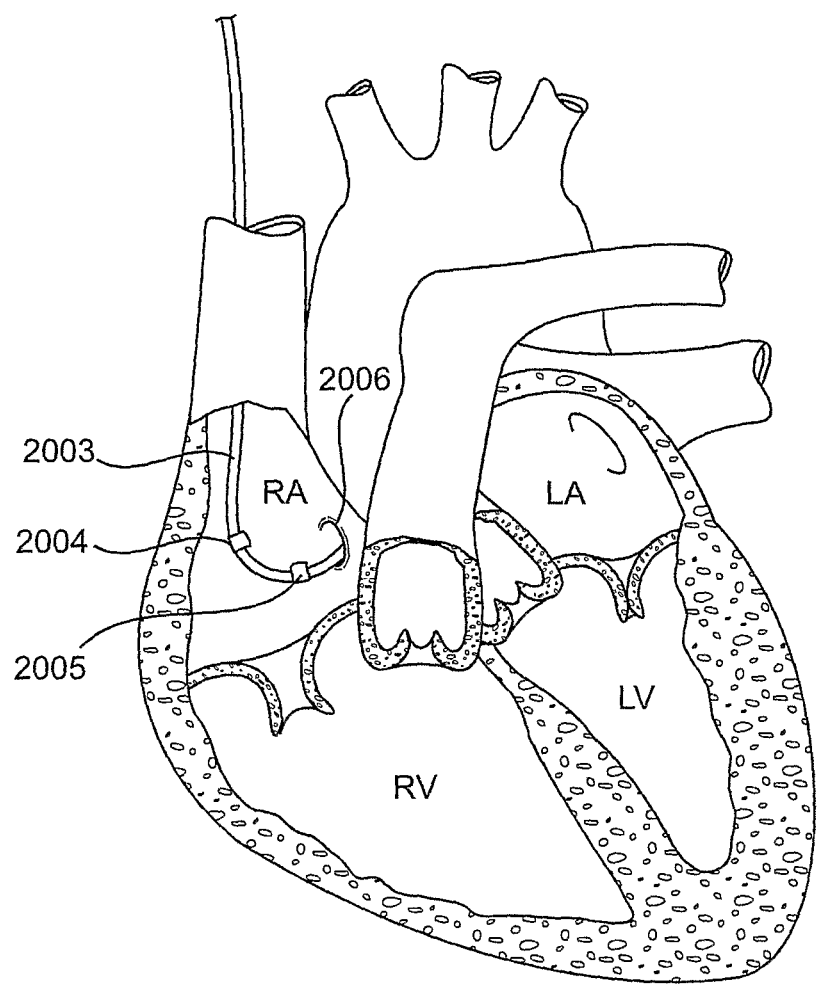
FIG. 21 provides a method of fixation providing an advantageous position for the sensor, in accordance with an embodiment of the invention.
Figure 22:
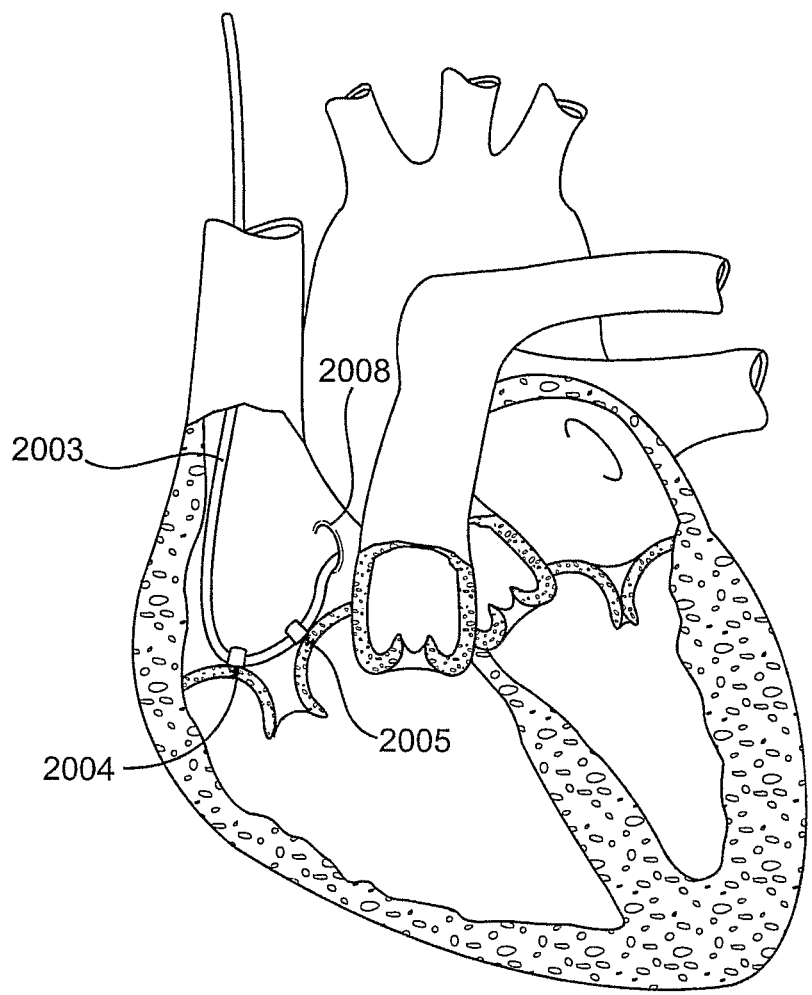
FIG. 22 shows a placement approach of sensors on either side of a cardiac valve in a patient, according to an embodiment of the invention.

FIG. 20 provides an example of an internal electromagnetic blood flow sensor 2001 built onto a fixation mechanism 2002 of a lead 2003 going down the superior vena cava through the vestibule into the heart. A fixation mechanism can optionally be provided to hold this lead in place, many of which are well know to the ordinary skilled artisan. In the present illustration, an umbrella opening type device is shown. Other mechanisms are provided with prongs coming out and pushing against the vein wall to hold it in place. Whatever fixation mechanism elected, at the end of the device are provided sense electrodes for detecting the blood flow from the magnetic field. A variation on the FIG. 20 implementation is shown in FIGS. 21 and 22, and is also advantageous. In the implementation shown in FIG. 22 the blood flow is sensed as it passes from the right atrium into the right ventricle. In cardiac resynchronization procedures it is common to bring a lead down the superior vena cava through the vestibule into the right atrium and then down into the coronary sinus. In reviewing a three dimensional model of the heart, the opening for the coronary sinus 2006 is quite close to the valve which connects the right atrium to the right ventricle. Such a position is a natural place to measure blood flow because all systemic circulation passes through this valve. To enjoy the benefit of this advantageous positioning, sense electrodes 2004 and 2005 are affixed on this lead 2003 at either side of the tricuspid valve. The flow is then detected using an external magnetic field. That is, the blood flow passing from the right atrium into the right ventricle is used. This provides a measure of the systemic circulation deriving stroke volume by integrating over a cardiac cycle, and so forth. This embodiment of the internal electromagnetic blood flow sensor can be accomplished with the multielectrode lead, such as those described above, by simply placing two additional electrodes in the appropriate place. The doctor would install these electrodes in the most advantageous position. The electrodes would then be fixed to prevent their movement over the course of not only the procedure but over the entire time when measurements were taken. Otherwise, there is the risk of the shifting appearing as a drift of some sort. The mechanism to understand the placement of these electrodes is to use the virtual current formalism to look at how the virtual current flows. A configuration is then derived where the current flow is stable over time and not sensitive to small displacements of the electrodes.

FIG. 21 provides a method of fixation providing an advantageous position for the sensor. The tip of the lead is lodged in the coronary sinus, suspending the sensing electrodes 2004 and 2005 to sense the flow through the blood flow through the atrium. FIG. 22 shows an additional, advantageous placement approach. In this case, the electrodes 2004 and 2005 are attached on either side of the valve, with the end of the lead placed in the coronary sinus for added stability. Here, the sensing has high clinical pertinence, and the blood flow directly through the valve is accurately assessed.

The application of the magnetic field in the internal electromagnetic blood flow sensor can be accomplished using any convenient approach. In FIG. 17 the application of the magnetic field is shown simply as two Helmholtz coils, but many other configurations can be implemented in the internal electromagnetic blood flow sensor. The applied magnetic field may be an AC or DC magnetic field. In certain embodiments, the magnetic field is aligned in a perpendicular fashion relative to (or at least substantially orthogonal to) both the flow direction and the sense electrode axis. In general two coils may not accomplish this aim in every position. In such cases, the patient may be instructed to change position to optimize the signal. However, there are other implementations which will limit or eliminate the need for patient repositioning. By forming three pairs of Helmholtz coils, an X pair, a Y pair and a Z pair, and balancing these appropriately, the direction of the magnetic field vector can, in effect, be changed while maintaining constant strength and magnitude of the field. In this way, the direction of magnetic field which corresponds to maximum signal strength across the electrodes can be determined. Once this condition of maximum signal strength is established, one can ensure that the magnetic field is perpendicular to the plane defined by the flow direction and the electrode axis. As such, certain embodiments include positioning the electrodes of the sensor, applying the magnetic field and determining the position of the sensor electrodes relative to the field. This approach would accomplish a set up and calibration mechanism to achieve the optimum direction to apply the magnetic field.

3. Additional Fluid Flow Sensor Considerations

It is to be understood that the sensor embodiments described herein are illustrative and that variations and modifications are possible. Further, multiple sensors can be implanted at different locations in a patient's circulatory system to measure localized blood flow parameters in a variety of different locations, e.g., sequentially or simultaneously. All of the sensors may transmit their data directly to a central data collection device (e.g., a pacemaker control can) using wireless signaling as described above or through a conductive member in a multiplex lead, depending on the configuration of the system in which the sensors are employed. From the central collection point, the data may be processed and/or forwarded to an external device for processing. The data collection device can be internal or external as desired; for instance, a collection device can be implemented as a watch or belt with electrodes that contact the patient's skin while the patient wears the device. An external device may provide audible and/or visual information to the patient or clinician, including alerts, measurement data and the like. Such a device may also include a communication port via which the device can be connected to a computer to which data collected by the device can be transferred.

It should be noted that the sensor embodiments described herein can be implanted and operated for an indefinite period, including while the patient goes about his or her normal activities. Depending on how power is supplied to the sensor, the sensor can be operated continuously or on some duty cycle selected by the clinician. Data reported by the sensors can be stored in the collection device until the patient visits the clinician, at which time the clinician can read out the data and evaluate the patient's condition. In some embodiments, the collection device may also be able to generate an audible or visible alert to the patient if data indicating an abnormal condition are received; the alert prompts the patient to seek medical care.

In certain embodiments, measurements are obtained at two different frequencies and the sensor is appropriately configured to obtain measurements at two different frequencies. In such embodiments, a first frequency may be higher than a second frequency. For example, a first higher frequency may range from about 100 kHz to about 1 MHz, and a second frequency may range from about 30 kHz to about 50 kHz. Based on the detected signals at each frequency, one can detect the presence of cells present in the target fluid site, e.g., either qualitatively or quantitatively. For example, if no cells are present, there is substantially no difference in detected signal at the different frequencies. However, if cells are present, the signal detected at each frequency will differ. In this manner, the presence of cells in the target fluid flow site under analysis can be determined, either quantitatively or qualitatively.

4. Applications of Blood Flow Measurements

With the above blood flow sensor devices, a number of physiological parameters can be derived from the measurements (e.g., blood resistivity, induced EMF) reported by sensors of the type described herein. These parameters can be used to diagnose a patient's condition, determine a treatment plan, and modify the treatment plan based on the response as determined from continued use of the sensors.

For example, "stroke volume" refers to the amount of blood moved into and out of the heart over a cardiac cycle. In one embodiment, a sensor is positioned to detect flow velocity of blood through a blood vessel located near the heart. From the perspective of accuracy, the aorta is a desirable location for implanting the sensor; however, medical considerations may make an implant into the aorta impractical. The vena cava, which is generally accessible during catheterization procedures, is another suitable site for the implant. The diameter or cross-sectional area of the selected blood vessel at the implant site is measured, e.g., directly (while the vessel is being accessed for the implant), by statistical estimation (e.g., based on an average over a suitable population of patients), by electrical tomography, or by any other suitable technique. The flow rate multiplied by the cross sectional area provides a flux measurement that can be integrated over the duration of a cardiac cycle to determine the total volume of blood passing through the vessel. Stroke volume provides one measure of heart health.

As another example, blood vessel blockages can be detected by implanting a flow sensor in any location where development of a blockage (or worsening of a partial blockage) is anticipated. Occlusion of the blood vessel will affect the blood velocity profile for the vessel, with the effect being stronger as the degree of occlusion increases. Thus, a flow sensor as described herein can be used to monitor a blood vessel for blockages, either acute or chronic. For example, an acute thrombosis could be detected in this manner, with detection triggering an alert to the patient and/or automatic release of an anti-coagulant. Chronic growth of a plaque deposit in a blood vessel can also be measured by detecting changes in the resistivity as the flow rate changes over time.

Additional metrics of heart health can also be defined. For example, as noted above, blood resistivity varies directly with flow velocity and inversely with hematocrit. As a result, it can be difficult to separate the effects of flow velocity and hematocrit on a resistivity measurement. In the short term, hematocrit is effectively constant and this is not an issue, but for longer term monitoring, the possible variation of hematocrit and its effect on resistivity should be considered. Metrics in which the hematocrit dependence is removed (e.g., by cancellation in a ratio) can advantageously be used to facilitate long-term monitoring of changes in heart health. For instance, if $v_{max}$ is the maximum flow velocity during a cardiac cycle and $v_{min}$ is the minimum flow velocity, one can define a flow ratio $\eta$ as:

$$\eta = \frac{v_{max}}{v_{min}}. \tag{6}$$

One might expect $\eta$ to be large for a healthy heart and small for a weak or diseased heart. An advantage of such a metric is that in resistivity-based blood flow sensors (e.g., as described above), it can be difficult to disentangle the effects of flow velocity and hematocrit; in Eq. (6), any hematocrit dependencies would cancel out. Other similar metrics could also be constructed and validated through clinical observation.

In other embodiments, hematocrit and flow are measured separately. In one embodiment, hematocrit is determined by measuring resistivity in a region where flow velocity is known (and preferably fixed). In another embodiment, small flow sensors detect the passage of individual red blood cells. For instance, the sensor embodiment shown in FIG. 13 above can be fabricated on a semiconductor substrate with the distance S in the 6-8 micron range.

For a semi-infinite medium, the voltage V measured by a device of this kind is given by:

$$V = \frac{\rho I}{2\pi S}, \tag{7}$$

where $\rho$ is the resistivity of the medium and I is the applied current. (See Barber & Brown, *J. Phys. E: Sci. Instrum.*, 17, 723 (1984).) In physiological situations, the approximation of a semi-infinite medium can be questionable, but Eq. (7) becomes reliable as the device size S becomes small relative to other dimensions (e.g., diameter of the blood vessel). In this context, departures from Eq. (7) will tend to be characterized by a geometrical factor of order unity, making the approximation reliable.

When the dimension S becomes comparable to the size of a red blood cell (RBC), a new effect becomes detectable. As individual RBCs pass close to the sensor, they create discrete disruptions in the potential field, analogous to shot noise in electronic circuits. This effect may be used to count individual RBCs, giving an absolute measure of hematocrit. The variation in the resistance arising from different orientations of the RBCs gives a measurement of the flow, separating the hematocrit and flow-velocity effects on resistivity. See e.g., FIGS. 23 and 24A to 24C. These two parameters can then be used as distinct measures of a patient's health.

In other embodiments, blood flow sensors are used in detection of injury (e.g., bleeding) and wound management. Any injury that results in internal or external bleeding will also change the flow profile in blood vessels surrounding the injury site. According, flow sensors can be implanted at or near an injury site or surgical site to detect whether bleeding has stopped. In the case of surgical sites, it may be useful to implant such sensors to detect internal bleeding after the surgery so that action can be taken even before symptoms are apparent.

Still other embodiments use blood flow as an indicator of physiological activity in body tissues or organs to which blood is supplied. It is generally known that as systems, organs or tissues in the body become more active, blood flow to those locations increases in order to satisfy the increased metabolic demand. For instance, blood flow to various areas of the brain increases when those areas are active (e.g., during various kinds of mental activity). Blood flow sensors in or around the brain can be used to detect such activity and to associate various mental activities with the relevant regions of the brain. Absence of increased blood flow in situations where it would be expected may also indicate an abnormality.

In a related embodiment, sensors as described herein are employed to construct a "lie detector." By studying subjects engaged in deceptive and non-deceptive behavior, characteristic differences in blood flow patterns (e.g., certain areas of the brain might become more active) are identified; and these differences are then used to detect deceptive behavior in other subjects. Similarly, the stomach and intestines receive increased blood flow during digestion; thus, digestive processes can be detected and monitored using sensors placed in gastric blood vessels.

Abnormal tissues, such as malignant tumors, can also be monitored, as blood flow to the tumor will depend on the size of the tumor and whether it is growing or shrinking. Changes in blood flow in a vessel feeding the tumor can provide an indication as to how effectively a given course of treatment is working. This information can be used by a clinician in determining whether to continue or change the treatment.

It will be appreciated that the uses described herein are illustrative and that the invention is not restricted to particular uses for blood flow measurements.

C. Implantable Drug Delivery

In certain embodiments, the system include drug delivery capability, e.g., where one or more of the devices of the system act as drug delivery devices. For example, one of the devices may be an implantable drug delivery device as described in U.S. Provisional Patent Application Ser. No. 60/824,119 titled "Personal Implantable Paramedic" and filed Aug. 31, 2006; the disclosure of which is herein incorporated by reference. As such, one or more of the devices of the system may include an implantable medical device, one or more of which may be implanted into a patient's body to allow controlled release of a biologically active agent into the body. The device(s) may comprise one or more drug filled reservoirs, an administration mechanism, a battery and/or energy capture circuit, and a microchip. Further, the device may comprise sensors which measure conditions in the body and transmit the information to a control unit which performs diagnostics. If the control unit determines that a drug should be administered, it can transmit a signal to one or more drug reservoirs to release a specific drug. The device may energize the reservoirs and/or sensors by harvesting ambient electrical energy from a source such as a defibrillator pulse. In other embodiments, the reservoirs and/or sensors may be powered by an intrinsic power source, such as a battery or radioisotope.

In one embodiment of the inventive personal implantable paramedic, the personal implantable paramedic can be built into a stent that is to be placed in the body during surgery. For example, stents are often placed in the left coronary artery of cardiac patients at risk of a heart attack. Incorporating the personal implantable paramedic into a stent that is to be inserted in the artery anyway allows for placement of the personal implantable paramedic in a highly desirable area with minimal added stress on the body. Placement in the left coronary artery also allows for delivery of a smaller drug dosage than if it were delivered from outside the body. When delivered in the left coronary artery, the drug is almost immediately drawn into the heart.

In another embodiment of the invention, the personal implantable paramedic includes a loop or other attachment that allows it to be sewn into tissue anywhere in the body. This allows it to be placed in areas of particular interest such as in the heart tissue in order to deliver drugs in case of heart attack, or in an area where a tumor is thought to be in order to deliver anti-cancer drugs.

An embodiment of the present invention may comprise any methods of administration of drugs through implantable medical devices known in the art as well as osmotic pumps, motor pumps, electrical release of wax encapsulated pharmaceuticals, and electrical release of waxed surface skin patches. Further, a method of administration may comprise a piezoelectric crystal that harvests energy and breaks a seal to release a drug. In another embodiment of the present invention, a system of more than one individually encapsulated reservoirs like that taught by Santini et al., in U.S. Pat. No. 6,849,463 filed Feb. 1, 2005 and U.S. Pat. No. 6,551,838 filed Apr. 22, 2003, may be used. Also, a method of administration may comprise a magnetic needle that injects a drug.

Materials used and methods for administration should be designed such that the personal implantable paramedic has a lifetime in the body of at least 10 years, and when needed can administer the drug in 1 second or less. These numbers are just guidelines, and are not meant to be limiting.

In one embodiment of the personal implantable paramedic, a metal or polymer layer can be placed on top of the reservoir to keep the drug inside. When it is desired for the drug to be released, the personal implantable paramedic can activate the reservoir. A current can be sent across the metal, causing it to dissolve. In the case of a polymer, the current may make it become permeable to the drug. Any metal or polymer suitable for implantation can be used. The important characteristics of the material used is that it be able to last a long time in the human body in order to avoid unwanted dispersal of the drug, while dissolving quickly when the right conditions are placed on it. The properties of the material and the thickness of the layer will determine these characteristics. Possible materials to use include any metal suitable for use in the human body, such as titanium and platinum and their alloys. The thickness should be as small as possible while still being able to last a long time in the body, i.e. at least 10 years. A thin layer allows the layer to be dissolved quickly, and also limits the amount of metal or polymer released into the body, limiting any issue with toxicity.

Another embodiment of the personal implantable paramedic uses a film, such as a metal or polymer, placed over the reservoir, which can be dissolved when the drug is desired to be released by creating a local region of different pH. For example, an electrical potential can be placed across microfabricated electrodes, releasing H+ ions, therefore lowering the pH. This can be done in a very local region, immediately surrounding the layer to be removed. The pH of blood is about 7.4, and the pH in the region local to the electrodes can be brought down to about 2 or below. A metal or polymer can be used which has a stability or solubility that is very sensitive to pH. When it is exposed to a very low pH, the material would dissolve. Alternatively, a material can be used which expands as a result of a change in pH, which increases the materials permeability enough to release the drug. Since the pH change can be done on a small scale and would occur in an area of flowing blood, the pH near the other reservoirs and in the surrounding areas would not be affected. Once the drug is released, the pH would return to normal very quickly.

In another embodiment of the personal implantable paramedic, local heat generation can be used to dissolve the encapsulation layer. For example, two electrodes with a thin wire between them can be used. When a sufficiently high current is applied between the electrodes, a high temperature can be generated locally in the vicinity of the wire. This heat can cause a polymer to dissolve or become permeable, releasing the drug. Some polymers expand as a result of temperature increase, which would increase the permeability of the encapsulation layer and allow the drug to pass through.

Another embodiment of the personal implantable paramedic utilizes one or more windows of metal or polymer that are distinct from the rest of the encapsulation layer. The window can be designed such that the release stimulus can be applied locally to the window rather than to the entire device. The window may be a region of thinner material. Alternatively, the window may be made up of a different metal or polymer composition specifically designed to rapidly release the drug in response to a stimulus, such as electrical current, pH, or temperature. This allows a small window of material that can be dissolved away, while using a more stable material for the rest of the body. The window should be as small as possible while still allowing the drug to quickly exit the window when it opens. A smaller window allows for a larger window thickness to be used with the same stimulus strength used to open it. The area of the window can be about 0.001 mm2 to about 10 mm2, more specifically about 0.01 mm2 to about 5 mm2, most specifically about 1 mm2. For a window area of mm2, the window thickness can be about 0.02 µm to about 200 µm, more specifically about 0.05 µm to about 20 µm, most specifically about 0.2 µm. The thickness used can be larger for a smaller window area, and smaller for a larger window area.

In another embodiment of the personal implantable paramedic, drug molecules can be covalently bonded to a surface using techniques well known in the art. When it is desired for the drug to be released, the covalent bond can be broken through oxidation or reduction. One possible bond to use is a carbon-silicon bond, which can be broken using techniques well known in the art. Another embodiment of the personal implantable paramedic utilizes a membrane for the encapsulation layer, and when the drug is desired to be released, a current can be applied across the membrane to drive the drug through the membrane. For example, if the drug is positively charged, and a high enough positive current is applied from the inside to the outside of the membrane, the drug can be forced out. Membrane permeability can be increased at the time of drug release by changing the local pH or temperature.

Possible polymers to use for the encapsulation layer include pH sensitive polymers which will dissolve or expand in response to a change in pH, temperature sensitive polymers which will dissolve or expand in response to a temperature change, and ion exchange membranes which will allow for the drug to pass through only when a transmembrane potential is applied.

Other embodiments of the personal implantable paramedic utilize more than one of the above mentioned mechanisms in combination to release the drug. With many drugs and encapsulation materials, one of the mechanisms may not be enough to release the drug. However, when two of the mechanisms are applied in combination, the drug may be released. For example, Titanium is a very good implant material because it has a very stable oxide layer on top of it. However, it's very difficult to dissolve the oxide layer just by applying an electrical current, If it were coupled with a change in the solution pH to a low pH, such as about 1 or 2, in the vicinity of the titanium surface, the oxide layer and the Titanium can be dissolved more easily. Other metals show similar behavior. This has the added benefit of providing a safety mechanism for the release of the drug, since it would take more than one mechanism applied in combination for the drug to be released. This would prevent unwanted release of the drug. Even if the pH were changed locally, such as from a neighboring reservoir, a current would still need to be applied across the encapsulation film for the drug to be released.

In other embodiments, any combination of any number of the mechanisms described above can be used in combination to activate the release of the drug.

One embodiment of the present invention comprises an electrical circuit which shunts ambient electrical energy emitted from a source such as a defibrillator pulse. Another embodiment of the present invention contains antennas that pull in ambient energy from a source such as a defibrillation pulse. Further, during installation of the invention, a physician could orient these reservoirs while sending a weak current through the energy source, such as the defibrillation coils, to place the reservoirs for optimum alignment to harvest energy from the defibrillation pulse. In one embodiment of the personal implantable paramedic, the energy harvesting circuit can include a bridge rectifier. In another embodiment, an active rectifier can be used.

Other power sources, such as those described above, are also of interest.

Another embodiment of the invention comprises sensors which are energized by a defibrillation pulse and broadcast data to the pacemaker which analyzes the data and sends a signal to the reservoirs to release a drug with specific dosage and timing based on the data collected from the sensors.

In one embodiment of this invention the patient will have sensors in the heart which measure blood flow through the arteries. During a defibrillation pulse the sensor is energized and measures the blood flow through the artery where the sensor is positioned. The sensor broadcasts the blood flow data to the pacemaker computer and the pacemaker computer runs diagnostics to determine the optimal therapy. The computer then sends a signal to the reservoirs to deliver the therapy. For example, if the computer diagnostics determine that the artery is clogged, the computer may signal a reservoir in the clogged artery to release some Heprin to dissolve the clot.

An embodiment of this invention comprises sensors which include, but are not limited to, sensors for blood flow, pressure and temperature as described in, but not limited to "Pressure Sensors Having Stable Gauge Transducers" U.S. Pat. No. 7,013,734 filed Mar. 21, 2006, "Pressure Sensors Having Transducers Positioned To Provide For Low Drift" U.S. Pat. No. 7,007,551 filed Mar. 7, 2006, "Implantable Pressure Sensors" U.S. Pat. No. 7,028,550 filed Apr. 18, 2006, "Pressure Sensors Having Spacer Mounted Transducers" U.S. patent application Ser. No. 11/025,793 filed Dec. 28, 2004, "Internal Electromagnetic Blood Flow Sensor" U.S. provisional patent application 60/739,174 filed Nov. 23, 2005, "Measurement of Physiological Parameters Using Dependence of Blood Resistivity on Flow" U.S. provisional patent application 60/713,881 filed Sep. 1, 2005, and "Continuous Field Tomography" PCT application PCT/US2005/036035 filed Ser. No. 10/612,005, all of which are incorporated herein by reference in their entirety.

An embodiment of this invention also comprises sensors positioned in various places of the body. Additionally, an embodiment of the present invention comprises sensors which are energized by harvesting energy from an outside event, such as a defibrillation pulse.

In one embodiment of the present invention, signal transmission and reception between the control unit, such as the pacemaker, and the reservoirs and sensors occurs according to the methods described in "Pharma-Informatics System," pending PCT application PCT/US2006/016370, filed Apr. 28, 2006 and as described above.

In one embodiment of the personal implantable paramedic, the communication system can be used to send a coded signal from a control unit to the personal implantable paramedic to deliver a specific drug. The communication system can be used to simultaneously manage a plurality of personal implantable paramedics located at different locations throughout the body.

An embodiment of this invention comprises agents often administered in drug therapies in conjunction with defibrillation pulses in emergency situations. Such drug therapies typically include, but are not limited to, 1 mg of epinephrine, 1 mg atropine, 40 mg vasopressin, 150 mg amiodarone, 70 to 100 mg lidocane, and 6 to 12 mg adenosine. The amounts of these drugs administered through the personal implantable paramedic may vary from the amounts typically administered in emergency situations due to factors like proximity of the location of the personal implantable paramedic to the heart.

In an embodiment of this invention where the target organ is the heart, exemplary drugs for delivery include, but are not necessarily limited to, growth factors, angiogenic agents, calcium channel blockers, antihypertensive agents, inotropic agents, antiatherogenic agents, anti-coagulants, β-blockers, anti-arrhythmia agents, cardiac glycosides, antiinflammatory agents, antibiotics, antiviral agents, antifungal agents, agents that inhibit protozoan infections, and antineoplastic agents.

An embodiment of this invention comprises anti-coagulant factors.

Anti-coagulants include, but are not limited to, heparin; warfarin; hirudin; tick anti-coagulant peptide; low molecular weight heparins such as enoxaparin, dalteparin, and ardeparin, ticlopidine, danaparoid, argatroban, abciximab, and tirofiban.

An embodiment of this invention comprises agents to treat congestive heart failure. Agents to treat congestive heart failure include, but are not limited to, a cardiac glycoside, inotropic agents, a loop diuretic, a thiazide diuretic, a potassium ion sparing diuretic, an angiotensin converting enzyme inhibitor, an angiotensin receptor antagonist, a nitrovasodilator, a phosphodiesterase inhibitor, a direct vasodilator, an alpha.sub.1-adrenergic receptor antagonist, a calcium channel blocker, and a sympathomimetic agent.

An embodiment of this invention comprises agents suitable for treating cardiomyopathies. Agents suitable for treating cardiomyopathies include, but are not limited to, dopamine, epinephrine, norepinephrine, and phenylephrine.

An embodiment of this invention comprises agents that prevent or reduce the incidence of restenosis. Agents that prevent or reduce the incidence of restenosis include, but are not limited to, taxol (paclataxane) and related compounds; and antimitotic agents.

One embodiment of this invention comprises anti-inflammatory agents. Anti-inflammatory agents include, but are not limited to, any known non-steroidal anti-inflammatory agent, and any known steroidal anti-inflammatory agent. Anti-inflammatory agents include, but are not limited to, any known nonsteroidal anti-inflammatory agent such as, salicylic acid derivatives (aspirin), para-aminophenol derivatives (acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal anti-inflammatory agent which include corticosteriods and biologically active synthetic analogs with respect to their relative glucocorticoid (metabolic) and mineralocorticoid (electrolyte-regulating) activities. Additionally, other drugs used in the therapy of inflammation or anti-inflammatory agents including, but are not limited to, the autocoid antagonists such as all histamine and bradykinin receptor antagonists, leukotriene and prostaglandin receptor antagonists, and platelet activating factor receptor antagonists.

One embodiment of this invention comprises antimicrobial agents. Antimicrobial agents include antibiotics (e.g. antibacterial), antiviral agents, antifungal agents, and anti-protozoan agents. Non-limiting examples of antimicrobial agents are sulfonamides, trimethoprim-sulfamethoxazole, quinolones, penicillins, and cephalosporins.

An embodiment of this invention comprises anti-inflammatory agents.

Antineoplastic agents include, but are not limited to, those which are suitable for treating tumors that may be present on or within an organ (e.g., myxoma, lipoma, papillary fibroelastoma, rhabdomyoma, fibroma, hemangioma, teratoma, mesothelioma of the AV node, sarcomas, lymphoma, and tumors that metastasize to the target organ) including cancer chemotherapeutic agents, a variety of which are well known in the art.

An embodiment of this invention comprises angiogenic factors (e.g., to promote organ repair or for development of a biobypass to avoid a thrombosis). Angiogenic factors include, but are not limited to, basic fibroblast growth factor, acidic fibroblast growth factor, vascular endothelial growth factor, angiogenin, transforming growth factor α and β, tumor necrosis factor, angiopoietin, platelet-derived growth factor, placental growth factor, hepatocyte growth factor, and proliferin.

An embodiment of this invention comprises thrombolytic agents. Thrombolytic agents include, but are not limited to, urokinase plasminogen activator, urokinase, streptokinase, inhibitors of α2-plasmin inhibitor, and inhibitors of plasminogen activator inhibitor-1, angiotensin converting enzyme (ACE) inhibitors, spironolactone, tissue plasminogen activator (tPA), an inhibitor of interleukin 1β converting enzyme, and anti-thrombin III.

An embodiment of this invention comprises calcium channel blockers.

Calcium channel blockers include, but are not limited to, dihydropyridines such as nifedipine, nicardipine, nimodipine, and the like; benzothiazepines such as dilitazem; phenylalkylamines such as verapamil; diarylaminopropylamine ethers such as bepridil; and benzimidole-substituted tetralines such as mibefradil.

An embodiment of this invention comprises antihypertensive factors.

Antihypertensive agents include, but are not limited to, diuretics, including thiazides such as hydroclorothiazide, furosemide, spironolactone, triamterene, and amiloride; antiadrenergic agents, including clonidine, guanabenz, guanfacine, methyldopa, trimethaphan, reserpine, guanethidine, guanadrel, phentolamine, phenoxybenzamine, prazosin, terazosin, doxazosin, propanolol, methoprolol, nadolol, atenolol, timolol, betaxolol, carteolol, pindolol, acebutolol, labetalol; vasodilators, including hydralizine, minoxidil, diazoxide, nitroprusside; and angiotensin converting enzyme inhibitors, including captopril, benazepril, enalapril, enalaprilat, fosinopril, lisinopril, quinapril, ramipril; angiotensin receptor antagonists, such as losartan; and calcium channel antagonists, including nifedine, amlodipine, felodipine XL, isadipine, nicardipine, benzothiazepines (e.g., diltiazem), and phenylalkylamines (e.g. verapamil).

An embodiment of this invention comprises antiarrhythmic agents.

Antiarrhythmic agents include, but are not necessarily limited to, sodium channel blockers (e.g., lidocaine, procainamide, encamide, flecanide, and the like), beta adrenergic blockers (e.g., propranolol), prolongers of the action potentila duration (e.g., amiodarone), and calcium channel blockers (e.g., verpamil, diltiazem, nickel chloride, and the like). Delivery of cardiac depressants (e.g., lidocaine), cardiac stimulants (e.g., isoproterenol, dopamine, norepinephrine, etc.), and combinations of multiple cardiac agents (e.g., digoxin/quinidine to treat atrial fibrillation).

D. Smart Parenteral Delivery System

In certain embodiments, the communication system of the present invention is employed in a smart parenteral delivery system, e.g., as described in pending U.S. Provisional Application Ser. No. 60/819,750 titled "Smart Parenteral Delivery System" and filed on Jul. 7, 2006, the disclosure of which is herein incorporated by reference. The inventive smart parenteral delivery system of these embodiments provides specific identification and detection of parenteral beneficial agents or beneficial agents taken into the body through other methods, for example, through the use of a syringe, inhaler, or other device that administers medicine. The smart parenteral delivery system can include a beneficial agent with a chip. The chip can contain information about the type of beneficial agent to be administered to the patient. Upon extracting the beneficial agent from the holding container, e.g., a vial, a signal can be sent from the vial to a chip within the syringe. The broadcasted signal can indicate the type of beneficial agent extracted from the vial. Upon injection into the patient, the information can be sent from the syringe to an information management database located in, on, or near the patient.

VI. Additional System Considerations

While the invention has been described with respect to specific embodiments, one skilled in the art will recognize that numerous modifications and other embodiments are possible. An endless variety of networks including sensors, data collectors and effectors in any combination, communicating wirelessly in the quasi-electrostatic region, can be created and tailored to detect or treat nearly any medical condition. Examples are described above. More generally, it will be appreciated that a small autonomous chip including a power source (or power receiver), sensor, effector and/or transmitter can be placed virtually anywhere in the body. Since the chips do not have to be connected by wire to a data collection or control system, entirely new diagnostic and treatment models can be developed. Sensors can be disposed throughout the body to measure various parameters, with the data being transmitted wirelessly through the body to a central collector. Collected data can be used to automatically initiate or suspend a therapeutic activity (e.g., release of a drug, electrical or mechanical stimulation, etc.); it can also be stored for later reporting to a clinician or used to generate a real-time alert advising the patient of a developing condition even before the patient experiences symptoms.

The following are provided as further illustration of the scope of diagnostic and therapeutic techniques that can be implemented in accordance with embodiments of the present invention.

In some embodiments, one or more remote devices can be implanted in and/or around a patient's heart and/or neighboring blood vessels and used to monitor various parameters related to cardiac function on an ongoing basis, including but not limited to stroke volume (the amount of blood that moves through a vessel during a cardiac cycle), blood flow rate, hematocrit, oxygen content of blood in the aorta, and so on. Changes in any of these parameters can signal a deteriorating cardiac condition that warrants intervention.

Conventionally, however, these parameters have not been available to cardiologists on a continual basis; they can be measured only during invasive procedures that generally need to be performed in a laboratory. A cardiac monitoring system implemented on the platform herein enables the cardiologist to monitor the patient's condition on an ongoing basis. Further, since data can be collected while the patient goes about her (or his) normal daily activities, the cardiologist may obtain more accurate information about how the patient's heart is actually operating on a day-to-day basis.

Further, in embodiments where a data collector capable of generating alarms is included in the system, the patient can be immediately alerted when an event requiring immediate attention (e.g., ischemia) occurs. In still other embodiments, effectors may be automatically operated when such an event occurs, in addition to or instead of alerting the patient.

One cardiac parameter of interest is stroke volume which can be measured in various ways. For instance, a blood flow sensor as described above can be implanted in the aorta or vena cava at a region of known cross-section, and the flow rate can be integrated over a cardiac cycle, then multiplied by the cross-sectional area to determine the volume of blood passing through. Pressure sensors, electrical tomography, or strain gauges can also be employed.

Flow variation over a cardiac cycle is another indicator of heart health that can be measured effectively using the blood flow sensors described above. For instance, if $v_{max}$ is the maximum flow velocity during a cardiac cycle and $v_{min}$ is the minimum flow velocity, one can define a flow ratio $\eta$ as:

$$\eta = \frac{v_{max}}{v_{min}}. \tag{6}$$

One might expect $\eta$ to be large for a healthy heart and small for a weak or diseased heart. An advantage of such a metric is that in resistivity-based blood flow sensors (e.g., as described above), it can be difficult to disentangle the effects of flow velocity and hematocrit; in Eq. (6), any hematocrit dependencies would cancel out. Other similar metrics could also be constructed and validated through clinical observation.

Blood vessel blockages can be detected using changes in a variety of parameters, such as flow velocity, blood viscosity, blood pressure temperature, oxygen content, and presence or absence of various cellular waste products, clotting factors, and so on, any or all of which can be detected using remote devices implanted in or around blood vessels where blockage is a potential concern. In some embodiments, detection of an acute blockage may be used to actuate an effector that releases an anti-coagulant, or it may result in an alert to the patient to seek medical attention. Chronic blockage can be monitored over time to determine whether and what type of intervention is warranted.

Another area of application is in wound management and injury detection. For example, sensors in accordance with the present invention can provide measurement data that would provide an early indication as to infection and/or healing in a wound. Chemical sensors might be implanted at a wound site to detect, e.g., clotting agents, antibodies, and the like; variations might indicate infection or other problems. Temperature sensors could also be implanted at a wound site, with a temperature increase at the site providing an early indication of infection. Further, blood flow sensors can be placed at sites where internal bleeding is a potential risk and use to detect when bleeding in an area has stopped. In addition, sensors equipped to detect signs of injury or infection could be implanted in patients with impaired nerve function; a data collection device would alert the patient in the event of injury or infection, potentially avoiding loss of fingers, toes, or limbs due to unnoticed infections.

Similarly, sensors configured to detect cancer markers might be implanted in the bloodstream or elsewhere of patients at risk for occurrence or recurrence of cancer. The presence or level of a cancer marker over time can be studied by a clinician, or a rise in the level of a marker might be used to signal the patient to seek medical attention. Where tumors are present, sensors can be implanted to monitor growth or shrinkage of the tumor, e.g., based on changes in blood flow, pressure exerted by the tumor on surrounding tissues, or the like.

Cancer therapies, such as radiation therapy, can also be managed using an embodiment of the present invention. For instance, radiation sensors can be placed in a tumor or in surrounding healthy tissue, and the levels of radiation detected by different sensors can be used to adjust the aim or focus of radiation beams to more selectively target tumor cells, preserving healthy tissue.

In still other embodiments, physiological activity levels of systems, organs and tissues can be monitored on an ongoing basis using suitably configured and placed sensors with transmitter capability. For instance, temperature increases typically accompany increased activity in an organ; alternatively or in addition, blood flow sensors might also be used to register increased blood flow as tissues become more active; such sensors can be used, e.g., for monitoring brain activity. Pressure sensors, strain sensors or the like can also be employed to detect wanted or unwanted muscle contractions, including stomach and/or intestinal contractions, uterine contractions, muscle spasms (e.g., in the back), and the like. It may be possible to detect certain conditions, e.g., irritable bowel syndrome, muscle spasms, or the like well before pathologic sequeli, such as diarrhea or back pain, are ascertainable by the patient. In some instances, detection of unwanted activity increases might trigger automatic release of a counteractive agent (e.g., a muscle relaxant) even before the patient becomes aware of symptoms.

The platform described herein also has applicability to medical research. For instance, data from the pill-ingestion system described above can be correlated with data from other sensors and used to evaluate the effectiveness of new pharmaceuticals or other therapies. In addition, data from healthy patients could be collected and compared to data from diseased patients, providing a better understanding of which parameters are the most reliable indicators of disease.

Embodiments of the invention further include implantable diagnostic and/or therapeutic platforms in which the disparate components of the system communication wirelessly with each other and/or to a central device, where the central device (hub) includes a processor which causes an action based on information provided from one or more implanted remote devices. For example, a plurality of disparate remote sensor devices may be implanted throughout the body of a patient and communicate physiological data to a central processing unit, e.g., present in a "can" or some other internal processing device. Based on the communicated information, the processor may then send out an activation signal to one or more effector remote devices to perform some remedial action, e.g., administer a quantity of drug, apply an electrical stimulus, etc. In this fashion, a highly controlled diagnostic and/or therapeutic system can be provided to a patient which provides therapeutic treatment to a patient based uniquely on the patient's individual physiological parameters and in real time when the therapy is most needed. In addition, therapy can be modulated or titrated based on detected parameters, e.g., more or less agent can be administered based on a detected physiological parameter. For example, a cardiac system may be deployed with a plurality of remote devices, including both sensor and effector devices, positioned around the hear, e.g., as described above. The sensor devices may wirelessly relay physiological data, e.g., fluid flow date, pressure data etc., to a central processor present in a can. Based on the received data, the can may make therapeutic treatment decisions, e.g., how much cardiac drug to administer from an effector, what kind of electrical stimulation to administer and where, and then communicated signals to appropriate effectors to achieve the desired therapeutic treatment.

VII. Systems

Aspects of the invention include systems, including implantable medical devices and systems, which include the devices of the invention, e.g., remote devices that wirelessly communication with each using a quasi-electrostatic protocol (as described above); fluid flow sensors, e.g., resistive flow sensors, electromagnetic flow sensors, etc. The systems may perform a number of different functions, including but not limited to: diagnostic applications, therapeutic applications, etc.

The systems may have a number of different components or elements, where such elements may include, but are not limited to: sensors; effectors; processing elements, e.g., for controlling timing of cardiac stimulation, e.g., in response to a signal from one or more sensors; telemetric transmitters, e.g., for telemetrically exchanging information between the implantable medical device and a location outside the body; drug delivery elements, etc.

In certain embodiments, the implantable medical systems are ones that are employed for cardiovascular applications, e.g., pacing applications, cardiac resynchronization therapy applications, etc.

Use of the systems may include visualization of data obtained with the devices. Some of the present inventors have developed a variety of display and software tools to coordinate multiple sources of sensor information which will be gathered by use of the inventive systems. Examples of these can be seen in international PCT application serial no. PCT/US2006/012246; the disclosure of which application, as well as the priority applications thereof are incorporated in their entirety by reference herein.

Data obtained using the implantable embodiments in accordance with the invention, as desired, can be recorded by an implantable computer. Such data can be periodically uploaded to computer systems and computer networks, including the Internet, for automated or manual analysis.

Uplink and downlink telemetry capabilities may be provided in a given implantable system to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the system to the external programmer or other remote medical device in response to a downlink telemetry transmitted interrogation command. The real-time physiologic data typically includes real time sampled signal levels, e.g., intracardiac electrocardiogram amplitude values, and sensor output signals including dimension signals developed in accordance with the invention. The non-physiologic patient data includes currently programmed device operating modes and parameter values, battery condition, device ID, patient ID, implantation dates, device programming history, real time event markers and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

VIII. Kits

Also provided are kits that include one or more components of the systems, e.g., as described above. For example, the kits may include a device, e.g., either implantable or ingestible, that is configured to at least one of: (i) transmit a signal via a quasi electrostatic coupling to the body of the patient; and (ii) receive the transmitted signal via a quasi electrostatic coupling to the body of the patient. In certain embodiments, the kits may include two or more such devices. In certain embodiments, the kits may include fluid flow sensors as described above, e.g., present on a lead or as a remote implantable device.

In certain embodiments, the kits further include at least a control unit, e.g., in the form of an ICD or pacemaker can. In certain of these embodiments, the structure and control unit may be electrically coupled by an elongated conductive member. In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

The following examples are offered by way of illustration and not by way of limitation.

EXPERIMENTAL

Example

Blood Flow in Vena Cava

An experiment was performed using a blood flow sensor of the type described herein. The experimental setup and results are presented by way of illustrating the efficacy of an embodiment of the present invention, and this description is not intended to limit the scope of the claims.

Resistivity blood flow sensors as described above were employed. Using a pig as the test subject, one sensor (with a pair of electrodes) was placed in the superior vena cava (SVC) and another in the inferior vena cava (IVC), and a two-point measurement was performed. Constant voltage was applied between each pair of electrodes, and the voltage across a 10-ohm resistor in series was measured. The measured voltage is proportional to current and thus inversely proportional to impedance between the two electrodes in the pair.

Figure 14A:
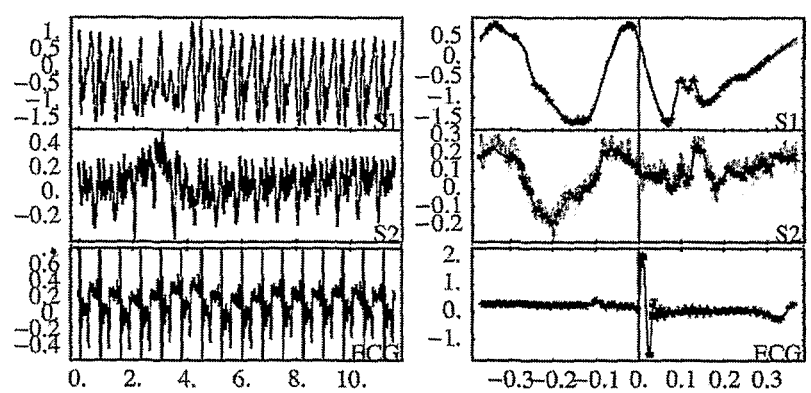
FIGS. 14A to 14C are results obtained from experiments using a resistance blood flow sensor as described in the Experimental Section, below.
Figure 14B:
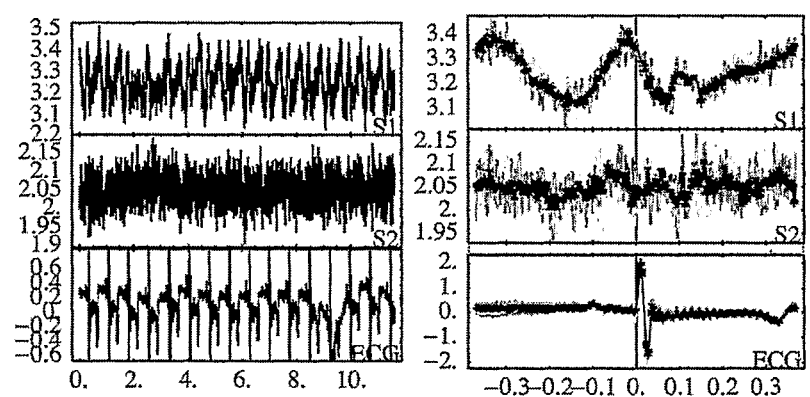

FIGS. 14A and 14B are results obtained from experiments in an anesthetized pig. The top panel (S1) corresponds to the SVC, and the second panel (S2) corresponds to the IVC. The bottom panel (ECG) corresponds to an electrocardiogram taken at the same time as the data. Panels in the left column show a time trace of about 12 seconds, and the right column shows data for several cardiac cycles (as determined from the ECG readings) overlaid. In this setup, it is expected that increased blood velocity should correspond to more positive readings, and indeed one sees that the blood velocity varies systematically across a cardiac cycle.

Figure 14C:
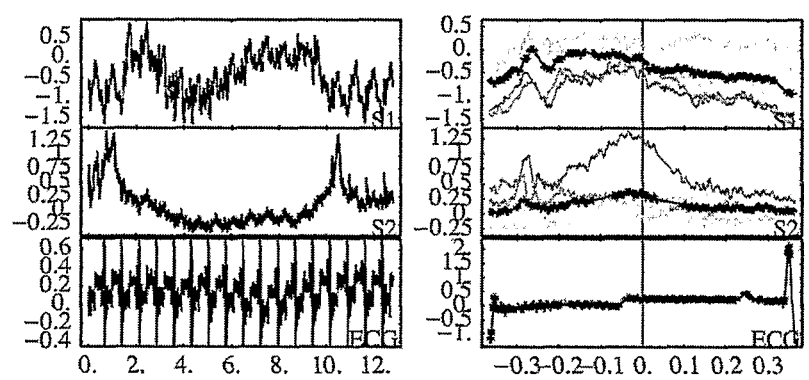

FIG. 14C shows results from an experiment in which a balloon was inflated to occlude the IVC, blocking blood flow. The experiment began with the balloon deflated; after about 2 seconds, the balloon was inflated over 2-3 seconds, held full for 2 seconds, then deflated over 2-3 seconds. The SVC panel (S1) shows that the flow rate in the SVC generally increased when the IVC was blocked, since the SVC must provide more blood to fill the heart when the IVC is blocked. When the IVC was unblocked, restoring the flow, the flow rate in the SVC decreased. The dip at around 4 seconds is believed to be due to a systemic effect: the increased flow "sucked the SVC dry" until hemodynamic systems could compensate.

The IVC panel (S2) shows that the flow rate in the IVC spiked as the vessel was pinched off by the inflating balloon, with blood rushing through the narrow opening between the vessel wall and the balloon. The blood flow generally decreased below baseline (see FIGS. 14A and 14B) when the vessel was completely blocked, although the effect is not as dramatic as might have been expected. The results also show that the variation of flow rate within a cardiac cycle is decreased when the vessel is occluded.

Thus, measuring electrical resistivity (or conductivity) as described herein is a viable tool for monitoring the patient's circulatory system, including the development of vessel blockages.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for communicating information within a body of a patient, the system comprising:
    (a) a first device comprising a transmitter configured to transmit a quasi-electrostatic signal via a quasi-electrostatic coupling to the body of the patient; and
    (b) a second device comprising a receiver configured to receive the transmitted quasi-electrostatic signal via a quasi-electrostatic coupling to the body of the patient;
    wherein the quasi-electrostatic signal is transmitted between the first and second device within the body of the patient and wherein the body of the patient is the conducting medium for the quasi-electrostatic signal.

2. The system according to claim 1, wherein said system includes at least a third device which is configured to at least one of:
    (i) transmit a quasi-electrostatic signal via a quasi electrostatic coupling to the body of the patient; and
    (ii) receive the transmitted quasi-electrostatic signal via a quasi electrostatic coupling to the body of the patient
    wherein the quasi-electrostatic signal is transmitted between the first and second device within the body of the patient and wherein the body of the patient is the conducting medium for the quasi-electrostatic signal;
    wherein the quasi-electrostatic signal is transmitted and received by the third device within the body of the patient and wherein the body of the patient is the conducting medium for the quasi-electrostatic signal.

3. The system according to claim 1, wherein said quasi-electrostatic signal comprises data produced by said first device.

4. The system according to claim 1, wherein said quasi-electrostatic signal comprises an identifier of said first device.

5. The system according to claim 1, wherein said quasi-electrostatic signal is used by said second device as a power source.

6. The system according to claim 1, wherein said first device is an implantable medical device.

7. The system according to claim 6, wherein said first device includes a sensor.

8. The system according to claim 7, wherein said sensor is a blood flow sensor.

9. The system according to claim 8, wherein said blood flow sensor comprises a resistivity sensor.

10. The system according to claim 8, wherein said blood flow sensor comprises an electromagnetic blood flow sensor.

11. The system according to claim 6, wherein said first device includes an effector.

12. The system according to claim 11, wherein said effector comprises an electrode.

13. The system according to claim 1, wherein the first device comprises an ingestible medical device.

14. The system according to claim 1, wherein the first device is an external device configured to contact a surface of the body of the patient and is capable of detecting and/or generating the quasi-electrostatic signal through the skin of the body of the patient.

15. The system according to claim 1, wherein the second device is an implantable medical device.

16. The system according to claim 15, wherein the second device is further configured to retransmit the received signal to a secondary receiver external to said patient.

17. The system according to claim 16, wherein said secondary receiver further comprises a radio frequency (RF) receiver and RF transmitter.

18. The system according to claim 16, wherein said second device includes a transcutaneous wire configured to retransmit the received information to the secondary receiver.

19. The system according to claim 16, wherein said secondary receiver is internal to said patient.

20. The system according to claim 1, wherein the second device is a pacemaker.

21. A communications device for use within a body of a patient, said communications device comprising:
(a) a power supply;
(b) a signal generating circuit coupled to said power supply and configured to generate a quasi-electrostatic signal; and
(c) an antenna coupled to said signal generating circuit and configured to transmit said quasi-electrostatic signal via quasi-electrostatic coupling to said body;
wherein the quasi-electrostatic signal is transmitted from said antenna within the body of the patient and wherein the body of the patient is the conducting medium for the quasi-electrostatic signal.

22. The communications device according to claim 21, wherein said power supply comprises a battery.

23. The communications device according to claim 21, wherein said power supply comprises:
(i) an antenna configured to receive energy from an energy source via a quasi-electrostatic coupling to said body; and
(ii) a converter circuit configured to convert the received energy to electrical power.

24. The communications device according to claim 21, wherein said antenna comprises a pair of electrodes separated by a gap.

25. The communications device according to claim 21, wherein said signal generating circuit is further configured to generate a quasi-electrostatic signal representing information.

26. The communications device according to claim 25, wherein said signal generating circuit comprises an oscillator coupled to said antenna.

27. The communications device according to claim 26, wherein said oscillator is configured to operate at a frequency such that a radiation field generated by the antenna has a wavelength more than 10 times longer than a largest dimension of said body.

28. The communications device according to claim 27, wherein said oscillator is configured to operate at a frequency of about 10 MHz or less.

29. The communications device according to claim 28, wherein said oscillator is configured to operate at a frequency of between about 300 Hz and about 1 MHz.

30. The communications device according to claim 21, wherein said signal generating circuit comprises:
(i) a driver coupled to drive a time varying potential on said antenna;
(ii) an oscillator having an output coupled to said driver; and
(iii) a modulator configured to modulate a frequency of the oscillator output so as to encode the information.

31. The communications device according to claim 21, wherein said signal generating circuit comprises:
(i) a driver coupled to drive a time varying potential on said antenna;
(ii) an oscillator having an output coupled to said driver; and
(ii) a modulator configured to modulate a phase of said oscillator output so as to encode the information.

32. The communications device according to claim 21, wherein said signal generating circuit includes:
(i) a driver coupled to drive a time varying potential on said antenna;
(ii) an oscillator having an output coupled to said driver; and
(iii) a modulator configured to modulate an amplitude of said oscillator output so as to encode the information.

33. The communications device according to claim 21, wherein device is an implantable medical device.

34. The communications device according to claim 33, wherein said device includes a sensor.

35. The communications device according to claim 34, wherein said sensor is a blood flow sensor.

36. The communications device according to claim 35, wherein said blood flow sensor comprises a resistivity sensor.

37. The communications device according to claim 35, wherein said blood flow sensor comprises an electromagnetic blood flow sensor.

38. The communications device according to claim 33, wherein said device includes an effector.

39. The communications device according to claim 38, wherein said effector comprises an electrode.

40. The communications device according to claim 21, wherein the device is an ingestible medical device.

41. The communications device according to claim 21, wherein said device is a pharmaceutical delivery device.

42. A method for communicating information within a body of a patient, said method comprising:
(a) operating a transmitter of a device located within said body to generate a quasi-electrostatic signal; and
(b) detecting said quasi electrostatic signal using a receiver;
wherein the quasi-electrostatic signal is transmitted from said transmitter within the body of the patient and wherein the body of the patient is the conducting medium for the quasi-electrostatic signal.

43. The method according to claim 42, wherein said receiver is disposed within said body.

44. The method according to claim 42, wherein said receiver is in contact with an external surface of said body.

45. The method according to claim 42, wherein said device is an implantable medical device.

46. The method according to claim 45, wherein said device includes a sensor.

47. The method according to claim 46, wherein said sensor is a blood flow sensor.

48. The method according to claim 47, wherein said blood flow sensor is a resistivity sensor.

49. The method according to claim 47 wherein said blood flow sensor is an electromagnetic blood flow sensor.

50. The method according to claim 45, wherein said device includes an effector.

51. The method according to claim 50, wherein said actuator comprises an electrode.

52. The method according to claim 42, wherein the device is an ingestible medical device.

53. A kit comprising at least one of:
(a) a first device comprising a transmitter configured to transmit a signal via a quasi-electrostatic coupling to a body of a patient; and
(b) a second device comprising a receiver configured to receive the transmitted signal via a quasi-electrostatic coupling to said body;
wherein the quasi-electrostatic signal is transmitted from said transmitter within the body of the patient and wherein the body of the patient is the conducting medium for the quasi-electrostatic signal.

54. The kit according to claim 53, wherein said kit comprises both of said first and second devices.

* * * * *